(12) United States Patent
Sengupta et al.

(10) Patent No.: US 10,512,696 B2
(45) Date of Patent: *Dec. 24, 2019

(54) NANOSCALE PLATINUM COMPOUNDS AND METHODS OF USE THEREOF

(71) Applicant: THE BRIGHAM AND WOMEN'S HOSPITAL, INC., Boston, MA (US)

(72) Inventors: Shiladitya Sengupta, Waltham, MA (US); Abhimanyu Paraskar, Belmont, MA (US); Shivani Soni, La Canada Flintridge, CA (US); Sudipta Basu, Cambridge, MA (US); Poulomi Sengupta, Belmont, MA (US)

(73) Assignee: THE BRIGHAM AND WOMEN'S HOSPITAL, INC., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/182,967

(22) Filed: Jun. 15, 2016

(65) Prior Publication Data

US 2016/0367682 A1 Dec. 22, 2016

Related U.S. Application Data

(62) Division of application No. 13/147,751, filed as application No. PCT/US2010/023217 on Feb. 4, 2010, now Pat. No. 9,393,227.

(Continued)

(51) Int. Cl.
*A61K 33/24* (2019.01)
*A61K 31/282* (2006.01)
(Continued)

(52) U.S. Cl.
CPC .......... *A61K 47/489* (2013.01); *A61K 31/282* (2013.01); *A61K 31/382* (2013.01);
(Continued)

(58) Field of Classification Search
None
See application file for complete search history.

(56) References Cited

U.S. PATENT DOCUMENTS 4,680,338 A * 7/1987 Sundoro .......... G01N 33/54353
435/174
4,931,553 A 6/1990 Gill et al.
(Continued)

FOREIGN PATENT DOCUMENTS

CN 1911450 A 2/2007
EP 0307827 A2 3/1989
(Continued)

OTHER PUBLICATIONS

Avgoustakis et al., "PLGA-mPEG nanoparticles of cisplatin: in vitro nanoparticle degradation, in vitro drug release and in vitro drug release and in vivo drug residence in blood properties", Journal of Controlled Release 79:123-135 (2002).

(Continued)

*Primary Examiner* — Bethany P Barham
*Assistant Examiner* — Dominic Lazaro
(74) *Attorney, Agent, or Firm* — Nixon Peabody LLP

(57) ABSTRACT

The invention is directed to biocompatible conjugated polymer nanoparticles including a copolymer backbone, a plurality of sidechains covalently linked to said backbone, and a plurality of platinum compounds dissociably linked to said backbone. The invention is also directed to dicarbonyl-lipid compounds wherein a platinum compound is dissociably linked to the dicarbonyl compound. The invention is also directed to methods of treating cancer or metastasis. The methods includes selecting a subject in need of treatment for cancer or metastasis and administering to the subject an effective amount of any of the nanoparticles, compounds, or compositions of the invention.

6 Claims, 40 Drawing Sheets

Related U.S. Application Data

(60) Provisional application No. 61/149,725, filed on Feb. 4, 2009, provisional application No. 61/240,007, filed on Sep. 4, 2009.

(51) Int. Cl.

| | | |
|---|---|---|
| *C08F 8/32* | (2006.01) | |
| *C07J 41/00* | (2006.01) | |
| *A61K 47/48* | (2006.01) | |
| *A61K 31/382* | (2006.01) | |
| *A61K 47/24* | (2006.01) | |
| *A61K 47/16* | (2006.01) | |
| *C08F 22/06* | (2006.01) | |
| *C08F 222/06* | (2006.01) | |
| *A61K 47/60* | (2017.01) | |
| *A61K 47/54* | (2017.01) | |
| *A61K 47/58* | (2017.01) | |
| *A61K 47/69* | (2017.01) | |

(52) U.S. Cl.
CPC .............. *A61K 33/24* (2013.01); *A61K 47/16* (2013.01); *A61K 47/24* (2013.01); *A61K 47/543* (2017.08); *A61K 47/544* (2017.08); *A61K 47/58* (2017.08); *A61K 47/60* (2017.08); *A61K 47/6933* (2017.08); *C07J 41/0055* (2013.01); *C08F 8/32* (2013.01); *C08F 22/06* (2013.01); *C08F 222/06* (2013.01)

(56) References Cited

U.S. PATENT DOCUMENTS

| | | | |
|---|---|---|---|
| 5,091,521 A | 2/1992 | Kolar et al. | |
| 5,547,982 A | 8/1996 | Abrams et al. | |
| 5,871,710 A | 2/1999 | Bogdanov et al. | |
| 6,365,179 B1 | 4/2002 | Zalipsky et al. | |
| 6,365,197 B1 | 4/2002 | Shukla et al. | |
| 7,208,611 B2 | 4/2007 | Gao et al. | |
| 9,393,227 B2 * | 7/2016 | Sengupta | C08F 22/06 |
| 2003/0129224 A1 | 7/2003 | Tardi et al. | |
| 2005/0136258 A1 | 6/2005 | Nie et al. | |
| 2008/0063701 A1 | 3/2008 | Keller et al. | |
| 2008/0145416 A1 | 6/2008 | Bronich et al. | |

FOREIGN PATENT DOCUMENTS

| | | | |
|---|---|---|---|
| JP | 2008-509205 A | 3/2008 | |
| WO | 89/10928 A1 | 11/1989 | |
| WO | WO-03047549 A2 * | 6/2003 | ........... A61K 9/1272 |
| WO | 2004/078121 A2 | 9/2004 | |
| WO | 2006/016097 A2 | 2/2006 | |
| WO | 2008/112565 A2 | 9/2008 | |

OTHER PUBLICATIONS

Awasthi, "A Dendrimer-Based Prodrug for Use in an Anti-Cancer Nanocell", Master's Thesis: Massachusetts Institute of Technology 1-72 (2007).
Bacu et al., "Potential drug delivery systems from maleic anhydride copolymers and phenothiazine derivatives", European Polymer Journal 38:1509-1513 (2002).
Cha et al., "Preparation and Characterization of Cisplatin-Incorporated Chitosan Hydrogels, Microparticles, and Nanoparticles", Macromolecular Research 14(5):573-578 (2006).
Chadha et al., "Drug Carrier Systems for Anticancer Agents: A Review", Journal of Scientific & Industrial Research 67:185-197 (2008).
Dhar et al., "Targeted delivery of cisplatin to prostate cancer cells by aptamer functionalized Pt(IV) prodrug-PLGA-PEG nanoparticles", PNAS 105(45):17356-17361 (2008).
Fujiyama et al., "Cisplatin incorporated in microspheres: development and fundamental studies for its clinical application", Journal of Controlled Release 89:397-408 (2003).
Gabizon, "Targeting Folate Receptor with Folate Linked to Extremities of Poly(ethylene glycol)-Grafted Liposomes: In Vitro Studies", Bioconjug. Chem. 10:289-298 (1999).
Gryparis et al., "Effect of Conditions of Preparation on the Size and Encapsulation Properties of PLGA-mPEG Nanoparticles of Cisplatin", Drug Delivery 14(6):371-380 (2007).
Haag et al. "Polymer Therapeutics: concepts and applications", Angew. Chem. Int. Ed. 45:1198-1215 (2006).
Harrington et al., "Phase I-II study of pegylated liposomal cisplatin (SPI-077TM) in patients with inoperable head and neck cancer", Annals of Oncology 12:493-496 (2001).
Haxton et al., "Polymeric Drug Delivery of Platinum-Based Anticancer Agents", Journal of Pharmaceutical Sciences 98:2299-2316 (2009).
Henry et al., "pH-Responsive Poly(styrene-alt-maleic anhydride) Alkylamide Copolymers for Intracellular Drug Delivery", Biomacromolecules 7:2407-2414 (2006).
Jin et al., "Degradable Cisplatin-Releasing Core-Shell Nanogels form Zwitterionic Poly (β-Aminoester)-Graft-PEG for Cancer Chemotherapy", Drug Delivery 14:279-286 (2007).
Kelland, "The resurgence of platinum-based cancer chemotherapy", Nat Rev Cancer 7(8):573-84 (2007).
Lin et al., "Improved targeting of platinum chemotherapeutics: the antitumour activity of the HPMA copolymer platinum agent AP5280 in murine tumour models", European Journal of Cancer 40:291-297 (2004).
Moghimi et al., "Long-Circulating and Target-Specific Nanoparticles: Theory to Practice", Pharmacological Reviews 53:(2):283-315 (2001).
Paraskar et al., "Rationally engineered polymeric cisplatin nanoparticle for improved antitumor efficacy", Nanotechnology 22(26):265101 (2011).
Rademaker-Lakhai et al., "A Phase I and Pharmacological Study of the Platinum Polymer AP5280 Given as an Intravenous Infusion Once Every 3 Weeks in Patients with Solid Tumors", Clinical Cancer Research 10:3386-3395 (2004).
Schmidt et al., "Modification of Poly(octadecene-alt-maleic anhydride) Films by Reaction with Functional Amines", Journal of Applied Polymer Science 87:1255-1266 (2003).
Singh et al., "A cationic cytofectin with long spacer mediates favourable transfection in transformed human epithelial cells", International Journal of Pharmaceutics 309:189-198 (2006).
Shen et al., "Degradable Core-Shell Nanogels For Controlled Delivery of Cisplatin", Polymer Preprints, 46(2): 667-8 (2005).
International Search Report for PCT/US2010/023217.
Shen et al., "Degradable Core-Shell Nanogels for Controlled Delivery of Cisplatin", Polymer Preprints 46(2):667-668 (2005).

\* cited by examiner

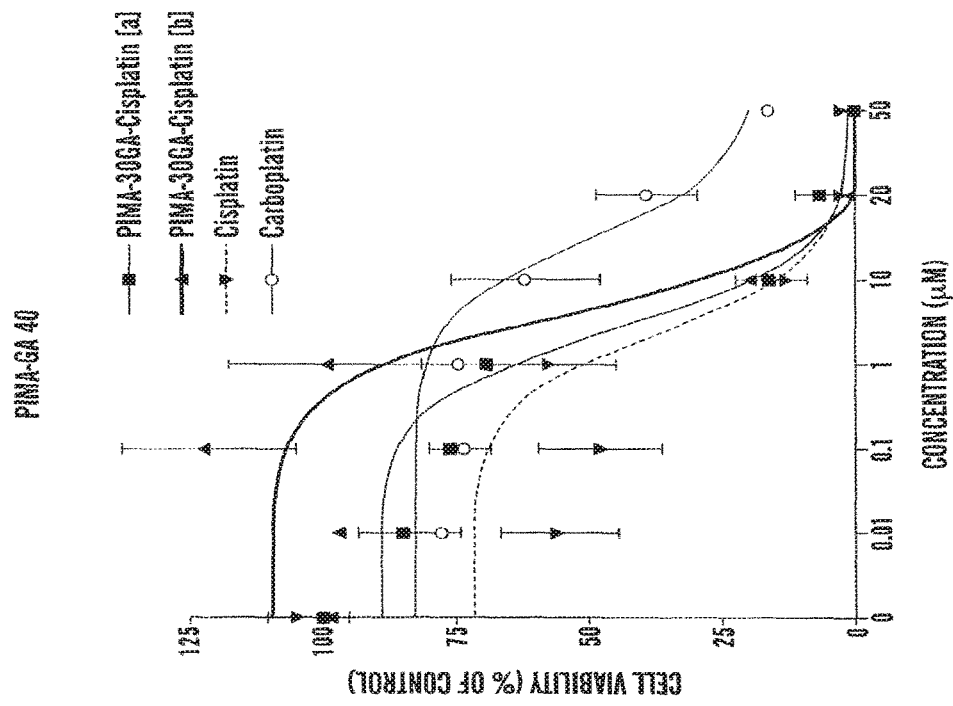
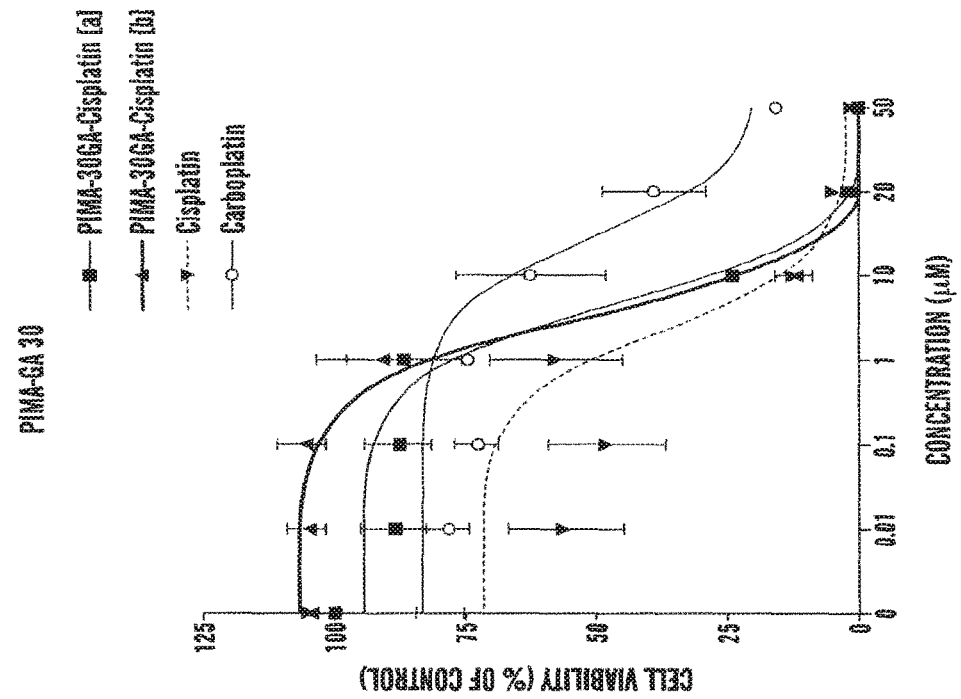
FIG. 13C
FIG. 13D

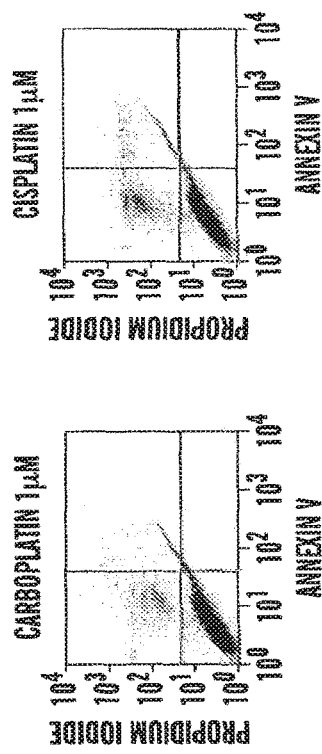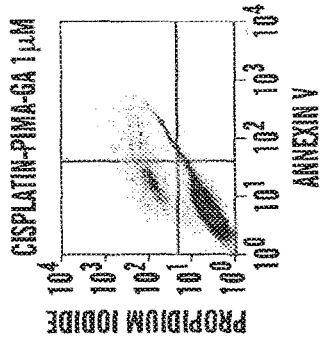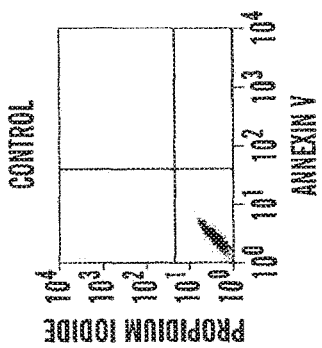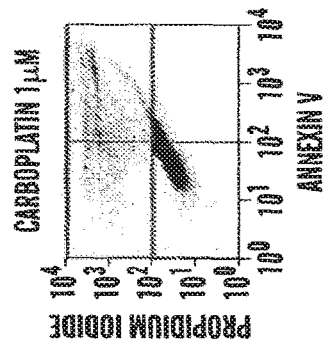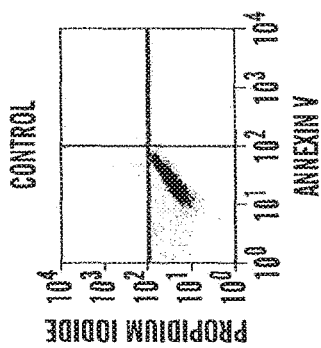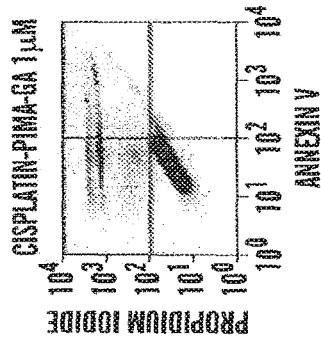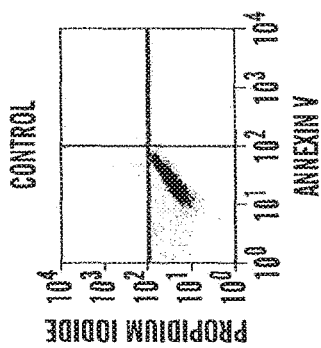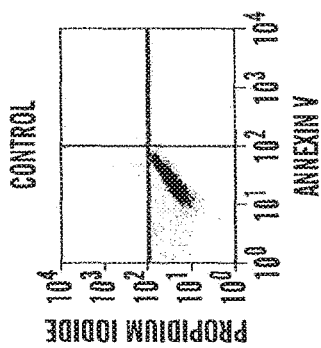

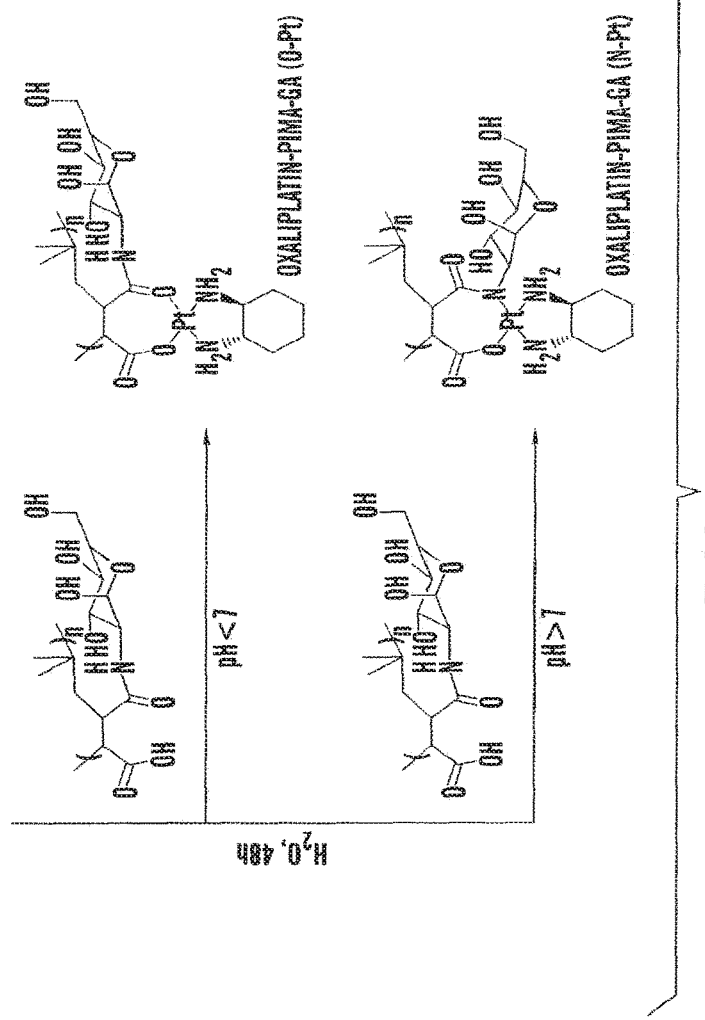
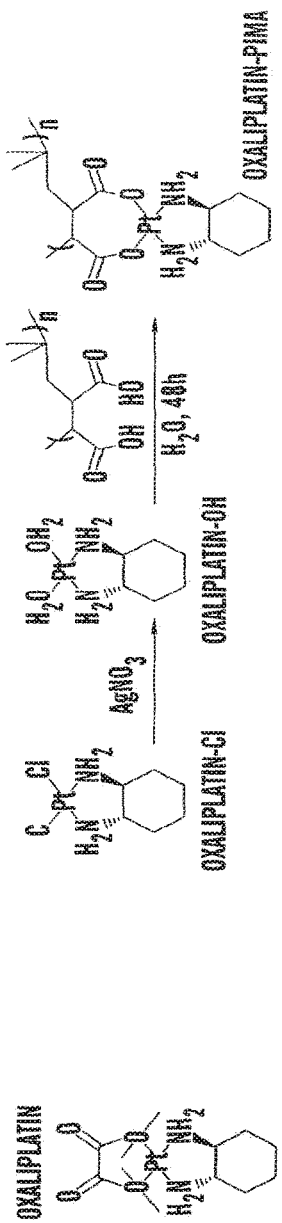
FIG. 20A
FIG. 20B

NANOSCALE PLATINUM COMPOUNDS AND METHODS OF USE THEREOF

RELATED APPLICATIONS

This application is a Divisional Application of U.S. patent application Ser. No. 13/147,751, filed on Mar. 16, 2012, now U.S. Pat. No. 9,393,227 issued on Jul. 19, 2016, which is a 35 U.S.C. § 371 National Stage Entry Application of International Application No. PCT/US2010/023217, filed Feb. 4, 2010, which designates the U.S., and which claims benefit under 35 U.S.C. § 119(e) of the U.S. Provisional Application No. 61/149,725, filed Feb. 4, 2009 and 61/240,007, filed Sep. 4, 2009, the content of all of which are incorporated herein by reference in their entirety.

GOVERNMENT SUPPORT

The subject matter of this application was made with support of a Department of Defense Era of Hope Scholar Award W81XWH-07-1-0482 and Department of Defense Postdoctoral Award W81XWH-09-1-0728. The U.S. Government has certain rights in this invention.

FIELD OF THE INVENTION

This invention relates to biocompatible conjugated polymer nanoparticles including a copolymer backbone, a plurality of sidechains covalently linked to the backbone, and, a plurality of platinum compounds dissociably linked to the backbone.

BACKGROUND OF THE INVENTION

Cancer is the second leading cause of mortality in the United States, with an estimated 1,444,180 new cases and 565,650 deaths in 2008. Cytotoxic agents, which are used in standard chemotherapy, non-specifically target all dividing cells resulting in dose-limiting toxicities. There is an urgent need to develop novel strategies that are more specifically targeted against the tumor.

The use of nanovectors holds the potential to revolutionize cancer chemotherapy by specifically targeting the tumor. A number of polymeric nanovectors are currently in development or in clinics, and are dramatically altering the pharmacodynamic and pharmacokinetic profile of the active agent. However, most of these polymeric constructs decrease the potency of the conjugated active agent, relying on increased uptake into the tumor for the improved therapeutic index.

Cisplatin is one of the mainstays in chemotherapy regimes for most types of Cancer (Kelland L. The resurgence of platinum-based cancer chemotherapy. Nat Rev Cancer. 2007 Aug. 7(8):573-84). However, its use is does-limited due to severe nephrotoxicity. Furthermore, the nanovector formulation of cisplatin, which is a first-line therapy for multiple cancers, has been a challenge.

SUMMARY OF THE INVENTION

Reported herein is a rational engineering of a polymeric construct of platinum-based chemotherapeutics such as cisplatin and oxaliplatin, which results in self-assembly into a nanoparticle. The nanoparticle sustains the potency of the active agent, and compared with cisplatin or oxaliplatin or carboplatin, exhibits increased anti-tumor effects with reduced systemic- and nephro-toxicity when administered intravenously to tumor-bearing mice. This nanotechnology-enabled improvement in the therapeutic index of cisplatin or oxaliplatin can be utilized for using nanoplatinates in the clinical management of multiple types of cancer.

The invention is directed to a biocompatible conjugated polymer nanoparticle including a copolymer backbone, a plurality of sidechains covalently linked to said backbone, and, a plurality of platinum compounds dissociably linked to said backbone. Generally, the platinum compound is dissociably linked to backbone via linkage through the sidechain. In some embodiments, the platinum compound is linked to the sidechain through at least one coordination bond.

Another aspect of the invention is directed to biocompatible conjugated polymer nanoparticles including a polymaleic acid (PMA) such as a poly(isobutylene-alt-maleic acid) (PIMA) backbone. The backbone consists of from 25 to 50 monomers. Also included are a plurality of PEG sidechains covalently linked to said backbone. The PEG sidechains have a molecular weight of from 200 to 3000 Dalton. The PEG sidechains number between 50% and 100%, inclusive, of the number of monomeric units of the polymer backbone. Also included are a plurality of cisplatin or oxaliplatin side groups dissociably linked to the backbone. The cisplatin side groups number between 25% and 75%, inclusive, of the number of monomeric units of the polymer backbone.

Yet another aspect of the invention is directed to biocompatible conjugated polymer nanoparticles including a poly(isobutylene-alt-maleic acid) backbone. The backbone consist of about 40 monomers. Also included are a plurality of PEG sidechains covalently linked to the backbone. The PEG sidechains have a molecular weight of about 2000 Dalton. The PEG sidechains number greater than 90% of monomeric units of said polymer backbone. Also included are a plurality of cisplatin or oxaliplatin side groups dissociably linked to the backbone. The cisplatin or oxaliplatin side groups number between 25% and 75%, inclusive, of the number of monomeric units of the polymer backbone.

Still another aspect of the invention is directed to biocompatible conjugated polymer nanoparticles including a poly(isobutylene-alt-maleic acid) backbone. The backbone consists of from 25 to 50 monomers. Also included are a plurality of glucosamine sidechains covalently linked to said backbone. The glucosamine sidechains number between 50% and 100%, inclusive, of monomeric units of said polymer backbone. Also included are a plurality of cisplatin or oxaliplatin side groups dissociably linked to the backbone. The cisplatin or oxaliplatin side groups number between 25% and 75%, inclusive, of the number of monomeric units of the polymer backbone.

Another aspect of the invention is directed to biocompatible conjugated polymer nanoparticles including a poly(isobutylene-alt-maleic acid) backbone. The backbone consists of from 25 to 50 monomers. Also included are a plurality of glucosamine sidechains covalently linked to said backbone. The glucosamine sidechains number greater than 75% of monomeric units of said polymer backbone. Also included are a plurality of cisplatin or oxaliplatin side groups dissociably linked to the backbone. The cisplatin or oxaliplatin side groups number between 25% and 75%, inclusive, of the number of monomeric units of the polymer backbone.

Yet another aspect of the invention is directed to carboxylic acid-platinum II (Pt(II)) complex conjugated nanoparticles including a carboxylic acid-(Pt(II)) complex and a plurality of lipid-polymer chains. The carboxylic acid portion of said carboxylic acid-cisplatin/oxaliplatin complex is covalently bound to said lipid-polymer chains.

Another aspect of the invention is directed to a vesicle, micelle, or liposome compound comprising a plurality of nanoparticles of claim as described herein.

Still another aspect of the invention is directed to pharmaceutical compositions including any of the nanoparticles or compounds described herein and a pharmaceutically acceptable carrier.

Yet another aspect of the invention is directed to a method of treating cancer or metastasis. The method includes selecting a subject in need of treatment for cancer or metastasis and administering to the subject an effective amount of any of the nanoparticles, compounds, or compositions described herein.

BRIEF DESCRIPTION OF THE DRAWINGS

FIG. 5C is a bar graph showing the blood counts between the various treatment groups. The animals were dosed thrice (shown by arrows on x-axis). Data shown are mean±SE, n=4-8. The effect of treatment on the organ weight of kidneys (FIG. 5D) and spleen (FIG. 5E) as a marker for nephrotoxicity and hematological toxicity is also shown (n=4-6). The images on top of each graph show representative organs from each treatment group. FIG. 5F shows the biodistribution of Pt in kidney and tumor as measured using ICP-spectroscopy 24 h hours following administration of free or cisplatin nanoparticles (8 mg/kg cisplatin dose)

FIG. 11A shows the mechanism underlying the intracellular activation of cisplatin through aquation. The leaving groups of cisplatin and analogues are replaced with OH prior to DNA-binding. FIG. 11B shows the chemical synthesis of PIMA-cisplatin and PIMA-glucosamine (PIMA-GA)-cisplatin complex. Transformation of polymaleic anhydride (n=40) (1) to polymaleic acid [PIMA] (2) enables complexation of $[NH_2]_2Pt[OH]_2$ through dicarboxylato bond (6). Derivatization of one arm of PIMA with glucosamine (4), and complexation with $[NH_2]_2Pt[OH]_2$ can lead to two isomers (8) and (10) depending on pH, characterized by unique Pt NMR signatures (FIG. 11B).

FIG. 12A shows that derivatization of all the monomeric units of PIMA with glucosamine and subsequent complexation with Pt forms nanoparticles smaller than 150 nm. FIG. 12B shows the total platinum loaded per mg of polymer at this ratio.

FIGS. 13A-13F are line graphs showing in vitro characterization of cisplatin nanoparticles. FIGS. 13A and 13B show the concentration-effect of different treatments on cellular viability as measured using MTS assay. X-axis shows the equivalent concentrations of cisplatin. Where blank polymeric controls were used, dose of polymer used was equivalent to that used to deliver that specific dose of cisplatin in the complexed form. PIMA was also derivatized with ethylene diamine to generate PIMA-EDA, which offers a similar complexation environment to platinum as PIMA-GA. Unlike PIMA-GA, PIMA-EDA exerted inherent toxicity. PIMA-GA-Cisplatin[acidic] refers to the isomer formed under acidic complexation environment while PIMA-GA-Cisplatin[basic] refers to the isomer formed under alkaline environment. FIGS. 13C-13F show effect of PIMA-GA-cisplatin nanoparticles on LLC cells viability, when the PIMA backbone (40 monomeric units) is derivatized to different degrees. PIMA-30GA-Cisplatin has 30 of the 40 monomeric units derivatized with glucosamine while PIMA-GA-40 and PIMA-GA-200 have all the monomeric units derivatized. [a] and [b] refers to isomers formed in acidic and basic environments when the polymers are complexed with cisplatin. Table 1 shows the corresponding IC50 values.

FIGS. 14A-14H show FACS images and FIGS. 14I and 14J are bar graphs showing that treatment with PIMA-GA-Cisplatin induces cell death. Representative FACS images of 4T1 (FIGS. 14A-14D) and LLC (FIGS. 14E-14H) cells show the percentage in each quadrant following treatments with free or nanoparticle-cisplatin. Carboplatin was used as a control for comparison (FIGS. 14D and 14H). The cells were incubated with the drugs for 24 h, following which they were labeled with Annexin-V FITC and counterstained with propidium iodide.

As shown in FIG. 18A, bioluminescence quantification indicated a significantly decreased tumor luciferase signal in mice treated with cisplatin-NP compared to vehicle (p<0.05, one-way ANOVA analysis). FIG. 18B shows drug toxicity assessed by measurements in overall body weight. Daily recording of body weights indicated a significant loss of body weight in the free cisplatin group as compared to both cisplatin-NP (1.25 mg/kg and 3 mg/kg) treated groups (P<0.05, two-way ANOVA analysis).

FIGS. 20A and 20B are schematic showing SAR-inspired engineering of a oxaliplatin nanoparticle. FIG. 20A shows the mechanism underlying the intracellular activation of oxaliplatin through aquation. FIG. 20B shows the chemical synthesis of PIMA-oxaliplatin and PIMA-glucosamine (PIMA-GA)-oxaliplatin complex. Oxaliplatin-OH can be complexed with PIMA through dicarboxylato bonds. Derivatization of one arm of PIMA with glucosamine, and complexation with oxaliplatin can lead to two isomers depending on pH.

DETAILED DESCRIPTION OF THE INVENTION

Figure 1A:
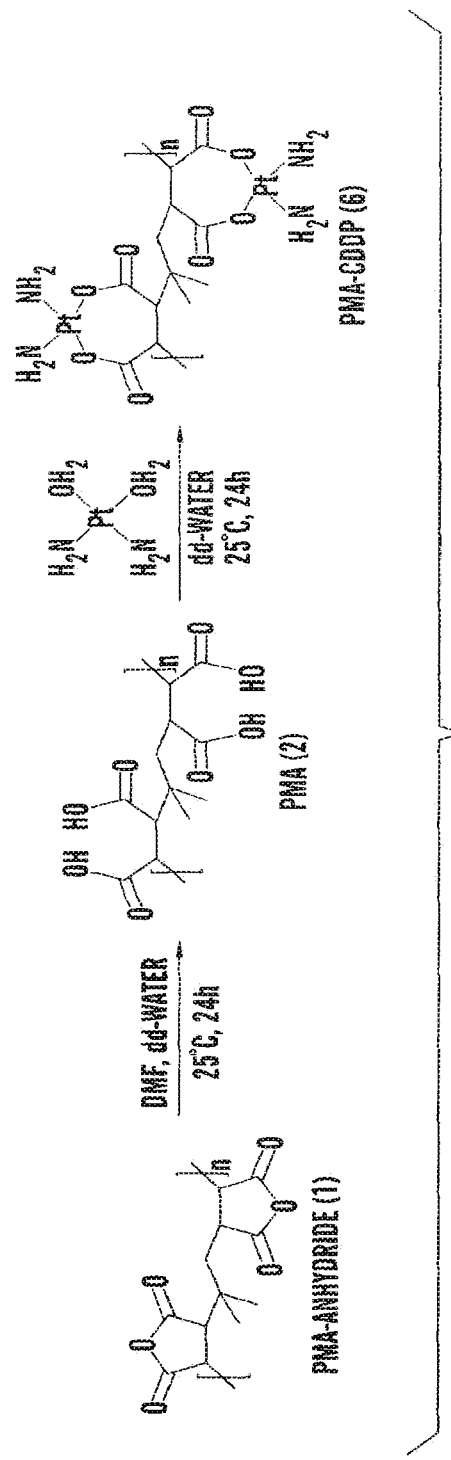
FIG. 1A shows a schematic of synthesis of PMA-Cisplatin.

The invention is directed to biocompatible conjugated polymer nanoparticles including a copolymer backbone, a plurality of sidechains covalently linked to said backbone, and, a plurality of platinum compounds dissociably linked to said backbone. Generally, the platinum compounds are linked to the backbone via a linkage to the sidechains.

In some embodiments, the copolymer comprises maleic acid monomers.

In a preferred embodiment, the copolymer is poly(isobutylene-alt-maleic acid) (PIMA or PMA).

In some embodiments, the copolymer comprises from 2 to 100 monomeric units. In some embodiments, the copolymer comprises from 25 to 50 monomeric units.

In some embodiments, the sidechains are selected from the group consisting of polymers, monosaccharides, carboxylic acids, dicarboxylic acids, amides, and combinations thereof.

In preferred embodiments, the sidechains are polyethylene glycol (PEG). PEG sidechains can be represented by —C(O)—NH-PEG.

In some embodiments, the PEG sidechains have a molecular weight of from 100 to 5000 Dalton. In some embodiments, the PEG sidechains have a molecular weight of from 1000 to 3000 Dalton. In a preferred embodiment, the PEG sidechains have a molecular weight of about 2000 Dalton.

In some embodiments, the sidechains are monosaccharides. In a preferred embodiment, the monosaccharides are glucosamine. The monosaccharide sidechains can be represented by —C(O)-saccharide.

Any platinum compound can be used in the invention. Preferably, the platinum compound is a platinum(II) or platinum (IV) compound. In some embodiments, the platinum (II) compound is selected from the group consisting of cisplatin, oxaliplatin, carboplatin, paraplatin, sartraplatin, and combinations thereof. In a preferred embodiment, the platinum (II) compound side group is cisplatin or oxalipaltin.

In some embodiments, the platinum(II) compound is selected from the group consisting of $Pt(NH_3)_2$, $Pt(NH_3)(2$-methylpyridine), and

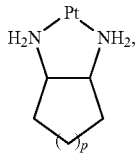

wherein p is 0-3. In a preferred embodiment, the platinum (II) compound is $Pt(NH_3)_2$.

In some embodiments, the platinum (II) compound is

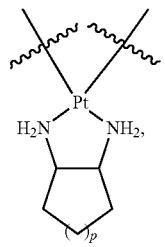

wherein p is 0-3.

In some embodiments, the platinum (II) compound comprises at least two nitrogen atoms, where said nitrogen atoms are directly linked to platinum. In a further embodiment, the two nitrogen atoms are linked to each other via an optionally substituted linker, e.g. acyclic or cyclic linker. A cyclic linker means a linking moiety that comprises at least one ring structure. Cyclic linkers can be aryl, heteroaryl, cyclyl or heterocyclyl.

In some embodiments, at least one nitrogen that is linked to platinum is a ring atom of a heteroaryl or a heterocyclyl.

In a preferred embodiment, heteroaryl is optionally substituted pyridine, e.g., 2-methylpyridine.

In some embodiments, the plurality of sidechains corresponds to a number between 50% and 100%, inclusive, of the number of monomeric units of said polymer backbone. This means that between 50% to 100% of the monomeric units have at least one sidechain linked to the monomeric unit. The total number of sidechains can be greater than the total number of the monomeric units. For example, two sidechains can be attached to a maleic acid monomer.

In some embodiments, the plurality of sidechains corresponds to a number greater than 90% of the number of monomeric units of said polymer backbone.

In some embodiments, the plurality of platinum compounds corresponds to number between 10% and 100%, inclusive, of the number of monomeric units of said polymer backbone. Generally there is a one-to-one relationship between platinum compounds and monomeric subunits. Thus, the percent refers to the number of monomeric units that are linked to a platinum compound to the total number of monomeric units present in the polymer backbone.

In some embodiments, the plurality of platinum compounds corresponds to number between 25% and 75%, inclusive, of the number of monomeric units of said polymer backbone.

Generally from 10 to 500 ug of the platinum compound can be loaded on 1 mg of the polymer. Preferably, 50 to 250 ug, more preferably 150 to 200 ug of the platinum compound is loaded on 1 mg of the polymer. In some experiments, the inventors obtained a loading of 175±5 ug/mg of polymer.

In some embodiments, the sidechains comprise dicarboxylic acids. In some embodiments, the dicarboxylic acids are of the formula HOOC—R—COOH, wherein R is a C1-C6 alkyl, C2-C6 alkenyl, or C2-C6 alkynyl. In a preferred embodiment, the dicarboxylic acid is maleic acid.

In some embodiments, the copolymer comprises at least one monomer having the formula —CH($CO_2H$)—R—CH(C(O)R')—, wherein R is a bond, $C_1$-$C_6$ alkylene, where the alkylene can comprise one or more double or triple bonds; and R' is a substituted nitrogen atom. Preferably, R is a bond.

In some embodiments, between 50% to 100%, inclusive, of the monomeric subunits in the polymeric backbone are —CH($CO_2H$)—R—CH(C(O)R')—, wherein R is a bond, $C_1$-$C_6$ alkylene, where the alkylene can comprise one or more double or triple bonds; and R' is a substituted nitrogen atom.

In some embodiments, at least 90% or more of the monomeric subunits in the polymeric backbone are —CH($CO_2H$)—R—CH(C(O)R')—, wherein R is a bond, $C_1$-$C_6$ alkylene, where the alkylene can comprise one or more double or triple bonds; and R' is a substituted nitrogen atom.

In some embodiments, the copolymer comprises at least one monomer having the formula —CH($CO_2H$)—R—CH(C(O)R')$CH_2C(Me_2)$— or —CH(C(O)R')—R—CH($CO_2H$)—$CH_2C(Me_2)$—, wherein R is a bond, $C_1$-$C_6$ alkylene, where the alkylene can comprise one or more double or triple bonds; and R' is a substituted nitrogen atom. Preferably, R is a bond.

In some embodiments, the copolymer comprises between 50% to 100%, inclusive of monomers having the formula —CH($CO_2H$)—R—CH(C(O)R')$CH_2C(Me_2)$— or —CH(C(O)R')—R—CH($CO_2H$)—$CH_2C(Me_2)$—, wherein R is a bond, $C_1$-$C_6$ alkylene, where the alkylene can comprise one or more double or triple bonds; and R' is a substituted nitrogen atom.

In some embodiments, the copolymer comprises at least 90% of monomers having the formula —CH(CO$_2$H)—R—CH(C(O)R')CH$_2$C(Me$_2$)— or —CH(C(O)R')—R—CH(CO$_2$H)—CH$_2$C(Me$_2$)—, wherein R is a bond, C$_1$-C$_6$ alkylene, where the alkylene can comprise one or more double or triple bonds; and R' is a substituted nitrogen atom.

In some embodiments, R' is

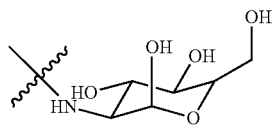

or —NH(CH$_2$CH$_2$O)$_m$CH$_3$, wherein m is 1-150.

In some embodiments, at least one monomer of the polymer comprises two sidechains selected from the group consisting of carboxylic acid, amide, and ester. Said sidechains being separated from each other by 1, 2, 3, 4, 5, 6, 7, 8, 9 or ten carbon, oxygen, nitrogen, sulfur atoms, or combination thereof. Preferably, said amide and ester sidechains are separated from each other by two carbon atoms. Preferably, at least one of the sidechains is not a carboxylic acid.

In some embodiments, at least one monomer of the polymer comprises two carboxylic acid sidechains. Said carboxylic acid sidechains being separated from each other by 1, 2, 3, 4, 5, 6, 7, 8, 9 or ten carbon, oxygen, nitrogen, sulfur atoms, or combination thereof. Preferably, said carboxylic acid sidechains are separated from each other by two carbon atoms. The said carbon atoms can be linked to each other through a single bond or a double bond.

In some embodiments, at least one monomer of the polymer comprises a carboxylic acid and an amide sidechains. Said carboxylic acid sidechains and amide sidechains being separated from each other by 1, 2, 3, 4, 5, 6, 7, 8, 9 or ten carbon, oxygen, nitrogen, sulfur atoms, or combination thereof. Preferably, said carboxylic acid and amide sidechains are separated from each other by two carbon atoms. The said carbon atoms can be linked to each other through a single bond or a double bond.

In some embodiments, at least one monomer of the polymer comprises a carboxylic acid and ester sidechains. Said carboxylic acid sidechains and ester sidechains being separated from each other by 1, 2, 3, 4, 5, 6, 7, 8, 9 or ten carbon, oxygen, nitrogen, sulfur atoms, or combination thereof. Preferably, said carboxylic acid and ester sidechains are separated from each other by two carbon atoms. The said carbon atoms can be linked to each other through a single bond or a double bond.

In some embodiments, at least one monomer of the polymer comprises an amide and ester sidechains. Said amide sidechains and ester sidechains being separated from each other by 1, 2, 3, 4, 5, 6, 7, 8, 9 or ten carbon, oxygen, nitrogen, sulfur atoms, or combination thereof. Preferably, said amide and ester sidechains are separated from each other by two carbon atoms. The said carbon atoms can be linked to each other through a single bond or a double bond.

In some embodiments, at least one monomer of the polymer comprises two amide sidechains. Said amide sidechains being separated from each other by 1, 2, 3, 4, 5, 6, 7, 8, 9 or ten carbon, oxygen, nitrogen, sulfur atoms, or combination thereof. Preferably, said amide and ester sidechains are separated from each other by two carbon atoms.

In some embodiments, at least one monomer of the polymer comprises two ester sidechains. Said ester sidechains being separated from each other by 1, 2, 3, 4, 5, 6, 7, 8, 9 or ten carbon, oxygen, nitrogen, sulfur atoms, or combination thereof. Preferably, said amide and ester sidechains are separated from each other by two carbon atoms.

In some embodiments, the polymer comprises two sidechains selected from the group consisting of carboxylic acid, amide, and ester. Said sidechains being separated from each other by 1, 2, 3, 4, 5, 6, 7, 8, 9 or ten carbon, oxygen, nitrogen, sulfur atoms, or combination thereof. Preferably, said amide and ester sidechains are separated from each other by two carbon atoms. Preferably, at least least one of the sidechains is not a carboxylic acid.

In some embodiments, the polymer comprises at least two carboxylic acid sidechains. Said carboxylic acid sidechains being separated from each other by 1, 2, 3, 4, 5, 6, 7, 8, 9 or ten carbon, oxygen, nitrogen, sulfur atoms, or combination thereof. Preferably, said carboxylic acid sidechains are separated from each other by two carbon atoms.

In some embodiments, the polymer comprises a carboxylic acid and an amide sidechains. Said carboxylic acid sidechains and amide sidechains being separated from each other by 1, 2, 3, 4, 5, 6, 7, 8, 9 or ten carbon, oxygen, nitrogen, sulfur atoms, or combination thereof. Preferably, said carboxylic acid and amide sidechains are separated from each other by two carbon atoms.

In some embodiments, the polymer comprises a carboxylic acid and an ester sidechains. Said carboxylic acid sidechains and ester sidechains being separated from each other by 1, 2, 3, 4, 5, 6, 7, 8, 9 or ten carbon, oxygen, nitrogen, sulfur atoms, or combination thereof. Preferably, said carboxylic acid and ester sidechains are separated from each other by two carbon atoms.

In some embodiments, the polymer comprises an amide and an ester sidechains. Said amide sidechains and ester sidechains being separated from each other by 1, 2, 3, 4, 5, 6, 7, 8, 9 or ten carbon, oxygen, nitrogen, sulfur atoms, or combination thereof. Preferably, said amide and ester sidechains are separated from each other by two carbon atoms. The said carbon atoms can be linked to each other through a single bond or a double bond.

In some embodiments, the polymer comprises two amide sidechains. Said amide sidechains being separated from each other by 1, 2, 3, 4, 5, 6, 7, 8, 9 or ten carbon, oxygen, nitrogen, sulfur atoms, or combination thereof. Preferably, said amide and ester sidechains are separated from each other by two carbon atoms.

In some embodiments, the polymer comprises two ester sidechains. Said ester sidechains being separated from each other by 1, 2, 3, 4, 5, 6, 7, 8, 9 or ten carbon, oxygen, nitrogen, sulfur atoms, or combination thereof. Preferably, said amide and ester sidechains are separated from each other by two carbon atoms.

The nanoparticles of the invention can range in size from 25-250 nm, preferably 50-200 nm, more preferably 80-160 nm, and most preferably 90-110 nm. Without wishing to be bound by theory, nanoparticles in the size range of 80-160 home preferentially into tumors resulting from the enhanced permeability and retention. See for example, Moghimi, et al., Pharmacol Rev. 2001 June; 53(2):283-318.

In some embodiments, the platinum compound is dissociably linked to said backbone through at least one coordination bond. Without wishing to be bound by theory, the coordination bond is more liable and thus releases the platinum compound more easily.

In some embodiments, linking of the platinum compound to the biopolymer backbone further comprises a carboxylato bond. In some embodiments, the platinum compound is linked to the backbone through a coordination bond and a carboxylato bond.

It is to be understood that although linkage to backbone is recited, one of skill in the art understands that the platinum compound is generally linked to one or more sidechains which themselves are linked to the backbone. So any recitation of linking of a platinum compound to backbone encompasses the situations where the platinum compound is linked to a sidechain which is then linked to the backbone.

In some embodiments, the coordination bond is between platinum atom of the platinum compound and an oxygen of the sidechain. Preferably the coordination bond is between platinum and a carbonyl oxygen.

In some embodiments, the coordination bond is between platinum atom of the platinum compound and an amide oxygen of the sidechain. In some embodiments, the coordination bond is between platinum atom of the platinum compound and an ester carbonyl oxygen of the sidechain.

In some embodiments, the copolymer comprises at least one maleic acid monomer, wherein at least one carboxylic acid of said at least maleic acid is derivatized to an amide.

In some embodiments, between 50% to 100%, inclusive, of the monomeric units in the polymer backbone are maleic acid monomer and wherein at least one carboxylic acid of said maleic acid monomer is derivatized to an amide.

In some embodiments, at least 90% of the monomeric units in the polymer backbone are maleic acid monomer and wherein at least one carboxylic acid of said maleic acid monomer is derivatized to an amide.

The loading of platinum compound onto the polymer can be represented by as percent mg of platinum compound per mg of polymer. For example, a maximum of 0.375 mg of cisplatin can be loaded onto the PIMA-GA polymer therefore a loading of 37.5% represents the maximum loading for that particular polymer. The loading can range from about 1% to the theoretical total loading for a polymer.

In some embodiments, the platinum compound loading is from 1%-37.5%. The percent loading represent mg of platinum compound linked with per mg of polymer.

In some embodiments, the platinum compound loading is from 1%-6%. In some embodiments, the Pt(II) compound loading is from 0.01% to 1°0%.

Another aspect of the invention is directed to biocompatible conjugated polymer nanoparticles including a poly(isobutylene-alt-maleic acid) backbone. The backbone consists of from 25 to 50 monomers. Also included are a plurality of PEG sidechains covalently linked to said backbone. The PEG sidechains have a molecular weight of from 1000 to 3000 Dalton. The PEG sidechains number between 50% and 100%, inclusive, of the number of monomeric units of the polymer backbone. Also included are a plurality of cisplatin side groups dissociably linked to the backbone. The cisplatin side groups number between 25% and 75%, inclusive, of the number of monomeric units of the polymer backbone.

Yet another aspect of the invention is directed to biocompatible conjugated polymer nanoparticles including a poly(isobutylene-alt-maleic acid) backbone. The backbone consist of 40 monomers. Also included are a plurality of PEG sidechains covalently linked to the backbone. The PEG sidechains have a molecular weight of 2000 Dalton. The PEG sidechains number greater than 90% of monomeric units of said polymer backbone. Also included are a plurality of cisplatin side groups dissociably linked to the backbone. The cisplatin side groups number between 25% and 75%, inclusive, of the number of monomeric units of the polymer backbone.

Still another aspect of the invention is directed to biocompatible conjugated polymer nanoparticles including a poly(isobutylene-alt-maleic acid) backbone. The backbone consists of from 25 to 50 monomers. Also included are a plurality of glucosamine sidechains covalently linked to said backbone. The glucosamine sidechains number between 50% and 100%, inclusive, of monomeric units of said polymer backbone. Also included are a plurality of cisplatin side groups dissociably linked to the backbone. The cisplatin side groups number between 25% and 75%, inclusive, of the number of monomeric units of the polymer backbone.

Another aspect of the invention is directed to biocompatible conjugated polymer nanoparticles including a poly(isobutylene-alt-maleic acid) backbone. The backbone consists of from 25 to 50 monomers. Also included are a plurality of glucosamine sidechains covalently linked to said backbone. The glucosamine sidechains number greater than 90% of monomeric units of said polymer backbone. Also included are a plurality of cisplatin side groups dissociably linked to the backbone. The cisplatin side groups number between 25% and 75%, inclusive, of the number of monomeric units of the polymer backbone.

Yet another aspect of the invention is directed to carboxylic acid-platinum compound complex conjugated nanoparticles including a carboxylic acid-platinum compound complex and a plurality of lipid-polymer chains. The carboxylic acid portion of said carboxylic acid-platinum complex is covalently bound to said lipid-polymer chains.

In a preferred embodiment, the carboxylic acid is maleic acid. In some embodiments, the polymer is PEG.

In certain embodiments, the platinum compound loading is from 1%-37.5%. In certain embodiments, the platinum compound loading is from 1%-6%.

The platinum compound can be Pt(II) compound or a Pt(IV) compound. In some embodiments, the Pt(II) compound is selected from the group consisting of cisplatin, oxaliplatin, carboplatin, paraplatin, sartraplatin, and combinations thereof. In a preferred embodiment, the Pt(II) compound is cisplatin.

Another aspect of the invention is directed to a vesicle, micelle, or liposome compound comprising a plurality of nanoparticles of claim as described herein.

Still another aspect of the invention is directed to a pharmaceutical composition including any of the nanoparticles or compounds described herein and a pharmaceutically acceptable carrier.

Yet another aspect of the invention is directed to a method of treating cancer or metastasis. The method includes selecting a subject in need of treatment for cancer or metastasis and administering to the subject an effective amount of any of the nanoparticles, compounds, or compositions described herein.

In some embodiments, the cancer or metastasis is selected from the group consisting of platinum susceptible or resistant tumors including breast, head and neck, ovarian, testicular, pancreatic, oral-esophageal, gastrointestinal, liver, gall bladder, lung, melanoma, skin cancer, sarcomas, blood cancers, brain tumors including glioblastomas, and tumors of neuroectodermal origin.

In yet another aspect, the invention provide for methods of formulating platinum compound polymer nanoparticles, method comprising conjugation of platinum compound with a biocompatible polymer or biocompatible copolymer. Without wishing to be bound by theory, conjugation of platinum compound with the biocompatible polymer at acidic pH results in nanoparticles that are more active in vivo than when conjugation is done at basic pH.

Accordingly, in some embodiments, conjugation is done at pH below 7, preferably a pH between 1 and 6.9. In some more preferred embodiments, conjugation is carried out at a pH of 6.5.

The inventors have observed that conjugation under basic conditions favor the formation of an isomeric PIMA-GA_Cisplantin complex with a monocarboxylato and a more stable Pt<->N coordinate bond. In contrast, complexation PIMA-GA and cisplatin in an acidic pH generates the isomeric state characterized by the monocarboxylato bond and Pt<->O coordinate bond. Thus, conjugations conditions that lead to the formation of a Pt<->O coordinate bond over a Pt<->N coordinate bond are preferred for conjugation.

Generally an excess of the Pt(II) compound to the polymer is used. In some embodiments, 5-25 mole access of Pt(II) compound to polymer is used. Preferably 10-20 mole access of platinum(II) compound to polymer is used. In one preferred 15 mole access of Pt(II) compound to polymer is used.

In yet another aspect, the invention provides a dicarbonyl molecule linked to a lipid molecule. Such a compound can be represented by the structure lipid-linker-dicarbnoyl. These molecules can be used to complex platinum compounds such as cisplatin, oxaliplatin or other platinates and platinum compounds described herein through carboxylato-linkage and/or coordination bonds. These can then be mixed with appropriate lipids/phospholipids to nanoparticles of less than 150 nm, which release Pt in a pH-dependent manner. Once formulated these nanoparticles exhibit improved efficacy and toxicity profile as compared with carboplatin and cisplatin, and are active in a cisplatin-resistant cancer.

These nanoparticles can be formulated to comprise pharmaceutically active agents for delivery.

The term "Lipid" is used in the conventional sense to refer to molecules that are soluble to a greater or lesser degree in organic solvents, like alcohols, and relatively insoluble in aqueous media. Thus, the term "lipid" includes compounds of varying chain length, from as short as about 2 carbon atoms to as long as about 28 carbon atoms. Additionally, the compounds may be saturated or unsaturated. and in the form of straight- or branched-chains or in the form of unfused or fused ring structures. Exemplary lipids include, but are not limited to, fats, waxes, sterols, steroids, bile acids, fat-soluble vitamins (such as A, D, E, and K), monoglycerides, diglycerides, phospholipids, glycolipids, sulpholipids, aminolipids, chromolipids (lipochromes), glycerophospholipids, sphingolipids, prenol lipids, saccharolipids, polyketides, and fatty acids. In some embodiments, the lipid is cholesterol or distearoylphosphatidylethanolamine.

Generally any molecule that has two carbonyl groups can be used. In some embodiments, the dicarbonyl molecule is a dicarboxylic acid, or a keto-carboxylic acid. In some preferred embodiments, the dicarbonyl molecule is succinic acid.

In some embodiments, the dicarbonyl molecule is R'OC(O)—R—C(O)—, where R is $C_1$-$C_6$ alkylene, where the alkylene can comprise one or more double or triple bonds and/or the backbone of the alkylene can be interrupted with one or more of O, S, S(O), $SO_2$, NH, C(O); and R' is H, alkyl, alkenyl, alkynyl, aryl, heteroaryl, acylcy, heterocyclyl, each of which can be optionally substituted. Preferably R is $CH_2$, —$CH_2CH_2$—, —$CH_2CH_2$—$CH_2$— or —CH=CH—. Preferably R' is H.

The dicarbonyl molecule can be linked with the lipid molecule directly or through a linker molecule. The term "linker" means an organic moiety that connects two parts of a compound. Linkers typically comprise a direct bond or an atom such as oxygen or sulfur, a unit such as NH, C(O), C(O)NH, SO, $SO_2$, $SO_2$NH or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, al kenylheteroarylalkenyl, alkenylheteroarylal kynyl, alkynylheteroarylal kyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, where one or more methylenes can be interrupted or terminated by O, S, S(O), $SO_2$, NH, C(O). It is to be understood that the diacarbonyl molecule and/or the lipid can be modified to comprise functional groups for linking to each other or to the linker.

In some embodiments, linker is a diamine such as ethylene diamine. In some embodiments, linker is PEG-$NH_2$.

In one preferred embodiment, linker is —$NHCH_2CH_2C(O)$—. In another preferred embodiment, linker is —$CH_2CH_2NHC(O)$—$[OCH_2CH_2]_z$—NH—, where z is 1-50. Preferably z is 45.

Figure 10:
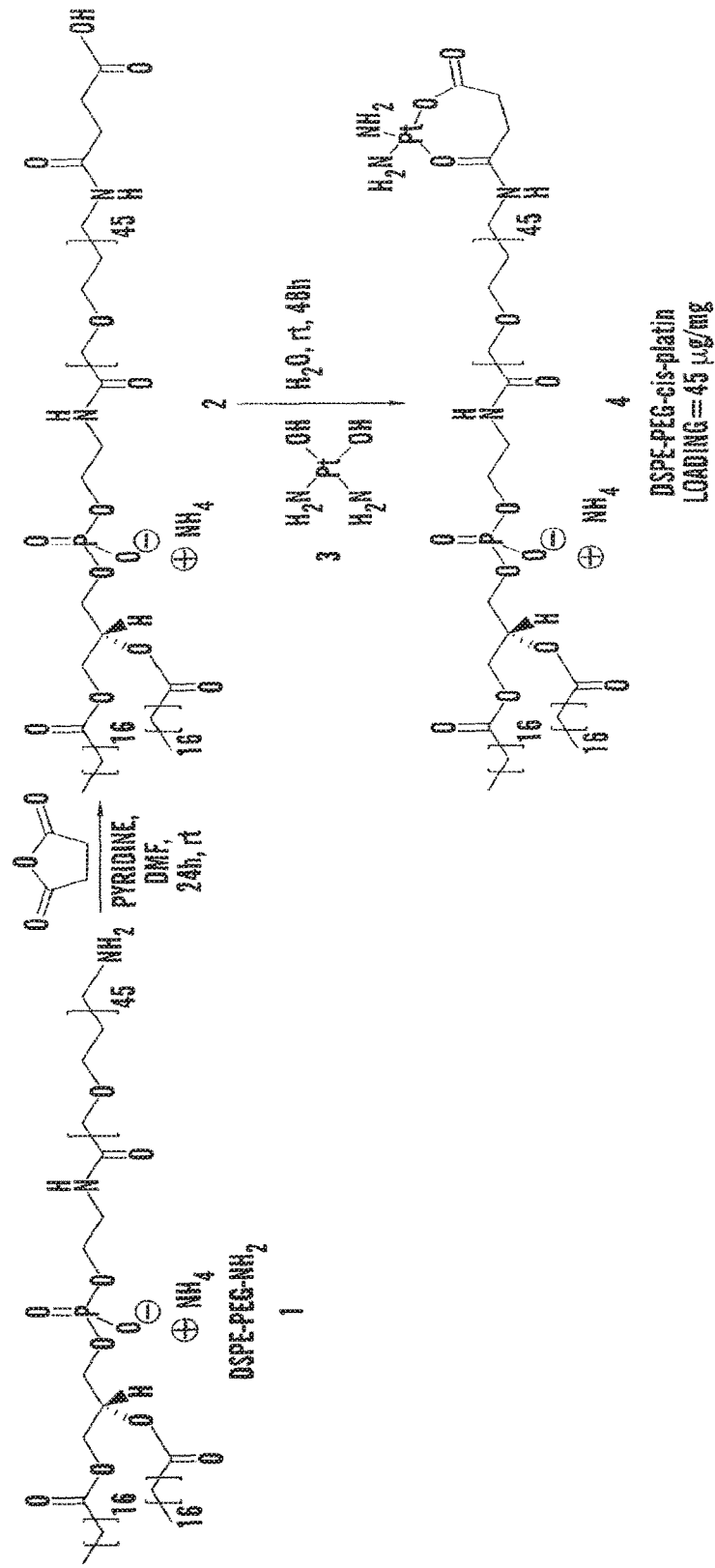
FIG. 10 is a scheme showing synthesis of lipid maleic acid-cipslatin complex, which can form micelles in water.

In some embodiments, the lipid-dicarbonyl compound is as shown in FIGS. 10 (compound 2) and 25A (compound 5).

In another aspect, the invention provide a biocompatible polymer comprising at least one monomer having the formula —$CH(CO_2H)$—R—$CH(C(O)R')$—, wherein R is a bond, $C_1$-$C_6$ alkylene, where the alkylene can comprise one or more double or triple bonds; and R' is a substituted nitrogen atom. Preferably, R is a bond.

In some embodiments, the polymer comprises from 2 to 100 monomeric units having the formula —$CH(CO_2H)$—R—$CH(C(O)R')$—, wherein R is a bond, $C_1$-$C_6$ alkylene, where the alkylene can comprise one or more double or triple bonds; and R' is a substituted nitrogen atom.

In some embodiments, the polymer comprises from 25 to 50 monomeric units having the formula —$CH(CO_2H)$—R—$CH(C(O)R')$—, wherein R is a bond, $C_1$-$C_6$ alkylene, where the alkylene can comprise one or more double or triple bonds; and R' is a substituted nitrogen atom.

In some embodiments, between 500/% to 100%, inclusive, of the monomeric subunits in the polymeric backbone are —$CH(CO_2H)$—R—$CH(C(O)R')$—, wherein R is a bond, $C_1$-$C_6$ alkylene, where the alkylene can comprise one or more double or triple bonds; and R' is a substituted nitrogen atom.

In some embodiments, at least 90% or more of the monomeric subunits in the polymeric backbone are —$CH(CO_2H)$—R—$CH(C(O)R')$—, wherein R is a bond, $C_1$-$C_6$ alkylene, where the alkylene can comprise one or more double or triple bonds; and R' is a substituted nitrogen atom.

In some embodiments, the copolymer comprises at least one monomer having the formula —$CH(CO_2H)$—R—$CH(C(O)R')CH_2C(Me_2)$— or —$CH(C(O)R')$—R—CH (CO₂H)—CH₂C(Me₂)-, wherein R is a bond, $C_1$-$C_6$ alkylene, where the alkylene can comprise one or more double or triple bonds; and R' is a substituted nitrogen atom. Preferably, R is a bond.

In some embodiments, the copolymer comprises between 50% to 100%, inclusive of monomers having the formula —CH(CO₂H)—R—CH(C(O)R')CH₂C(Me₂)— or —CH(C(O)R')—R—CH(CO₂H)—CH₂C(Me₂)—, wherein R is a bond, $C_1$-$C_6$ alkylene, where the alkylene can comprise one or more double or triple bonds; and R' is a substituted nitrogen atom.

In some embodiments, the copolymer comprises at least 90% of monomers having the formula —CH(CO₂H)—R—CH(C(O)R')CH₂C(Me₂)— or —CH(C(O)R')—R—CH(CO₂H)—CH₂C(Me₂)—, wherein R is a bond, $C_1$-$C_6$ alkylene, where the alkylene can comprise one or more double or triple bonds; and R' is a substituted nitrogen atom.

In some embodiments, R' is

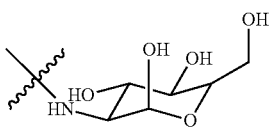

or —NH(CH₂CH₂O)$_m$CH₃, wherein m is 1-150.

These polymers can be used for formulating nanoparticles and gels which can be used for drug delivery. Thus, the invention also provides nanoparticles comprising a polymer described herein and one or more bioactive active agent ("bioactive agent").

Compositions described herein can be used in methods for sustained release of bioactive active agents. In one embodiment, the method comprising: (a) providing or administering to a subject a composition described herein, wherein the composition contains the bioactive agent. As used herein, "bioactive agents" refer to naturally occurring biological materials, for example, extracellular matrix materials such as fibronectin, vitronection, and laminin; cytokins; and growth factors and differentiation factors. "Bioactive agents" also refer to artificially synthesized materials, molecules or compounds that have a biological effect on a biological cell, tissue or organ.

Suitable growth factors and cytokines include, but are not limited, to stem cell factor (SCF), granulocyte-colony stimulating factor (G-CSF), granulocyte-macrophage stimulating factor (GM-CSF), stromal cell-derived factor-1, steel factor, VEGF, TGFβ, platelet derived growth factor (PDGF), angiopoietins (Ang), epidermal growth factor (EGF), bFGF, HNF, NGF, bone morphogenic protein (BMP), fibroblast growth factor (FGF), hepatocye growth factor, insulin-like growth factor (IGF-1), interleukin (IL)-3, IL-1α, IL-1β, IL-6, IL-7, IL-8, IL-11, and IL-13, colony-stimulating factors, thrombopoietin, erythropoietin, flt3-ligand, and tumor necrosis factor α (TNFα). Other examples are described in Dijke et al., "Growth Factors for Wound Healing", Bio/Technology, 7:793-798 (1989); Mulder G D, Haberer P A, Jeter K F, eds. Clinicians' Pocket Guide to Chronic Wound Repair. 4th ed. Springhouse, Pa.: Springhouse Corporation; 1998:85; Ziegler T. R., Pierce, G. F., and Herndon, D. N., 1997, International Symposium on Growth Factors and Wound Healing: Basic Science & Potential Clinical Applications (Boston, 1995, Serono Symposia USA), Publisher: Springer Verlag.

In some embodiments, suitable bioactive agents include but not limited to therapeutic agents. As used herein, the term "therapeutic agent" refers to a substance used in the diagnosis, treatment, or prevention of a disease. Any therapeutic agent known to those of ordinary skill in the art to be of benefit in the diagnosis, treatment or prevention of a disease is contemplated as a therapeutic agent in the context of the present invention. Therapeutic agents include pharmaceutically active compounds, hormones, growth factors, enzymes, DNA, plasmid DNA, RNA, siRNA, viruses, proteins, lipids, pro-inflammatory molecules, antibodies, antibiotics, anti-inflammatory agents, anti-sense nucleotides and transforming nucleic acids or combinations thereof. Any of the therapeutic agents may be combined to the extent such combination is biologically compatible.

Exemplary therapeutic agents include, but are not limited to, those found in *Harrison's Principles of Internal Medicine*, 13th Edition, Eds. T. R. Harrison et al. McGraw-Hill N.Y., NY; Physicians Desk Reference, 50th Edition, 1997, Oradell New Jersey, Medical Economics Co.; Pharmacological Basis of Therapeutics, 8th Edition, Goodman and Gilman, 1990; United States Pharmacopeia, The National Formulary, USP XII NF XVII, 1990; current edition of Goodman and Oilman's *The Pharmacological Basis of Therapeutics*; and current edition of *The Merck Index*, the complete contents of all of which are incorporated herein by reference.

Examples of therapeutic agents which may be incorporated in the composition, include but are not limited to, narcotic analgesic drugs; salts of gold; corticosteroids; hormones; antimalarial drugs; indole derivatives; pharmaceuticals for arthritis treatment; antibiotics, including Tetracyclines, Penicillin, Streptomycin and Aureomycin; antihelmintic and canine distemper drugs, applied to domestic animals and large cattle, such, as, for example, phenothiazine; drugs based on sulfur, such, as sulfioxazole; antitumor drugs; pharmaceuticals supervising addictions, such as agents controlling alcohol addiction and agents controlling tobacco addiction; antagonists of drug addiction, such, as methadone; weightcontrolling drugs; thyroid gland controlling drugs; analgesics; drugs controlling fertilization or contraception hormones; amphetamines; antihypertensive drugs; antiinflammatories agents; antitussives; sedatives; neuromuscular relaxants; antiepileptic drugs; antidepressants; antidisrhythmic drugs; vasodilating drugs; antihypertensive diuretics; antidiabetic agents; anticoagulants; antituberculous agents; antipsyhotic agents; hormones and peptides. It is understood that above list is not full and simply represents the wide diversification of therapeutic agents that may be included in the compositions. In some embodiments, therapeutic agent is Mitoxantrone, protein (e.g. VEGF) or plasmid DNA.

The amount of therapeutic agent distributed in a composition depends on various factors including, for example, specific agent; function which it should carry out; required period of time for release of a the agent; quantity to be administered. Generally, dosage of a therapeutic agent i.e. amount of therapeutic agent in composition, is selected from the range about from 0.001% (w/w) up to 95% (w/w), preferably, from about 5% (w/w) to about 75% (w/w), and, most preferably, from about 10% (w/w) to about 60% (w/w).

Cisplatin [cis-dichlorodiammineplatinum(II)] (CDDP) has emerged as an important class of antitumor agents, and is widely used for the treatment of many malignancies including testicular, ovarian, cervical, head and neck, and non-small cell lung cancer (Jamieson, et al, Chem. Rev. (1999), 99(9): 2467-2498). It was also shown to be active in triple negative breast cancer (Leong, et al., J. Clin. Invest. (2007), 117(5): 1370-80). Its use is however dose-limited mainly because of nephrotoxicity or toxicity to the kidney (Madias, N E and Harrington, J T, Am. J. (1978), 65(2): 307-14). To address this limitation, two directions of research has evolved, the first focused on the synthesis of platinum analogues, the second is to engineer novel nanodelivery systems as a mean to target the drug directly to the tumor site. It is now well established that nanoparticles in the size range 80-120 nm home preferentially into tumors resulting from the enhanced permeability and retention (EPR) effect (Moghimi, et al., Pharmacol. Rev. (2001), 53(2): 283-318). This can reduce systemic side effects and exhibit increased intratumoral delivery. A nanoliposomal formulation of cisplatin was found to deliver 50-200 times more drug to the tumor as compared to administration of free cisplatin (Harrington, et al. Ann. Oncol. (2001) 12: 493-496). Although there was minimal toxicity with the nanoliposomal formulation, it had only modest antitumor activity as compared to cisplatin; reflecting the challenges of not only delivering platinum in a relatively inactive form, but the subsequent need to achieve significant release and activation within the tumor. A second strategy of encapsulating cisplatin into polymeric systems has been a challenge as a result of its insolubility in organic solvents and partial solubility in water, which resulted in poor loading or inability to maintain sustained release. This has required the development of platinum (IV) prodrugs that can be modified to increase hydrophobicity, and increase loading in polylactide-polyglycolide copolymer nanoparticles (Dhar et al., 2009). Alternatively, cisplatin was conjugated to N-(2-hydroxypropyl) methacrylamide (HPMA) through peptidyl side-chains, and were shown to be biologically active (Lin X, Zhang Q, Rice J R, Stewart D R, Nowotnik D P, Howell S B. Improved targeting of platinum chemotherapeutics. The antitumour activity of the HPMA copolymer platinum agent AP5280 in murine tumour models. Eur J Cancer. 2004 January; 40(2):291-7). However, such approaches require processing through enzymatic cleavage or intracellular reduction for activation of the drug. Similarly, a PAMAM dendrimers-platinum complex, which increased drug loading, was found to be 200-550-fold less toxic than cisplatin as a result of strong bonds that are formed between the polymer and Pt (Haxton K J, Burt H M. Polymeric drug delivery of platinum-based anticancer agents. J Pharm Sci. 2009 July; 98(7):2299-316).

Figure 1B:
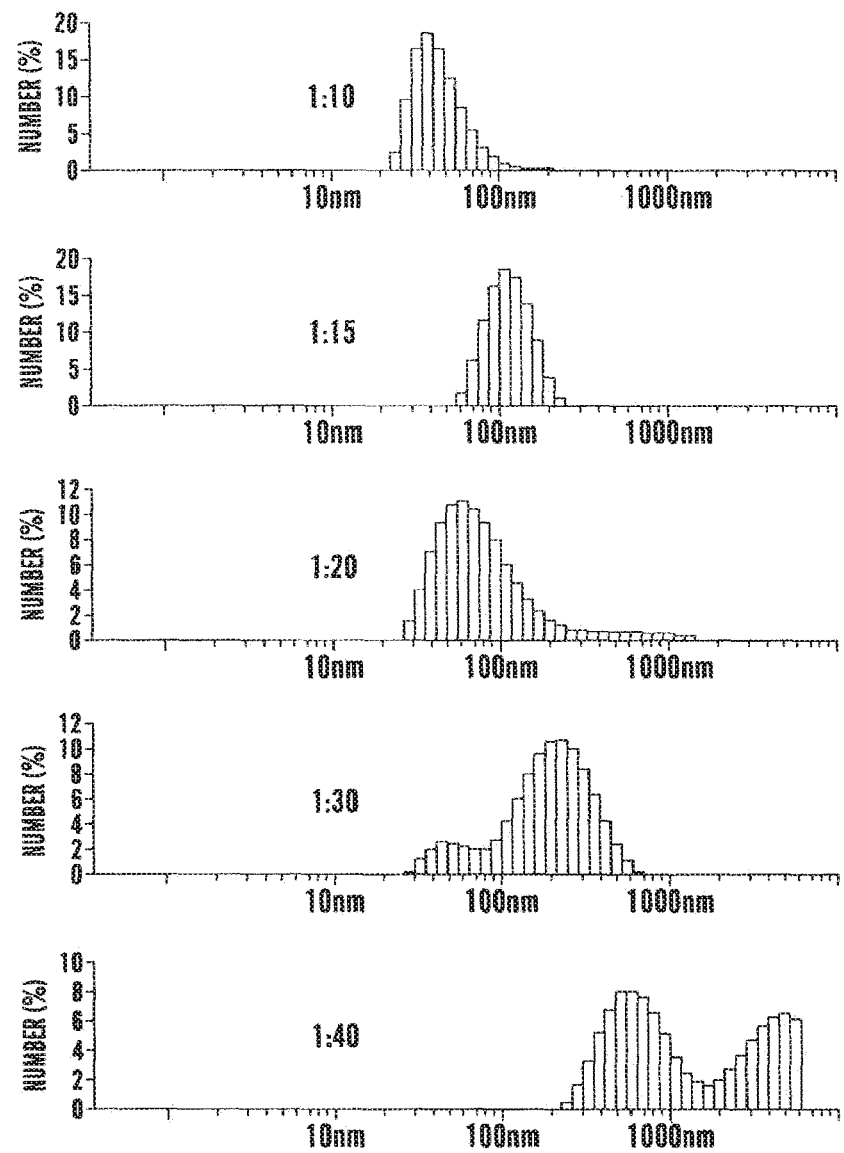
FIG. 1B shows that loading of different numbers of cisplatin per polymer affects the size of the nanoparticles as measured using DLS or TEM.

To engineer a nanoformulation of cisplatin that is facile but overcomes the challenges associated with current approaches, the inventors integrated the existing information on the biotransformation of cisplatin and understanding of the structure activity relationship that has emerged through the development of cisplatin analogues. Cisplatin gets activated through intracellular aquation of one of the two chloride leaving groups to form $[Pt(NH_3)_2Cl(OH_2)]^+$ and $[Pt(NH_3)_2(OH_2)]^{2-}$, following which the Pt forms covalent bonds to the $N_7$ position of purine bases to form intrastrand and interstrand crosslinks (Huifang Huang, Leiming Zhu, Brian R. Reid, Gary P. Drobny, Paul B. Hopkins. Solution Structure of a Cisplatin-Induced DNA Interstrand Cross-Link. *Science* 1995: 270. 1842-1845). In comparison, carboplatin and oxaloplatin, have a cyclobutane-1, 1-decarboxylate and an oxalate respectively as the leaving groups, which chelate the platinum more strongly thus conferring greater stability to the leaving group-PT complex and as a result exhibit fewer side effects than cisplatin but also lower efficacy than cisplatin (Richard J. Knox, Frank Friedlos, David A. Lydall and John J. Roberts Mechanism of Cytotoxicity of Anticancer Platinum Drugs: Evidence That cis-Diamminedichloroplatinum(II) and cis-Diammine-(1,1-cyclobutanedicarboxylato) platinum(II) Differ Only in the Kinetics of Their Interaction with DNA. *Cancer Research* 46, 1972-1979, Apr. 1, 1986; and Ronald S. Go, Alex A. Adjei. Review of the Comparative Pharmacology and Clinical Activity of Cisplatin and Carboplatin. *Journal of Clinical Oncology*, Vol 17, Issue 1 (January), 1999: 409). The inventors selected a 40-mer Poly(isobutylene-alt-maleic acid) (PIMA or PMA) as the polymer because each monomer exhibits dicarboxylato groups that can be complexed with cisplatin(OH)$_2$. allowed the loading of a cisplatin molecule. Furthermore, hydrogenation of maleic acid generates succinic acid, which is a component of the Krebs cycle. Poly(isobutylene-alt-maleic acid) 2 was synthesized from Poly(isobutylene-alt-maleic anhydride) 1 by reaction with water in DMF in one step as shown in FIG. 1. Further conjugation of cisplatin to Poly(isobutylene-alt-maleic acid) (PIMA) 2 was achieved by stirring hydrated cisplatin for 48 hours gave PMA-Cisplatin 6. The non-conjugated cisplatin was removed by dialysis and amount of loading was determined by NMR and spectrophotometry. Interestingly, the complexation process led to the generation of nanoparticles through a self-assembly process, with the size defined by the number of cisplatin molecules loaded per polymer. Measurement using dynamic laser light scatter revealed that saturating all the complexation sites with cisplatin resulted in a gel formation while loading 15 molecules of cisplatin per polymer resulted in a nanoparticle in the size range of 100 nm. This was validated by transmission electron microscopy (data not shown).

Figure 1C:
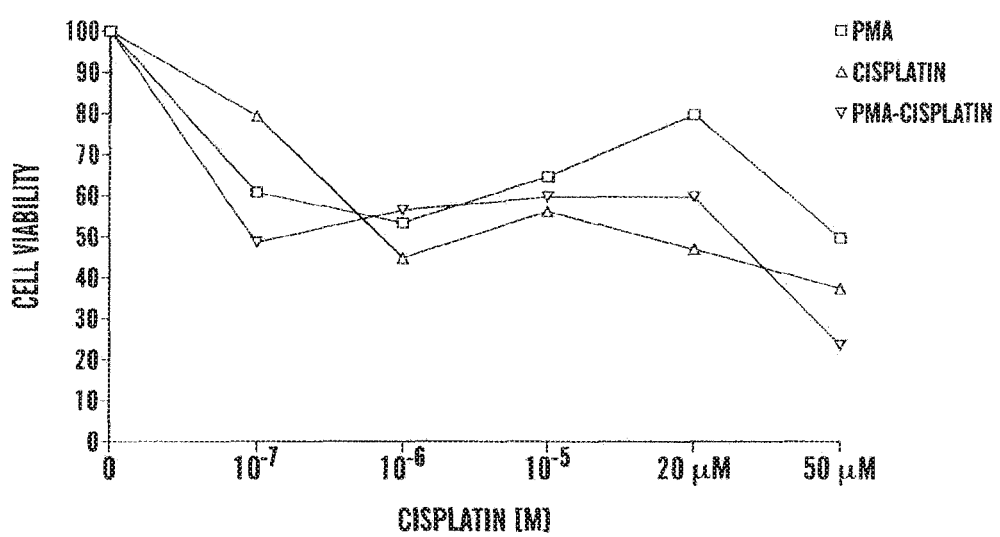
FIG. 1C shows a graph of Cytotoxicity study of Polyisobutylene maleic acid carrier (PIMA) 2 and conjugate (PIMA-CISPLATIN) (6).
Figure 2:
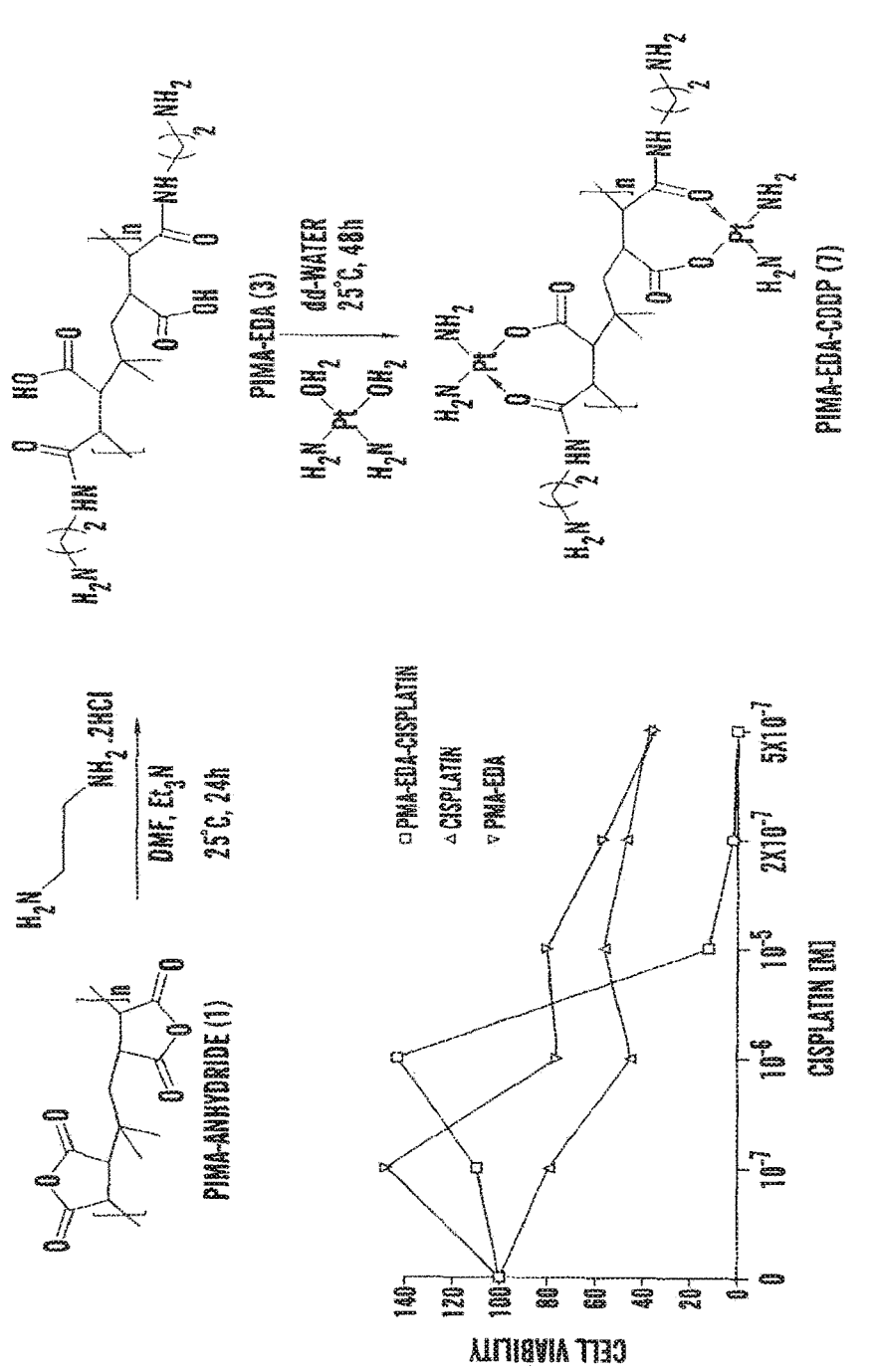
FIG. 2 shows a scheme showing derivatization of PMA with EDA. The derivatized polymer was used to synthesize the cisplatin-complex. The graph shows the effect of different treatments on LLC viability following 48 hours of incubation.
Figure 3:
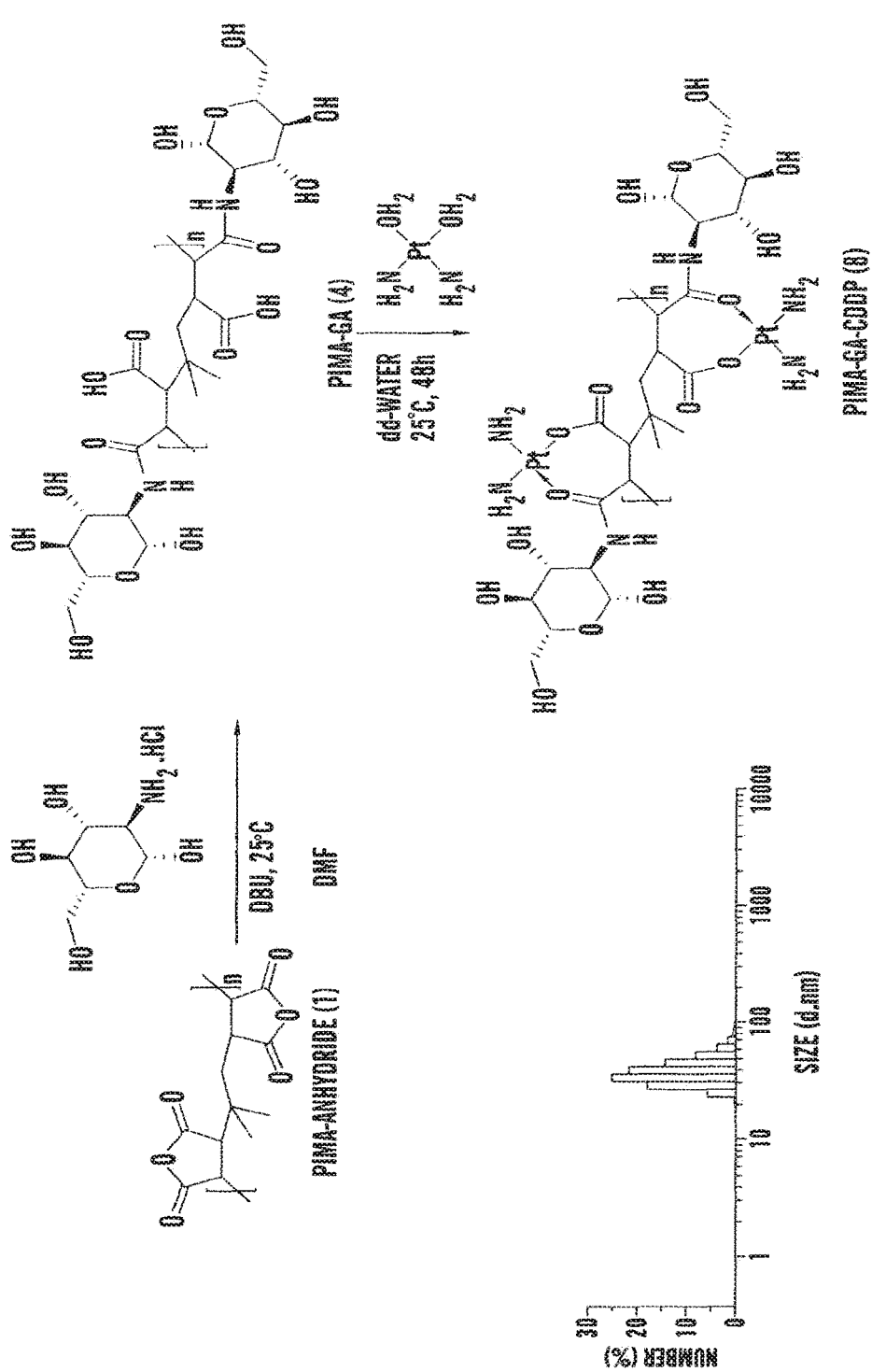
FIG. 3 shows a scheme of the synthesis of PMA-GA-Cisplatin. Complexation with cisplatin was carried out over a 48 hour period. This resulted in the formation of nanoparticles in the size range of around 100 nm as seen from the DLS measurements.
Figure 11A:
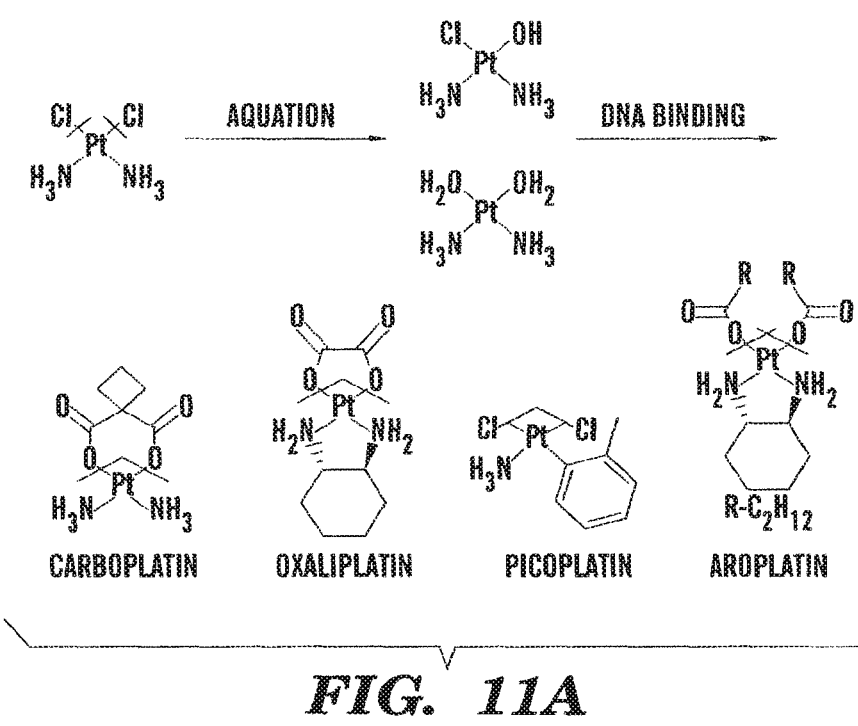
FIGS. 11A and 11B are schematics showing SAR-inspired engineering of a cisplatin nanoparticle.
Figure 11B:
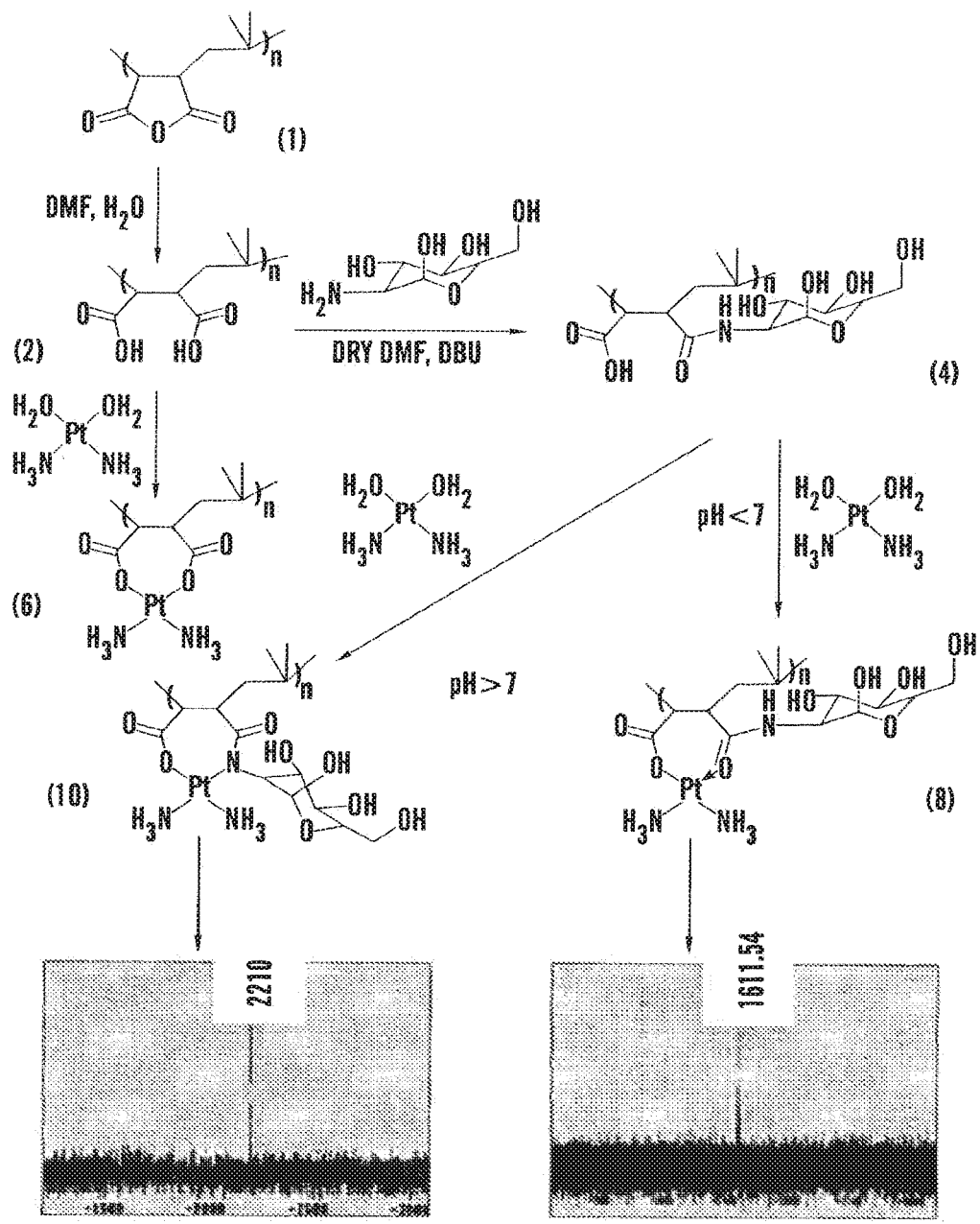

Cisplatin is a first line therapy for lung cancer, and as a result the inventors studied the effect of PMA-Cisplatin on the viability of Lewis lung cancer cells. Treatment with both cisplatin and PMA-cisplatin induced identical cell kill (FIG. 1C). However, PMA also induced tumor cell death. The inventors discovered that this can be overcome through derivatization of PMA. The inventors derivatized the polymer with ethylene diamine under basic conditions (FIG. 2). Interestingly, although the derivatization failed to remove the cytotoxicity of PMA, it increased the cytotoxicity of the PMA-cisplatin complex. This could potentially arise from the fact that the leaving group is less tightly bound as compared to underivatized PMA. Indeed, such an effect has been seen in the case of carboplatin, which has a lower rate constant for aquation than cisplatin, and as a result is also less cytotoxic. The native PMA-cisplatin may be tightly held as compared with PMA-EDA because of strong chelation formed by two carboxy groups. To further make the polymer more biocompatible the inventors modified the polymer with glucosamine (GA). PMA-GA-cisplatin was synthesized starting with PMA (1) by reacting with Glucosamine and then with aqueous cisplatin (FIGS. 3 and 11B). All the carrier polymers synthesized were platinated in aqueous phase at room temperature 25° C. for 2 days, with aquated cisplatin as platination agent, giving conjugates. At different time points, the inventors aliquoted out a small fraction and quantified the total loading of cisplatin on the polymer. The inventors observed a loading efficiency of ~60% by 5 hours of complexation, ~80% by 30 hours and 100% by 48 hours of platination. The total drug loaded was 6 mg/15 mg of polymer. Aquation of cisplatin was achieved using equimolar cisplatin and AgNO$_3$ under dark for 48 h. All carriers were routinely fractionated by dialysis and isolated by freeze-drying for spectroscopic characterization. Using DBU resulted in the synthesis of the glucosamine-PMA conjugate as seen in the distinct polymer and sugar peaks in the NMR results that matches with the predicted NMR values. However, treatments with bases, triethylamine or DIPEA, failed to give the predicted product, but the NMR traces provided valuable clue to defining the final functional product.

Figure 4B:
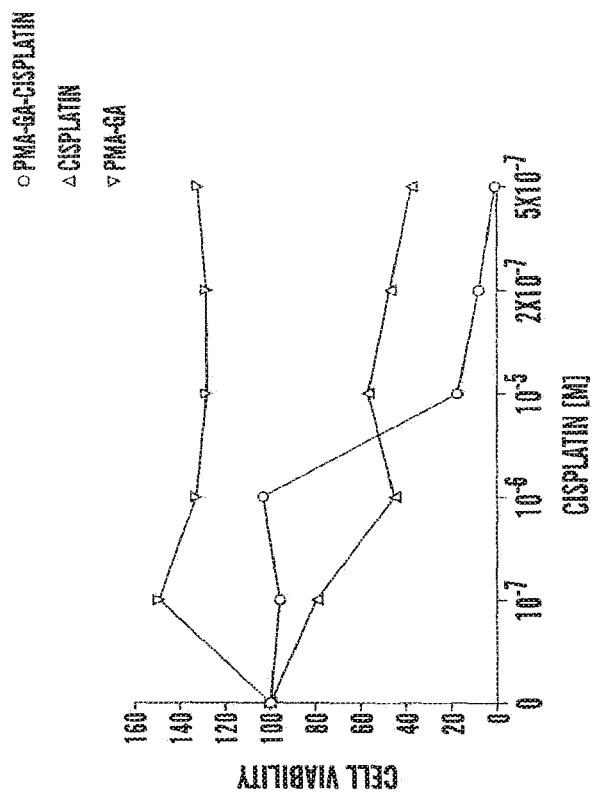
FIG. 4B is a concentration-effect graph showing the effect of different treatments on the viability of Lewis Lung Carcinoma cells when incubated with the active agents for 48 hours. Cell viability was measured using an MTS assay.

Complexation of cisplatin with PMA-GA resulted in the self assembly of the complex into nanoparticles. In certain cases, passing the nanoparticles through a 0.22 micron filter resulted in the generation of nanoparticles that were in the sub 100 nm range, which is critical for the particles to home in specifically to the tumor using the EPR effect. Interestingly, cell viability studies revealed that the PMA-GA derivative was devoid of any inherent toxicity to the cells. In contrast, it retained the efficacy of the aquated Cisplatin (FIG. 4B). Furthermore, derivatization of PMA with polyethylene glycol also removed the inherent toxicity associated with PMA. Additionally, the same goal can be achieved by conjugating maleic acid to a polymeric backbone that is biocompatible.

Figure 4A:
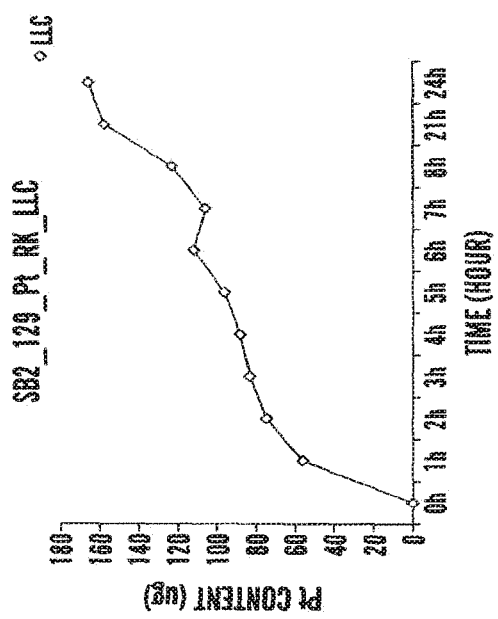
FIG. 4A is a graph showing the amount of active cisplatin that is released from the PMA-GA-Cisplatin nanoparticle when incubated with LLC lysate.

The increased efficacy with the derivatized chelated polymers as compared with the native polymer indicates that the monocarboxylato-chelated release drug much easily and showed superior activity over dicarboxylato-chelated (6). The inventors discovered that the polymeric monocarboxylato-chelated platinum compounds represent a sizeable advantage over the conjugates in which the metal is bound via dicarboxylic acid. Smooth hydrolytic drug liberation from the carrier in the monocarboxylato-chelated derivatized PMA conjugates, as compared to the more retarded hydrolytic fission of the dicarboxylato-chelated in PMA, may explain this enormous difference in cell killing performance. To study this further, the inventors incubated the drug-polymer conjugate with Lewis Lung Cancer cell lysate in a dialysis chamber, and quantified the release of free drug using a calorimetric assay. The inventors obtained a rapid and sustained release of the active agent (FIG. 4A). It should be noted that the same formulation had been dialyzed in water for 48 hours to remove any free cisplatin and the inventors had obtained 100% loading efficiency, suggesting that the active agent is not released in neutral conditions but is rapidly released in the presence of tumor cell lysate.

The compositions described herein can be formulated into gels and used for sustained released delivery of bioactive agents at specific locations in a subject. For example, the composition can be used for sustained release delivery of platinum compounds at site of tumors. In some embodiments, the composition is used for sustain delivery of a platinum compound after a tumor has been removed.

Pharmaceutical Compositions

For administration to a subject, the polymer linked platinum compound can be provided in pharmaceutically acceptable compositions. These pharmaceutically acceptable compositions comprise a therapeutically-effective amount of one or more of the platinum compounds described herein, formulated together with one or more pharmaceutically acceptable carriers (additives) and/or diluents. As described in detail below, the pharmaceutical compositions of the present invention can be specially formulated for administration in solid or liquid form, including those adapted for the following: (1) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. Additionally, compounds can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. Nos. 3,773,919; and 35 3,270,960.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alchols, such as ethanol; and (23) other nontoxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment. For example, an amount of a compound administered to a subject that is sufficient to produce a statistically significant, measurable change in at least one symptom of cancer or metastasis.

Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents.

As used herein, the term "administer" refers to the placement of a composition into a subject by a method or route which results in at least partial localization of the composition at a desired site such that desired effect is produced. A compound or composition described herein can be administered by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In preferred embodiments, the compositions are administered by intravenous infusion or injection.

By "treatment", "prevention" or "amelioration" of a disease or disorder is meant delaying or preventing the onset of such a disease or disorder, reversing, alleviating, ameliorating, inhibiting, slowing down or stopping the progression, aggravation or deterioration the progression or severity of a condition associated with such a disease or disorder. In one embodiment, at least one symptom of a disease or disorder is alleviated by at least 5%, at least 10%, at least 20%, at least 30%, at least 40%, or at least 50%.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments, the subject is a mammal, e.g., a primate, e.g., a human. The terms, "patient" and "subject" are used interchangeably herein. The terms, "patient" and "subject" are used interchangeably herein.

Preferably, the subject is a mammal. The mammal can be a human, non-human primate, mouse, rat, dog, cat, horse, or cow, but are not limited to these examples. Mammals other than humans can be advantageously used as subjects that represent animal models of disorders associated with inflammation.

In addition, the methods described herein can be used to treat domesticated animals and/or pets. A subject can be male or female. A subject can be one who has been previously diagnosed with or identified as suffering from or having a disorder a cancer or metastasis, but need not have already undergone treatment.

As used herein, the term "cancer" includes, but is not limited to, solid tumors and blood born tumors. The term cancer refers to disease of skin, tissues, organs, bone, cartilage, blood and vessels. The term "cancer" further encompasses primary and metastatic cancers. Examples of cancers that can be treated with the compounds of the invention include, but are not limited to, carcinoma, including that of the bladder, breast, colon, kidney, lung, ovary, pancreas, stomach, cervix, thyroid, and skin, including squamous cell carcinoma; hematopoietic tumors of lymphoid lineage, including, but not limited to, leukemia, acute lymphocytic leukemia, acute lymphoblastic leukemia, B-cell lymphoma, T-cell lymphoma, Hodgkins lymphoma, non-Hodgkins lymphoma, hairy cell lymphoma, and Burketts lymphoma; hematopoietic tumors of myeloid lineage including, but not limited to, acute and chronic myelogenous leukemias and promyelocytic leukemia; tumors of mesenchymal origin including, but not limited to, fibrosarcoma, rhabdomyosarcoma, and osteosarcoma; other tumors including melanoma, seminoma, tetratocarcinoma, neuroblastoma, and glioma; tumors of the central and peripheral nervous system including, but not limited to, astrocytoma, neuroblastoma, glioma, and schwannomas; and other tumors including, but not limited to, xenoderma, pigmentosum, keratoactanthoma, thyroid follicular cancer, and teratocarcinoma. The compounds of the invention are useful for treating patients who have been previously treated for cancer, as well as those who have not previously been treated for cancer. Indeed, the methods and compositions of this invention can be used in first-line and second-line cancer treatments.

The compounds of the invention are also useful in combination with known anti-cancer treatments, including radiation. The methods of the invention are especially useful in combination with anti-cancer treatments that involve administering a second drug that acts in a different phase of the cell cycle, e.g., S phase, than the epothilones of Formula (1a) or (Ib), which exert their effects at the G2-M phase.

Definitions

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

As used herein the term "comprising" or "comprises" is used in reference to compositions, methods, and respective component(s) thereof, that are essential to the invention, yet open to the inclusion of unspecified elements, whether essential or not.

Other than in the operating examples, or where otherwise indicated, all numbers expressing quantities of ingredients or reaction conditions used herein should be understood as modified in all instances by the term "about." The term "about" when used in connection with percentages may mean±1%.

The singular terms "a," "an," and "the" include plural referents unless context clearly indicates otherwise. Similarly, the word "or" is intended to include "and" unless the context clearly indicates otherwise.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

The term "alkyl" refers to saturated non-aromatic hydrocarbon chains that may be a straight chain or branched chain, containing the indicated number of carbon atoms (these include without limitation methyl, ethyl, propyl, iso-propyl, butyl, 2-methyl-ethyl, t-butyl, allyl, or propargyl), which may be optionally inserted with N, O, or S. For example, $C_1$-$C_6$ indicates that the group may have from 1 to 6 (inclusive) carbon atoms in it.

The term "alkenyl" refers to an alkyl that comprises at least one double bond. Exemplary alkenyl groups include, but are not limited to, for example, ethenyl, propenyl, butenyl, 1-methyl-2-buten-1-yl and the like.

The term "alkynyl" refers to an alkyl that comprises at least one triple bond.

The term "aryl" refers to monocyclic, bicyclic, or tricyclic aromatic ring system wherein 0, 1, 2, 3, or 4 atoms of each ring may be substituted by a substituent. Exemplary aryl groups include, but are not limited to, benzyl, phenyl, naphthyl, anthracenyl, azulenyl, fluorenyl, indanyl, indenyl, naphthyl, phenyl, tetrahydronaphthyl, and the like.

The term "cyclyl" or "cycloalkyl" refers to saturated and partially unsaturated cyclic hydrocarbon groups having 3 to 12 carbons, for example, 3 to 8 carbons, and, for example, 3 to 6 carbons, wherein the cycloalkyl group additionally may be optionally substituted. Exemplary cycloalkyl groups include, but are not limited to, cyclopropyl, cyclobutyl, cyclopentyl, cyclopentenyl, cyclohexyl, cyclohexenyl, cycloheptyl, cyclooctyl, and the like.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Exemplary heteroaryl groups include, but are not limited to, pyridyl, furyl or furanyl, imidazolyl, benzimidazolyl, pyrimidinyl, thiophenyl or thienyl, pyridazinyl, pyrazinyl, quinolinyl, indolyl, thiazolyl, naphthyridinyl, and the like.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Exemplary heterocyclyl groups include, but are not limited to piperazinyl, pyrrolidinyl, dioxanyl, morpholinyl, tetrahydrofuranyl, and the like.

The term "optionally substituted" means that the specified group or moiety, such as an alkyl group, alkenyl group, and the like, is unsubstituted or is substituted with one or more (typically 1-4 substituents) independently selected from the group of substituents listed below in the definition for "substituents" or otherwise specified.

The term "substituents" refers to a group "substituted" on an alkyl, alkenyl, alkynyl, cycloalkyl, aryl, heterocyclyl, or heteroaryl group at any atom of that group. Suitable substituents include, without limitation, halogen, hydroxy, oxo, nitro, haloalkyl, alkyl, alkenyl, alkynyl, alkaryl, aryl, aralkyl, alkoxy, aryloxy, amino, acylamino, alkylcarbanoyl, arylcarbanoyl, aminoalkyl, alkoxycarbonyl, carboxy, hydroxyalkyl, alkanesulfonyl, arenesulfonyl, alkanesulfonamido, arenesulfonamido, aralkylsulfonamido, alkylcarbonyl, acyloxy, cyano or ureido. In some cases, two substituents, together with the carbons to which they are attached to can form a ring.

As used herein, the term "polymer" refers to the product of a polymerization reaction, and is inclusive of homopolymers, copolymers, terpolymers, tetrapolymers, etc. The term "polymer" is also inclusive of random polymers, block polymers, graft polymers, copolymers, block copolymers, and graft copolymers. As used herein, the term "copolymer" refers to polymers formed by the polymerization reaction of at least two different monomers.

The term "copolymer backbone" as used herein refers to that portion of the polymer which is a continuous chain comprising the bonds formed between monomers upon polymerization. The composition of the copolymner backbone can be described in terms of the identity of the monomers from which it is formed without regard to the composition of branches, or sidechains, of the polymer backbone. The term "sidechain" refers to portions of the monomer which, following polymerization, forms an extension of the copolymer backbone.

As used herein, the term "biocompatible" refers to a material that is capable of interacting with a biological system without causing cytotoxicity, undesired protein or nucleic acid modification or activation of an undesired immune response. "Biocompatibility" also includes essentially no interactions with recognition proteins, e.g., naturally occurring antibodies, cell proteins, cells and other components of biological systems.

As used herein an ester sidechains means a sidechains of the formula —R'''C(O)—OR$^E$, where RE is independently C1-C6alkyl, C1-C6alkenyl, C1-C6alkynyl, cyclyl, heterocycly, aryl, or heteroaryl, each of which can be optionally substituted; and R''' is a bond or C1-C6 alkylene, were the alkylene can comprise one or more double or triple bonds and/or the backbone of the alkylene can be interrupted by O, S, S(O), NH, or C(O). Preferably R''' is a bond.

As used herein an amide sidechains means a sidechains of the formula —R''C(O)—N(R$^A$)$_2$, where RA is independently H, C1-C6alkyl, C1-C6alkenyl, C1-C6alkynyl, cyclyl, heterocycly, aryl, heteroaryl, saccharide, disaccharide, or trisaccharide, each of which can be optionally substituted; and R'' is a bond or C1-C6 alkylene, were the alkylene can comprise one or more double or triple bonds and/or the backbone of the alkylene can be interrupted by O, S, S(O), NH, or C(O). Preferably R'' is a bond.

As used herein a carboxylic acid chain means a sidechains of the formula —R''''C(O)OH where R'''' is a bond or C1-C6 alkylene, were the alkylene can comprise one or more double or triple bonds and/or the backbone of the alkylene can be interrupted by O, S, S(O), NH, or C(O). Preferably R'''' is a bond.

Some non-exhaustive examples of biocompatible polymers include polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methylmethacrylate), poly (ethylmethacrylate), poly(butylmethacrylate), poly (isobutylmethacrylate), poly(hexlmethacrylate), poly (isodecylmethacrylate), poly(laurylmethacrylate), poly (phenylmethacrylate), poly(methacrylate), poly (isopropacrylate), poly (isobutacrylate), poly (octadecacrylate), polyethylene, polypropylene poly (ethylene glycol), poly(ethylene oxide), poly(ethylene terephthalate), poly(vinyl alcohols), poly(vinyl acetate), poly vinyl chloride, polystyrene, polyhyaluronic acids, casein, gelatin, gluten, polyanhydrides, polyacrylic acid, alginate, chitosan, any copolymers thereof, and any combination of any of these. Additionally, biocompatible polymers and copolymers that have been modified for desirable enzymatic degradation, or change upon application of light, ultrasonic energy, radiation, a change in temperature, pH, osmolarity, solute or solvent concentration are also amenable to the present invention.

The present invention may be defined in any of the following numbered paragraphs:

1. A biocompatible conjugated polymer nanoparticle comprising:
   a copolymer backbone;
   a plurality of sidechains covalently linked to said backbone; and
   a plurality of platinum compounds dissociably linked to said sidechains.
2. The nanoparticle of paragraph 1, wherein said plurality of platinum compounds is selected from Pt(II) compounds, Pt(IV) compounds, and any combinations thereof.
3. The nanoparticle of paragraph 1 or 2, wherein at least one of said plurality of platinum compounds is linked to said sidechain through at least one coordination bond.
4. The nanoparticle of paragraph 3, wherein said coordination bond is between an oxygen of the sidechains and the platinum atom of the platinum compound.
5. The nanoparticle of paragraph 4, wherein said oxygen is a carbonyl oxygen.
6. The nanoparticle of paragraph 4, wherein said oxygen is an amide oxygen.
7. The nanoparticle of any of paragraphs 1-6, wherein said copolymer comprises maleic acid monomers.
8. The nanoparticle of paragraph 7, wherein at least one carboxylic acid of the maleic acid is derivatized to an amide.
9. The nanoparticle of any of paragraphs 1-8, wherein said copolymer is poly(isobutylene-alt-maleic acid) (PIMA).
10. The nanoparticle of any of paragraphs 1-9, wherein said copolymer comprises from 2 to 100 monomer units.
11. The nanoparticle of any of paragraphs 1-10, wherein said copolymer comprises from 25 to 50 monomer units.
12. The nanoparticle of any of paragraphs 1-11, wherein said sidechains are selected from the group consisting of polymers, monosaccharides, dicarboxylic acids, and combinations thereof.
13. The nanoparticle of any of paragraphs 1-12, wherein said sidechains are polyethylene glycol (PEG).
14. The nanoparticle of paragraph 13, wherein said PEG sidechains have a molecular weight of from 100 to 5000 Dalton.
15. The nanoparticle of paragraph 13, wherein said PEG sidechains have a molecular weight of from 1000 to 3000 Dalton.
16. The nanoparticle of paragraph 13, wherein said PEG sidechains have a molecular weight of about 2000 Dalton.
17. The nanoparticle of any of paragraphs 1-12, wherein said sidechains are monosaccharides.
18. The nanoparticle of paragraph 17, wherein said monosaccharides are glucosamine.
19. The nanoparticle of any of paragraphs 1-18, wherein said platinum compound is a Pt(II) compound selected from the group consisting of cisplatin, oxaliplatin, carboplatin, paraplatin, sartraplatin, and combinations thereof.
20. The nanoparticle of paragraph 19, wherein said platinum (II) compound is cisplatin.
21. The nanoparticle of paragraph 19, wherein said platinum compound is oxaliplatin.
22. The nanoparticle of any of paragraphs 1-21, wherein the number of sidechains corresponds between 50% and 100% of the number of monomeric units of said polymer backbone.
23. The nanoparticle of any of paragraphs 1-22, wherein the number of said sidechains corresponds to a number greater than 90% of the number of monomeric units of said polymer backbone.
24. The nanoparticle of any of paragraphs 1-23, wherein the number of said platinum compounds corresponds between 10% and 100% of the number of monomeric units of said polymer backbone.
25. The nanoparticle of any of paragraphs 1-24, wherein the number of said platinum compounds corresponds between 25% and 75% of the number of monomeric units of said polymer backbone.
26. The nanoparticle of any of paragraphs 1-25, wherein said sidechains comprise dicarboxylic acids.
27. The nanoparticle of paragraph 26, wherein said dicarboxylic acids are of the formula HOOC—R—COOH, wherein R is a $C_1$-$C_6$alkyl, $C_2$-$C_6$alkenyl, or $C_2$-$C_6$alkynyl.
28. The nanoparticle of paragraph 27, wherein said dicarboxylic acid is maleic acid.
29. A biocompatible conjugated polymer nanoparticle comprising:
   a poly(isobutylene-alt-maleic acid) backbone, wherein said backbone contains 25 to 50 monomer units;
   a plurality of PEG sidechains covalently linked to said backbone, wherein said PEG sidechains have a molecular weight of from 1000 to 3000 Dalton and wherein the number of said PEG sidechains corresponds to between 50% and 100% of the number of monomeric units of said polymer backbone; and
   a plurality of cisplatin sidegroups dissociably linked to said backbone wherein the number of said cisplatin sidegroups is between 25% and 75% of the number of monomeric units of said polymer backbone.
30. A biocompatible conjugated polymer nanoparticle comprising:
   a poly(isobutylene-alt-maleic acid) backbone, wherein said backbone consist of 40 monomers;
   a plurality of PEG sidechains covalently linked to said backbone, wherein said PEG sidechains have a molecular weight of 2000 Dalton and wherein the number of said PEG sidechains is greater than 90% of monomeric units of said polymer backbone; and
   a plurality of cisplatin sidegroups dissociably linked to said backbone, wherein the number of said cisplatin sidegroups is between 25% and 75% of the number of monomeric units of said polymer backbone.
31. A biocompatible conjugated polymer nanoparticle comprising:
   a poly(isobutylene-alt-maleic acid) backbone, wherein said backbone comprises from 25 to 50 monomers;
   a plurality of glucosamine sidechains covalently linked to said backbone and wherein the number of said glucosamine sidechains is between 50% and 100% of monomeric units of said polymer backbone; and
a plurality of cisplatin sidegroups dissociably linked to said backbone, wherein the number of said cisplatin sidegroups is between 25% and 75% of the number of monomeric units of said polymer backbone.

32. A biocompatible conjugated polymer nanoparticle comprising:
a poly(isobutylene-alt-maleic acid) backbone, wherein said backbone comprises from 25 to 50 monomers;
a plurality of glucosamine sidechains covalently linked to said backbone and wherein the number of said glucosamine sidechains is greater than 90% of monomeric units of said polymer backbone; and
a plurality of cisplatin sidegroups dissociably linked to said backbone, wherein the number of said cisplatin sidegroups is between 25% and 75%, inclusive, of the number of monomeric units of said polymer backbone.

33. A carboxylic acid-platinum compound complex conjugated nanoparticle comprising:
a carboxylic acid-platinum compound complex; and
a plurality of lipid-polymer chains, wherein the carboxylic acid portion of said carboxylic acid-platinum compound complex is covalently bound to said lipid-polymer chains.

34. The nanoparticle of paragraph 33, wherein the carboxylic acid is maleic acid.

35. The nanoparticle of any of paragraphs 33-34, wherein the polymer is PEG.

36. The nanoparticle of any of paragraphs 33-35, wherein the platinum compound is a Pt(II) compound selected from the group consisting of cisplatin, oxaliplatin, carboplatin, paraplatin, sartraplatin, and combinations thereof.

37. The nanoparticle of paragraph 36, wherein the Pt(II) compound is cisplatin.

38. The nanoparticle of any of paragraphs 33-37, wherein the platinum compound loading is from 1%-30%.

39. The nanoparticle of any of paragraphs 33-38, wherein the platinum compound loading is from 1%-6%.

40. A vesicle, micelle, or liposome compound comprising a plurality of nanoparticles of any of paragraphs 33-39.

41. A dicarbonyl-lipid compound having the structure

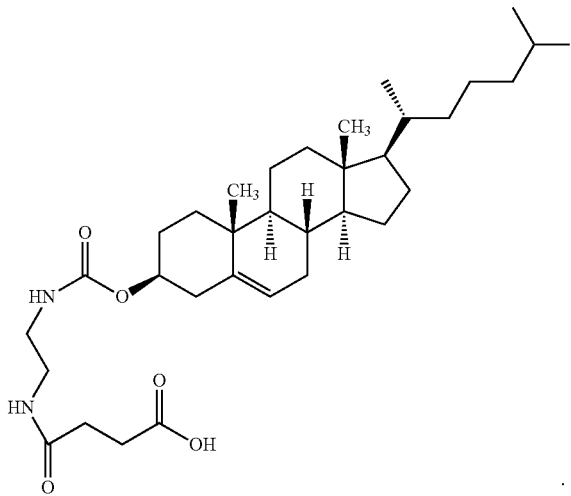

42. A vesicle, micelle, liposome or nanoparticle compound comprising a dicarbonyl-lipid compound of paragraph 41 and a platinum compound, wherein the platinum compound is dissociably linked to the compound of paragraph 41.

43. The nanoparticle of paragraph 42, wherein the platinum compound is selected from Pt(II) compounds, Pt(IV) compounds, and any combinations thereof.

44. The nanoparticle of paragraph 43, wherein said platinum compound is a Pt(II) compound selected from the group consisting of cisplatin, oxaliplatin, carboplatin, paraplatin, sartraplatin, and combinations thereof.

45. The nanoparticle of paragraph 43, wherein said platinum (II) compound is cisplatin.

46. The nanoparticle of paragraph 43, wherein said platinum compound is oxaliplatin.

47. A nanoparticle compound comprising a biocompatible polymer, wherein the polymer comprises at least one monomer having the formula —CH($CO_2$H)—R—CH(C(O)R')—, wherein R is a bond, $C_1$-$C_6$ alkylene, where the alkylene can comprise one or more double or triple bonds; and R' is a substituted nitrogen atom. Preferably, R is a bond.

48. The nanoparticle of paragraph 47, wherein the polymer comprises from 2 to 100 monomeric units having the formula —CH($CO_2$H)—R—CH(C(O)R')—.

49. The nanoparticle of any of paragraphs 47-48, wherein the polymer comprises from 25 to 50 monomeric units having the formula —CH($CO_2$H)—R—CH(C(O)R')—.

50. The nanoparticle of any of paragraphs 47-49, wherein R' is

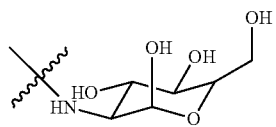 [SMILES: *NC1C(O)OC(CO)C(O)C1O]

or —NH($CH_2CH_2O)_m$$CH_3$, wherein m is 1-150.

51. The nanoparticle of any of paragraphs 47-50, further comprising a bioactive agent.

52. A pharmaceutical composition comprising:
the nanoparticle or compound of paragraphs 1-51; and
a pharmaceutically acceptable carrier.

53. A method of treating cancer or metastasis comprising:
administering to a subject in need thereof an effective amount of the composition of any of paragraphs 1-52.

54. The method of paragraph 53, wherein said cancer or metastasis is selected from the group consisting of platinum susceptible or resistant tumors.

55. The method of paragraph 54, wherein said cancer or metastasis is selected from the group consisting of breast, head and neck, ovarian, testicular, pancreatic, oral-esophageal, gastrointestinal, liver, gall bladder, lung, melanoma, skin cancer, sarcomas, blood cancers, brain tumors, glioblastomas, tumors of neuroectodermal origin and any combinations thereof.

56. A method of sustain release of a platinum compound at a specific location in a subject comprising: providing at the location a composition of paragraph the composition of any of paragraphs 1-52.

57. The method of paragraph 56, wherein composition is in the form of a gel.

58. The method of any of paragraphs 56-57, wherein the location is a tumor.

59. The method of paragraph 58, wherein the tumor was removed before providing the composition.

To the extent not already indicated, it will be understood by those of ordinary skill in the art that any one of the various embodiments herein described and illustrated may be further modified to incorporate features shown in any of the other embodiments disclosed herein.

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

EXAMPLES

Materials and Methods

CellTiter 96 AQueous One Solution Cell Proliferation Assay [3-(4,5-dimethylthiazol-2-yl)-5-(3-carboxymethoxyphenyl)-2-(4-sulfophenyl)-2H-tetrazolium, inner salt (MTS) assay] reagent was from Promega (Madison, Wis.). All Polymer solutions were dialyzed in cellulose membrane tubing, types Spectra/Por 4 and Spectra/Por 6 (wet tubing), with mass-average molecular mass cut-off limits of 1000 and 3500 respectively. Operations were performed against several batches of stirred deionized H2O. Commercially supplied (Sigma, Fluka A G, Aldrich Chemie GmbH) chemicals, reagent grade, were used as received. These included N,N-Dimethylformamide (DMF), Poly(isobutylene-alt-maleic anhydride), Glucosamine.HCl, mPEG2000NH$_2$, Diaza (1,3)bicycle[5.4.0]udecane (DBU), Triethyl amine. $^1$H NMR and $^{13}$C NMR were measured at 300 and 400 MHz, respectively, with a Varion-300 or a Brucker-400 spectrometer. 1H NMR chemical shifts are reported as δ values in parts per million (ppm) relative to either tetramethylsilane (0.0 ppm) or deuterium oxide (4.80 ppm). Data is reported as follows: chemical shift, multiplicity (s=singlet, d=doublet, t=triplet, q=quartet, m=mutliplet, b=broad), coupling constants (hertz), and integration. Carbon-13 chemical shifts are reported in ppm relative to CDCl3 (76.9 ppm) or relative to DMSOd$_6$ (39.5 ppm). $^{195}$Pt NMR chemical shifts are reported as δ in ppm relative to Na$_2$PtCl$_6$ (0.0 ppm). In some experiments, $^1$H NMR and $^{13}$C NMR were measured at 500 and 125 MHz, respectively, with a Varion 500 or a Brucker-400 spectrometer.

Starting materials were azeotropically dried prior to reaction as required, and all air- and/or moisture-sensitive reactions were conducted in flame- and/or oven-dried glassware under an anhydrous nitrogen atmosphere with standard precautions taken to exclude moisture.

Cell Culture and Cell Viability Assay

The Lewis Lung Carcinoma cell lines (LLC) and Breast Cancer cell line (4T1) were purchased from American Type Culture Collection (ATCC, Rockville, Md., USA). Lewis Lung Carcinoma cells were cultured in Dulbecco's Modified Eagle's Medium supplemented with 10% FBS, 50 unit/ml penicillin and 50 unit/ml streptomycin. The 4T1 cells were cultured in RPMI medium supplemented with 10% FBS, 50 unit/ml penicillin and 50 unit/ml streptomycin. Trypsinized cultured LLC and 4T1 cells were washed twice with PBS and seeded into 96-well flat bottomed plates at a density of 2×10$^3$ cells in 100 µl of medium. Different concentrations of conjugates were tested in triplicate in the same 96-well plate for each experiment. Medium alone was kept as negative control and CDDP as positive control. The plates were then incubated for 48 h in a 5% CO$_2$ atmosphere at 37° C. The cells were washed and incubated with 100 µl phenol-red free medium (without FBS) containing 20 µl of the CellTiter 96 Aqueous One Solution reagent (Promega, Wis., USA). This assay [3-(4,5-dimethylthiazol-2-yl)-5-(3-carboxymethoxyphenyl)-2-(4-sulfophenyl)-2H-tetrazolium, inner salt] (MTS) is a colorimetric method for determining the number of viable cells in proliferation or cytotoxicity assays. After 2-h incubation in a 5% CO$_2$ atmosphere at 37° C., the absorbance in each well was recorded at 490 nm using a VERSA max plate reader (Molecular Devices, Sunnyvale, Calif., USA).

The absorbance reflects the number of surviving cells. Blanks were subtracted from all data and results analyzed using Origin software (OriginLab Corporation, Northampton, USA). The mean of triplicated absorbance data for each tested dose was divided by the mean of untreated control cells. The log of the quotient was used to plot a graph as a function of given dose, i.e. Y=(Tested Absorbance Mean–Background)/(Untreated Absorbance Mean–Background) vs. X=tested dose.

Particle Size Measurement

High resolution TEM images were obtained on a JEOL 2011 high contrast digital TEM. Samples were prepared on carbon 300 mesh copper grids (Electron Microscopy Sciences) by adding drops of aqueous nanoparticles at different concentrations, and allowed to air-dry. The size distribution of nanoparticles was studied by dynamic light scattering (DLS), which was performed at 25° C. on a DLS-system (Malvern NanoZetasizer) equipped with a He Ne laser.

Physicochemical Release Kinetics Studies

PIMA-GA-CDDP was suspended in 1 mL of hypoxic-cell lysate from LLC cell line and sealed in a dialysis bag (MWCO~1000 Da). The dialysis bag was incubated in 1 mL of PBS buffer at room temperature with gentle shaking. 10 □L of aliquot was extracted from the incubation medium at predetermined time intervals, treated with 90 □L of 1,2-phenylene diamine solution (1.2 mg in 1 mL DMF) and incubated for 3 h at 100° C. The released Pt(IV) was quantified by UV-VIS spectroscopy at characteristic wavelength □=704 nm of Pt(IV)-1.2-phenylene diamine complex. After withdrawing each aliquot the incubation medium was replenished by 10 □L of fresh PBS.

Alternatively, concentrated PIMA-GA-cisplatin conjugate was resuspended into 100 µL of double distilled water with pH adjusted to 8.5 or 5.5 using IN sodium hydroxide or IN nitric acid and transferred to a dialysis tube (MWCO: 1000 KD, Spectrapor). The dialysis tube was put into a tube containing magnetic pallet and 2 mL solutions of different pH phosphate-buffered saline. Cisplatin release was studied by gently stirring the dialysis bag at 300 rpm using IKA stirrer at 25° C. 10 µL aliquots were taken from the outside solution of dialysis membrane bag at predetermined time intervals and subjected to next UV-Vis active complex formation reaction by adding 100 µL of ortho-phenyl-diamine (1.2 mg/ml in DMF) and heating the resulting solution for 3 h. 10 µL of fresh solution was added back to outside solution of dialysis membrane bag to maintain same volume. The amount of the drug that was released was evaluated by UV-spectrophotometer (Shimadzu UV 2450) at 706 nm.

FACS Analysis for Apoptosis

Cells were grown in 6-well plates incubated in the presence of cisplatin nanoparticle or free cisplatin at 37° C. for 24 h. After 24 h, the cells were washed with PBS and collected at 0° C. The cells were then treated with annexin V-Alexa Fluor 488 conjugate (Molecular Probes, Invitrogen) and incubated in the dark, at room temperature, for 15 min. The cells were then washed with PBS and incubated with propidium iodide (PI) solution (50 g/mL; Sigma) containing RNase (1 mg/mL; Sigma). The cell suspensions were then transferred to FACS tubes and analyzed for AnnexinV/PI staining on a BD FACS Calibur instrument. Data were analyzed using a CellQuestPro software (BD Biosciences).

Cellular Uptake Studies

LLC and 4T1 cells were seeded on glass coverslips in 24-well plates, 50000 cells per well. When cells reached 70% confluency, they were treated with fluorescein isothiocyanate (FITC)-conjugated cisplatin nanoparticles for different durations of 30 min, 2 h, 6 h, 12 h, and 24 h, respectively. For colocalization studies, at indicated time points, the cells were washed with PBS and incubated with Lysotracker Red (Molecular Probes) at 37° C. for 30 min to allow internalization. The cells were then fixed with 4% paraformaldehyde for 20 min at room temperature, then washed twice with PBS and mounted on glass slides using Prolong Gold Antifade Reagent (Molecular Probes). Images were obtained using a Nikon Eclipse TE2000 fluorescence microscope equipped with green and red filters for FITC and Lysotracker Red, respectively.

In Vivo Murine LLC Lung Cancer and 4T1 Breast Cancer Tumor Model

The LLC Lung Cancer cells and 4T1 Breast Cancer cells (3×105) were implanted subcutaneously in the flanks of 4-week-old C57/BL6 and BALB/c mice (weighing 20 g, Charles River Laboratories, MA) respectively. The drug therapy was started after the tumors attained volume of 50 $mm^3$. The tumor therapy consisted of administration of cisplatin nanoparticle and free cisplatin or oxaliplatin and free oxaliplatin. The formulations were prepared and validated such that 100 μL of cisplatin nanoparticle and free cisplatin contained 1.25 and 3 mg/kg of cisplatin or 100 μL of oxaliplatin nanoparticle and free oxaliplatin contained 5 and 15 mg/kg of oxaliplatin Administration was by tail vein injection. PBS (100 μL) administered by tail-vein injection was used as a control for drug treatment. The tumor volumes and body weights were monitored on a daily basis. The animals were sacrificed when the average tumor size of the control exceeded 2000 $mm^3$ in the control group. The tumors were harvested immediately following sacrifice and stored in 10% formalin for further analysis. All animal procedures were approved by Harvard institutional IUCAC.

In Vivo Murine Ovarian Cancer Tumor Model

Ovarian adenocarcinomas were induced in genetically-engineered K-ras$^{LSL/+}$/Pten$^{fl/fl}$ mice via intrabursal delivery of adenovirus carrying Cre recombinase, as described previously. Tumor cells were engineered to express luciferase once activated by Adeno-Cre, in order to make tumor imaging feasible before and after drug treatment. Once mice developed medium to large tumors they were placed into one of four treatment groups (controls, cisplatin NP1.25 mg/kg, cisplatin NP-3 mg/kg, and free cisplatin), with all drugs administered intravenously (i.v.).

Tumor Imaging and Efficacy Assessment of Drug Treatment

Tumor imaging in vivo was performed with the IVIS Lumina II Imaging System. Quantification of bioluminescence was achieved by using the Living Image Software 3.1 (Caliper Life Sciences). Mice received 150 mg/kg of D-luciferin firefly potassium salt via intraperitoneal (i.p.) injection prior to imaging. Five minutes post-luciferin injection, animals were anesthetized in a 2.5% isoflurane induction chamber. Once anesthesized, mice were placed into the imaging chamber where they were kept under anesthesia by a manifold supplying isoflurane and their body temperature was maintained by a 37° C. temperature stage. Bioluminescent signal was collected fifteen minutes after luciferin administration for an exposure time of thirty seconds. Images were taken a day prior to treatment (day 0, baseline), in the middle of the treatment cycle, and one day following the final treatment. Treatment efficacy was quantified by examining the fold increase in bioluminescence of the post-treatment signal as compared to baseline. Statistical analysis of the toxicity data was analyzed using a one-way ANOVA test with the Prism 5™ software.

Biodistribution of Cisplatin

Cisplatin-nanoparticles and free cisplatin were injected i.v. (dose equivalent to 8 mg/Kg of cisplatin) in mice to study its distribution. After 24 hours of injections, the animals were sacrificed and necropsy was performed to harvest the tumor and kidney. In another study, the animals were dosed repeatedly following the efficacy study protocols, and the animals were sacrificed at the end of the multiple dosing study. The organs were then weighed and dissolved in Conc. $HNO_3$ (approx. 10 mL) by shaking for 24 hours at room temperature and then heating at 100° C. for 12 hours. To these mixtures were then added 30% $H_2O_2$, the resulting solutions were stirred for 24 hours at room temperature and then heated for another 12 hours to evaporate the liquids. All solid residues were re-dissolved in 1 mL water and then amount of platinum was measured by inductively coupled plasma-spectrometry (ICP).

Histopathology and TUNEL Assay (Apoptolic Assay)

The tissues were fixed in 10% formalin, paraffin embedded, sectioned and stained with H&E at the Harvard Medical School Core Facility. Tumor and Kidney paraffin sections were deparaffinized and stained with standard TMR-red fluorescent terminal deoxynucleotidyl transferase-mediated dUTP nick end labeling (TUNEL) kit following the manufacturer's protocol (In Situ Cell Death Detection Kit, TMR Red, Roche). Images were obtained using a Nikon Eclipse TE2000 fluorescence microscope equipped with red filter.

Toxicity Assessment of Drug Treatment

Body weights were recorded daily to assess toxicity. In addition, livers and spleens were removed at the end of treatment to record weights and perform extensive pathological examination to assess toxicity of vital organs. Cell apoptosis in vital organs was measured using TUNEL assay. Statistical analysis of the toxicity data was performed using a two-way ANOVA test with the Prism 5™ software.

Statistical Analysis

Data were expressed as means±S.D from at least n=3. Statistical analysis was conducted using the GraphPad Prism software (GraphPad, San Diego, Calif.). The statistical differences were determined by ANOVA followed by Newman Keuls Post Hoc test or Student's t test. p<0.05 was consideredtoindicate significant differences.

Example 1

Synthesis of Polymeric Carriers

Poly(Isobutylene-alt-Maleic Acid) PIMA (2)

Poly(isobutylene-alt-maleic anhydride) 1 (1 g) was dissolved in 5 ml of dry DMF in 10 mL round bottom flask to which was added double distilled water (1 mL) and then resulting reaction mixture was stirred at 80° C. for 48 h. Solvent was removed under vacuum and low molecular weight impurities were removed using dialysis. Aqueous polymer solution was dialyzed for 3 days in cellulose membrane tubing, types Spectra/Por 4 and with mass-average molecular mass cut-off limits of 1000. The colorless solution was then lyophilized to get 732 mg of white colored polymer Poly(isobutylene-alt-maleic acid) PIMA (2). $^1$H NMR (300 MHz, $D_2O$) δ 3.3-3.5 (m), 2.8 (s), 2.6-2.7 (m), 2.5 (s), 2.2-2.3 (m), 0.8-0.9 (m).

PIMA-EDA (3)

The 10 mL RB flask equipped with magnetic stirrer and dry nitrogen balloon was charged with Poly(isobutylene-altmaleic anhydride) PIMA 1 (1 g), dry DMF (5 mL), Triethyl amine (0.1 mL) and excess Ethylendiamine dihydrochloride (1 g). The resulting mixture was stirred at 25° C. for 48 h. Solvent was removed under vacuum and polymer was purified by removing low molecular weight impurities such as excess Ethylendiamine using dialysis bag of molecular cut off of 3.5 KD for 3 days. The polymer solution was then lyophilized to get 0.89 g of PIMA-EDA (3). $^1$H-NMR (300 MHz, D$_2$O) δ 3.1-3.2 (m), 2.9-3.0 (m), 2.6-2.8 (m), 2.5 (m), 0.8-1.0 (m).

PIMA-GA Polymer (4)

Poly(isobutylene-alt-maleic anhydride) PIMA 1 (0.0064 g 0.001 mmol) was dissolved in DMF (5 mL) and then was added DBU (0.032 mL, dissolved in 1 mL dry DMF, 0.21 mmol) and the mixture was stirred at 25° C. for 1 h. To this solution was added Glucosamine (0.046 g 0.21 mmol) directly. The resulting reaction mixture was allowed to stir at room temperature for 48 h and then quenched by adding double distilled water (1 mL). The organic solvent was evaporated under vacuum for 12 hours. The resulting pale yellow solid was purified by dialysis for 3 days using dialysis bag supplied by Pierce (Thermoscientific) of molecular cut off of 3.5 KD to colorless solution. Lyophilization gave 104 mg of white colored PIMA-GA (4) polymer. $^1$H-NMR (300 MHz, CDC$^{13}$) δ 7.54-7.65 (m, 2 H), 7.33-7.45 (m, 2 H), 7.02-7.19 (m, 14 H), 6.93-6.97 (m, 2 H), 6.83-6.89 (m, 2 H), 6.55 (s, 2 H), 6.15-6.19 (m, 2 H), 3.90 (s, 2 H), 3.58 (s, 6 H). $^1$H-NMR (300 MHz, D$_2$O) δ 8.2-8.3 (m), 7.0-7.1 (m), 5.0-5.1 (m), 3.0-3.9 (m), 2.1-2.3 (m), 1.1-1.9 (m), 0.7-1.0 (m).

In another experiment, PIMA (0.045 g) was dissolved in DMF (5 mL) and then was added solution of DBU (0.23 mL) and glucosamine (0.323 g dissolved in 5 mL dry DMF). The resulting reaction mixture was allowed to stir at room temperature for 48 h and then quenched by adding dd water (1 mL). The organic solvent was evaporated under vacuum. The resulting pale yellow solid was purified by dialysis for 3 days using dialysis bag of molecular cut off of 3.5 KD. Lyophilization gave 104 mg of slightly yellow colored PIMA-GA polymer. $^1$H-NMR (300 MHz, D$_2$O) δ 8.2-8.3 (m), 7.07.1 (m), 5.0-5.1 (m), 3.0-3.9 (m), 2.1-2.3 (m), 1.1-1.9 (m), 0.7-1.0 (m).

PIMA-PEG Polymer (5)

The Poly(isobutylene-alt-maleic anhydride) PIMA 1 (3 mg, 0.0005 mmol) and DBU (0.0023 mL, 0.015 mmol) was dissolved in Dry DMF (10 mL) in 25 mL RB flask under N$_2$ for 1 h and then was added PEG-NH$_2$ (20 mg, 0.01 mmol), the resulting reaction solution was then heated at 80° C. with continuous stirring for 3 days. The reaction was allowed to cool to room temperature and then water (1 mL) was added and continue stirring for 1 h. Solvents are removed under vacuum and unreacted PEG-NH$_2$ of MW 2 KD was removed from required polymer by dialysis. Dialysis was carried out for 5 days using membrane of molecular cut off of 3.5 KD supplied by Pierce (Thermoscientific) to give colorless solution which was then lyophilized to give 19 mg white colored PIMA-PEG (5). $^1$H-NMR (300 MHz, D$_2$O) δ 3.5-3.7 (m), 3.0-3.1 (m), 2.5-2.8 (m), 0.7-1.0 (m).

Example 2

Synthesis of Conjugates

Aquation of CDDP

CDDP (30 mg) and AgNO$_3$ (17 mg) was added to 10 ml double distilled water. The resulting solution was stirred in dark at room temperature for 24 h. AgCl precipitates were found after reaction. AgCl precipitates are removed from reaction by centrifugation at 10000 rpm for 10 min. The supernatant was further purified by passing through 0.2 μm filter.

PIMA-CDDP (6)

Poly(isobutylene-alt-maleic acid) PIMA 2 (0.006 g, 0.001 mmol) was dissolved in 1 ml double distilled water containing CDDP (0.00084 g, 0.0028 mmol) in 10 mL round bottom flask to and then resulting reaction mixture was stirred at room temperature (25° C.) for 48 h. The PIMA-CDDP (6) conjugate was further purified by dialyzing it in cellulose membrane tubing, types Spectra/Por 4 and with mass-average molecular mass cut-off limits of 1000. The resulting turbid solution was then lyophilized to get white colored PIMA-CDDP (6) conjugate. The conjugate was re-suspended for cell culture experiments.

PIMAA-EDA-CDDP (7)

In 10 mL RB flask was weighed PIMA-EDA 3 (0.007 g, 0.001 mmol) polymer to which was added CDDP (0.0084 g, 0.0028 mmol) dissolved in double distilled water (1 mL). The solution was then stirred at room temperature (25° C.) for 48 h. Dialysis using cellulose membrane with molecular mass cut-off limits of 1000 and lyophilization gave yellowish colored PIMA-EDA-CDDP (7) conjugate.

PIMAA-GA-CDDP (8)

To PIMA-GA 4 (0.0036 g, 0.0003 mmol) weighed in 10 mL RB flask equipped with magnetic stirrer was added 1 ml double distilled water containing CDDP (0.001 g, 0.0033 mmol) and then the solution was stirred at room temperature (25° C.) for 48 h. The PIMA-GA-CDDP (8) conjugate formed in solution was further purified by dialysis to remove unattached CDDP with mass-average molecular mass cut-off limits of 1000 for 2-3 hours. Lyophilization of the dialyzed solution resulted in slightly yellow colored PIMA-GA-CDDP (8) conjugate.

PIMA-PEG-CDDP (9)

The brush polymer PIMA-PEG 5 (0.019 g, 0.00007 mmol) was taken in 10 mL RB flask mixed with CDDP (0.0002 g, 0.0007 mmol) dissolved in 0.3 mL double distilled water. After stirring for 3 days at room temperature (25° C.) the resulting turbid reaction mixture was dialyzed. The solution containing PIMA-PEG-CDDP (2) conjugate was further purified by dialyzing it in cellulose membrane tubing, types Spectra/Por 4 and with mass-average molecular mass cut-off limits of 1000 for 2-3 hours to remove free CDDP. PIMA-PEG-CDDP (9) conjugate was then lyophilized to get white colored solid. The conjugate was re-suspended in double distilled water for cell culture experiments.

FITC-Labeled PIMA-GA-CDDP

Poly(isobutylene-alt-maleic anhydride) PIMA (0.006 g) was dissolved in DMF (5 mL) and then was added a solution of DBU (0.0053 mL in DMF) and Glucosamine (0.0075 g dissolved in 5 mL dry DMF) the mixture was stirred at 25° C. for 1 h. The resulting reaction mixture was allowed to stir at 25° C. for 48 h and then to which was added 0.0022 g FITC-EDA (FITC-EDA was synthesized by stirring Fluorescein isothiocyanate in excess ethylene diamine at 25° C. for 12 h in DMSO) and continue stirring for another 12 h, reaction mixture was quenched by adding double distilled water (1 mL). The organic solvent was evaporated under vacuum. The resulting orange solid was purified by dialysis for 3 days using dialysis bag of molecular cut off of 3.5 KD. Lyophilization gave fluorescent orange PIMA-GA-FITC polymer. To this FITC labeled polymer (PIMA-GA-FITC, 0.004 g) was added 1 ml double distilled water containing cisplatin (0.001 g) and then the solution was stirred at room temperature (25° C.) for 48 h. The PIMA-GA-FITC-cisplatin conjugate formed in solution was further purified by dialysis to remove unattached cisplatin with mass-average molecular mass cut-off limits of 1000. Lyophilization of the dialyzed solution resulted in orange colored FITC labeled PIMA-GAFITC-cisplatin conjugate nanoparticles.

PIMA-Oxaliplatin

Poly(isobutylene-alt-maleic acid) (PIMA) (6 mg) was dissolved in 1 ml double distilled water containing oxaliplatin-OH (1 mg) in a round bottom flask to and then resulting reaction mixture was stirred at room temperature (25° C.) for 48 h. The PIMA-oxaliplatin conjugate was further purified by dialyzing it in cellulose membrane tubing, types Spectra/Por 4 and with mass-average molecular mass cut-off limits of 1000. The resulting turbid solution was then lyophilized to get PIMA-oxaliplatin conjugate. The conjugate was re-suspended for cell culture experiments.

PIMA-GA-Oxaliplatin

To PIMA-GA (12 mg) weighed in 10 mL RB flask equipped with magnetic stirrer was added 1 ml double distilled water containing oxaliplatinOH (1 mg) and then the solution was stirred at room temperature (25° C.) for 48 h. The PIMA-GA-oxaliplatin conjugate formed in solution was further purified by dialysis to remove unattached oxaliplatin with mass-average molecular mass cut-off limits of 1000. Lyophilization of the dialyed solution resulted in yellow colored PIMA-GA-oxaliplatin conjugate.

Example 3

NMR Analysis of PIMA-GA Polymer Synthesis Using Different Bases

Synthesis of PIMA-GA Using DBU as the Base

Glucosamine hydrochloride (360 mg, 1.66 mmol, 200 equiv) was suspended in 5 mL DMF and treated with DBU (250 $\mu$L, 1.66 mmol, 200 equiv) at room temperature for 1 h. After 1 h glucosamine/DBU (in DMF) solution was added drop wise into poly (isobutylene-alt-maleic anhydride) (50 mg, 0.008 mmol, 1 equiv) solution in 5 mL DMF and the reaction mixture was stirred for 72 h at room temperature. The reaction mixture was quenched with 3 mL of dd-water. The PIMA-GA conjugate was purified by dialysis using 2000 MWCO dialysis bag for 72 h. The product was lyophilized for 48 h to obtain 100 mg cream yellow powder. The product was characterized by $^1$H NMR spectroscopy (300 MHz). Solubility: product was soluble in water but not soluble in organic solvent e.g. acetone, methanol or acetonitrile. $^1$H NMR (300 MHz): $\delta$ (ppm)=5.2-5.3 (m, 0.14 H, sugar proton), 5.0-5.1 (m, 0.4 H, sugar proton), 3.6-4.0 (m, 13.07 H, sugar proton), 3.25-3.5 (m, 15.48 H, sugar proton), 3.0-3.2 (m, 6.98 H, sugar proton), 2.5-2.6 (m, 6.97 H, PIMA proton), 1.4-1.7 (m, 19.86 H, PIMA proton), 0.7-1.2 (m, 23.77 H, PIMA proton). Total sugar protons: total PIMA protons=36.07:50.6=0.71. This fits well with the predicted structure if all the residues are derivatized sugar protons and PIMA protons in PIMA-GA conjugate monomer.

Synthesis of PIMA-GA Using Diisoproylethylamine (DIPEA) as Base

Glucosamine hydrochloride (179 mg, 0.83 mmol, 100 equiv) was suspended in 2 mL DMF and treated with DIPEA (145 $\mu$L, 0.83 mmol, 100 equiv) at room temperature for 1 h. After 1 h poly (isobutylene-alt-maleic anhydride) (50 mg, 0.008 mmol, 1 equiv) (dissolved in 3 mL DMF) was added into the reaction mixture and stirred for 24 h at room temperature. The reaction mixture was quenched with 3 mL of dd-water. The PIMA-GA conjugate was purified by dialysis using 1000 MWCO dialysis bag for 24 h. The product was lyophilized for 48 h to obtain 106 mg white powder. The product was characterized by $^1$H NMR spectroscopy (300 MHz). Solubility: product was soluble in water but not soluble in organic solvent e.g. acetone, methanol or acetonitrile. $^1$H NMR (300 MHz): $\delta$ (ppm)=5.2-5.3 (m, 0.4 H, sugar proton), 4.9-5.1 (m, 2.0 H, sugar proton), 3.4-3.6 (m, 21.86 H, sugar proton), 3.2-3.3 (m, 6.16 H, sugar proton), 2.9-3.1 (m, 3.81 H, sugar proton), 2.4-2.7 (broad, 4.39 H, PIMA proton), 2.1-2.4 (broad, 4.54 H, PIMA proton), 1.7-2.0 (broad, 3.13 H, PIMA proton), 1.3-1.5 (broad, 1.58 H, PIMA proton), 1.1-1.2 (m, 24.12 H, PIMA proton), 0.6-0.9 (m, 27.94 H, PIMA proton). Total sugar protons: total PIMA protons=39.21:61.11=0.64.

Synthesis of PIMA-GA Using Trietylamine as Base

Glucosamine hydrochloride (143 mg, 0.66 mmol, 80 equiv) was suspended in 2 mL DMF and treated with triethylamine (100 $\mu$L, 0.66 mmol, 80 equiv) at room temperature for 1 h. After 1 h poly (isobutylene-alt-maleic anhydride) (50 mg, 0.008 mmol, 1 equiv) was added into the reaction mixture and stirred for 24 h at room temperature. The reaction mixture was quenched with 3 mL of dd-water. The PIMA-GA conjugate was purified by dialysis using 1000 MWCO dialysis bag for 24 h. The product was lyophilized for 48 h to obtain 100 mg white powder. The product was characterized by $^1$H NMR spectroscopy (300 MHz). Solubility: product was soluble in water but not soluble in organic solvent e.g. acetone, methanol or acetonitrile. $^1$H NMR (300 MHz): $\delta$ (ppm)=5.2-5.3 (m, 0.44 H, sugar proton), 4.9-5.1 (m, 1.51H, sugar proton), 3.7-3.8 (m, 19.01 H, sugar proton), 3.3-3.4 (m, 6.43 H, sugar proton), 3.1-3.2 (m, 11.82, sugar proton), 2.93-2.94 (m, 2.23 H, PIMA proton), 2.6-2.7 (m, 5.84 H, PIMA proton), 2.2-2.5 (broad, 4.91 H, PIMA proton), 1.8-2.1 (broad, 3.83 H, PIMA proton), 1.4-1.6 (broad, 2.52 H, PIMA proton), 1.8-1.2 (m, 18.04 H, PIMA proton), 0.9-1.0 (m, 23.77 H, PIMA proton). Total sugar protons: total PIMA protons=34.31:65.7=0.52.

Example 4

Time Dependent Loading Efficiency of PIMA-GA-CDDP

Method: PIMA-GA conjugate (50 mg, 0.004 mmol) was dissolved in 1 mL dd-water followed by the addition of $(NH_2)_2Pt(OH)_2$ (3 mL, 0.057 mmol). The reaction was stirred at room temperature for 48 h. 200 $\mu$L of aliquots were taken out from the reaction mixture after each predetermined time points (5 h, 31 h and 48 h). The aliquots were filtered through Microcon centrifugal filter device having regenerated cellulose membrane of 3000 MWCO to separate the PIMA-GA-CDDP conjugate. The polymer was washed thoroughly (200 $\mu$L×2) with dd-water to remove any platinum reagent. The platinum content in polymer was determined by the method described before.

Figure 9:
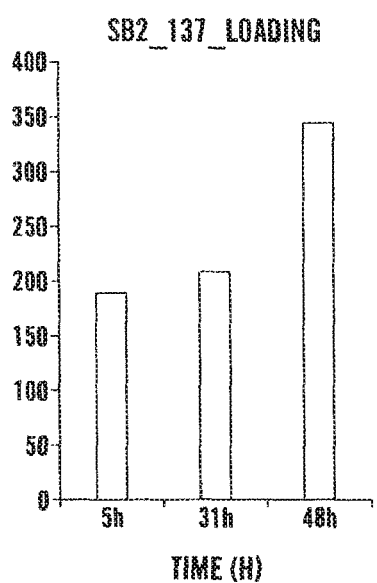
FIG. 9 is a graph showing the amount of platination of the polymer quantified using a uv-vis spectroscopy method.

Result: The change in Pt-loading efficiency in PIMA-GA conjugate was determined by the ability of conjugating 1,2-phenylenediamine with Pt giving rise to UV-VIS spectra at wavelength $\lambda$=706 nm. Neither the polymer nor 1,2-phenyldiamine has any characteristic peak at this wavelength. How the Pt-content changes with time in the reaction between PIMA-GA and hydroxy-platin was monitored by UV-VIS spectra. At different pre-determined time points (5 h, 31 h and 48 h) 200 $\mu$L of aliquots were taken out from the reaction mixture and the Pt-loading in the polymer conjugate was determined. FIG. 9 shows that loading of platinum in the polymer conjugate increases with time from 190 □g/mg (5 h) to 210 □g/mg (31 h) and reaches maximum 347 □g/mg at 48 h. This indicates almost 100% of the Pt is complexed with the polymer at this time point as the maximal predicted loading is 37.5% per polymer unit, and we attain 34.7% Pt per polymer.

Example 5

Rational Optimization of the Polymer Based on Structure-activity Relationship In order to improve efficacy of the nanoparticles, the inventors derivatized one arm of each monomer of the polymer with biocompatible glucosamine to generate PIMA-glucosamine conjugate (PIMA-GA) (FIG. 11B). This converted the dicarboxylato bonds with Pt to a monocarboxylato bond and a coordinate bond, which can release Pt more easily given that a coordinate bond is less stable than a monocarboxylato linkage (FIG. 11B).

Nuclear magnetic resonance (NMR) characterization of the Pt environment revealed that complexation of PIMA-GA and cisplatin in an acidic pH (pH 6.5) generated an isomeric state [PIMA-GA-Cisplatin (O->Pt)] (8) characterized by the monocarboxylato and a O->Pt coordination complex as characterized by a single Pt NMR peak at −1611.54 (FIG. 11B). Interestingly, complexing the cisplatin with PIMA-GA at an alkaline pH (pH 8.5) favored the formation of an isomeric PIMA-GA-Cisplatin (N->Pt) complex (10), where the Pt is complexed through a monocarboxylato and a more stable N->Pt coordinate bond characterized by a unique peak at −2210 (FIG. 11B). Excitingly, the existing of these two pH-dependent states allowed the inventors to further dissect the impact of Pt environment, specifically the leaving groups, on the biological efficacy.

Figures 12A, 12B:
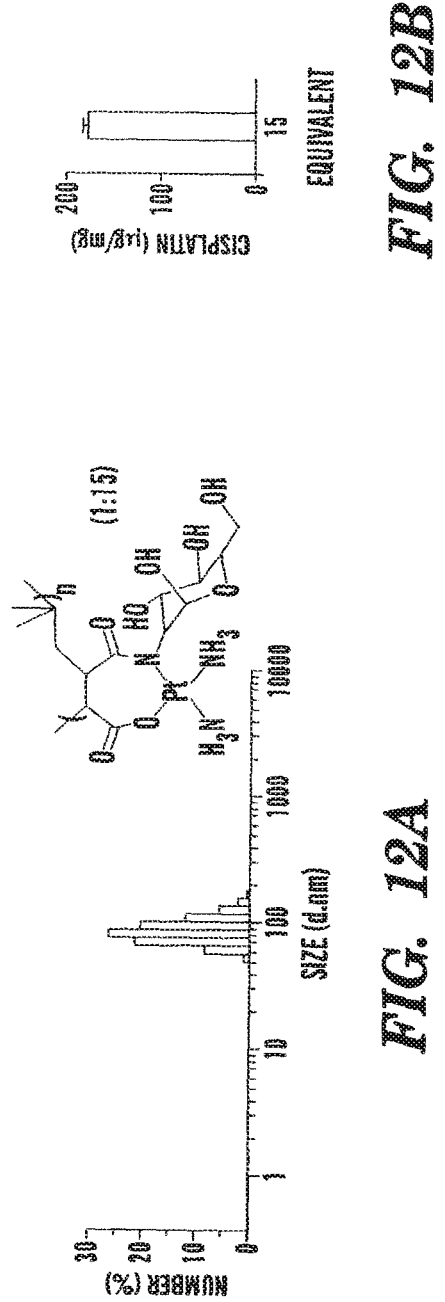
FIGS. 12A and 12B show characterization of cisPt-NP. Increasing the number of Pt on a PIMA (n=40) backbone increased the size of nanoparticle formed. At an optimal Pt to polymer ratio, the inventors obtained nanoparticles smaller than 150 nm, the size cut-off below which enables preferential homing to tumors.

The complexation of cisplatin to PIMA-glucosamine (PIMA-GA) polymer at a ratio of 15:1 resulted in self assembly into nanoparticles in the desired narrow size bandwidth of 80-150 nm as confirmed by high-resolution transmission electron microscopy (data not shown) and DLS (FIG. 12A). Furthermore, the inventors achieved a loading of 175±5 μg/mg of polymer (FIG. 12B), which is significantly higher than can be achieved using traditional nanoparticle formulations (Avgoustakis K, Beletsi A, Panagi Z, Klepetsanis P, Karydas A G, Ithakissios D S. PLGA-mPEG nanoparticles of cisplatin: in vitro nanoparticle degradation, in vitro drug release and in vivo drug residence in blood properties. J Control Release. 2002 Feb. 19; 79(1-3):123-35).

Example 6

Characterizing the Uptake and Efficacy of Nanoparticles in Vitro

Figure 15:
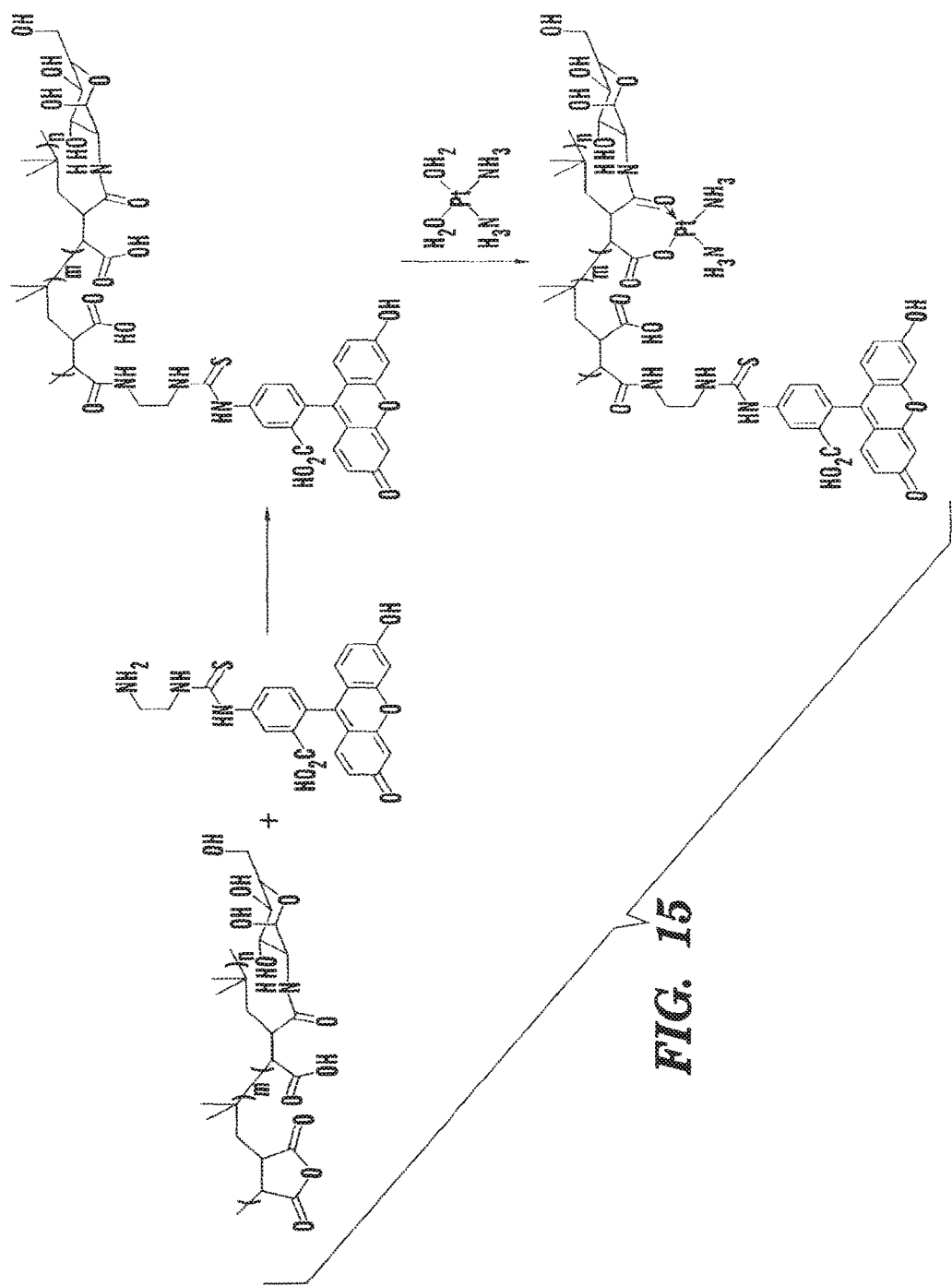
FIG. 15 is a schematic showing the labeling of the PIMA-GA polymer with FITC to enable the tracking of cellular uptake of the nanoparticles.

Tagging the polymer with fluorescein (FIG. 15) enabled the temporal tracking of uptake of the nanoparticles into the cells, which were co-labeled with a lysotracker-red dye to label the endolysosomal compartments. A rapid uptake of the nanoparticles was observed in the LLC cells within 15 min of treatment with internalization into the endolysosomal compartment as evident by colocalization of the FITC-nanoparticles and the Lysotracker-Red dye (data not shown). In contrast, the uptake into 4T1 cells was delayed, with internalization into the endolysosomal compartment evident only after 2 hours post-incubation. Over a 12 hour period, the fluorescent signals from the lysosomal compartment and the FITC-conjugated dissociate, suggesting a cytosolic distribution of the polymer after processing within the lysosome (data not shown).

Figure 13A:
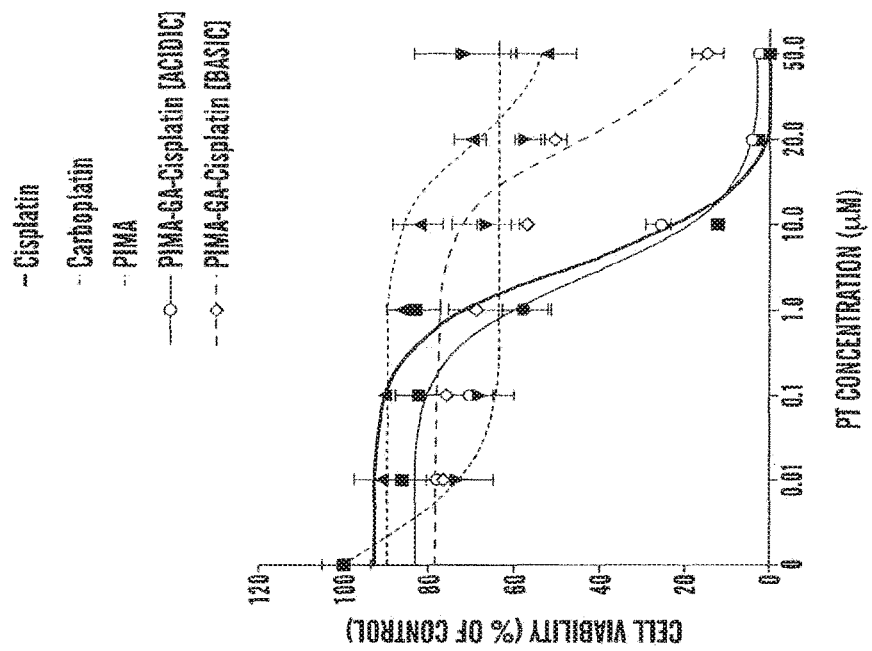
Figure 13B:
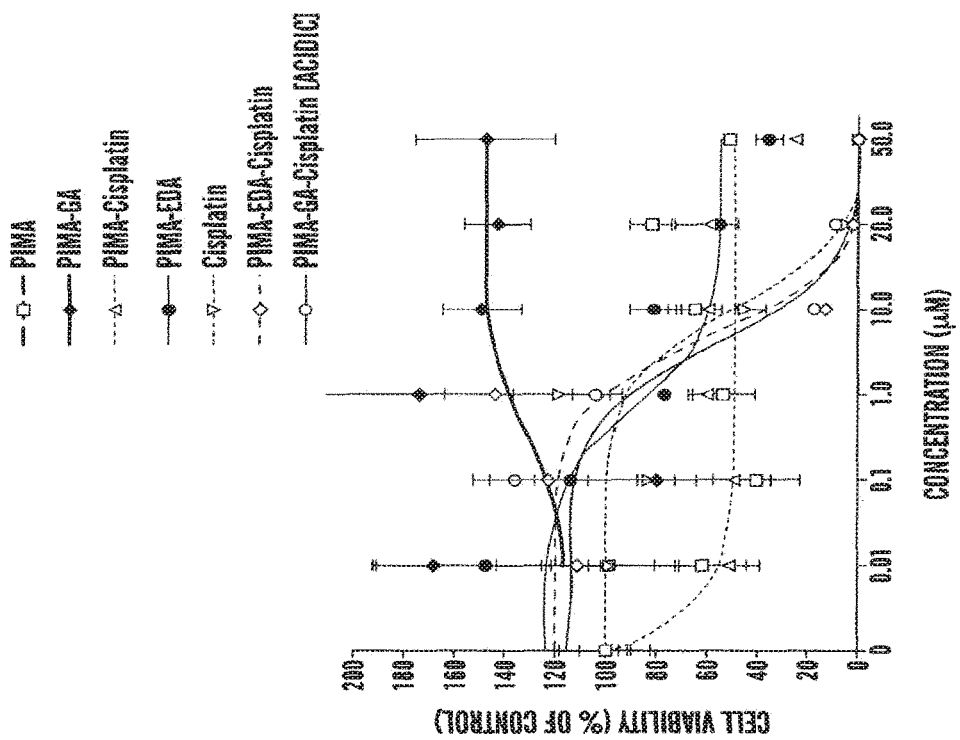
Figure 13F:
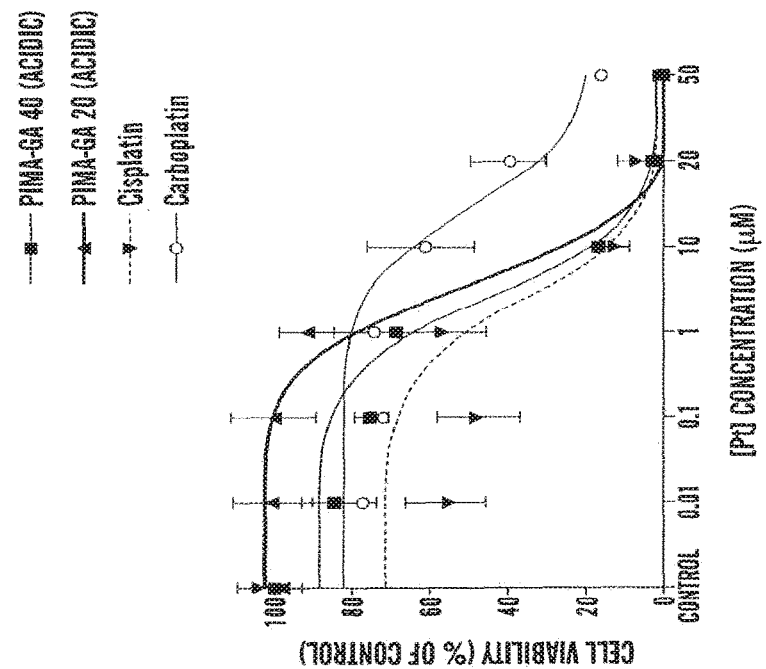
Figure 13E:
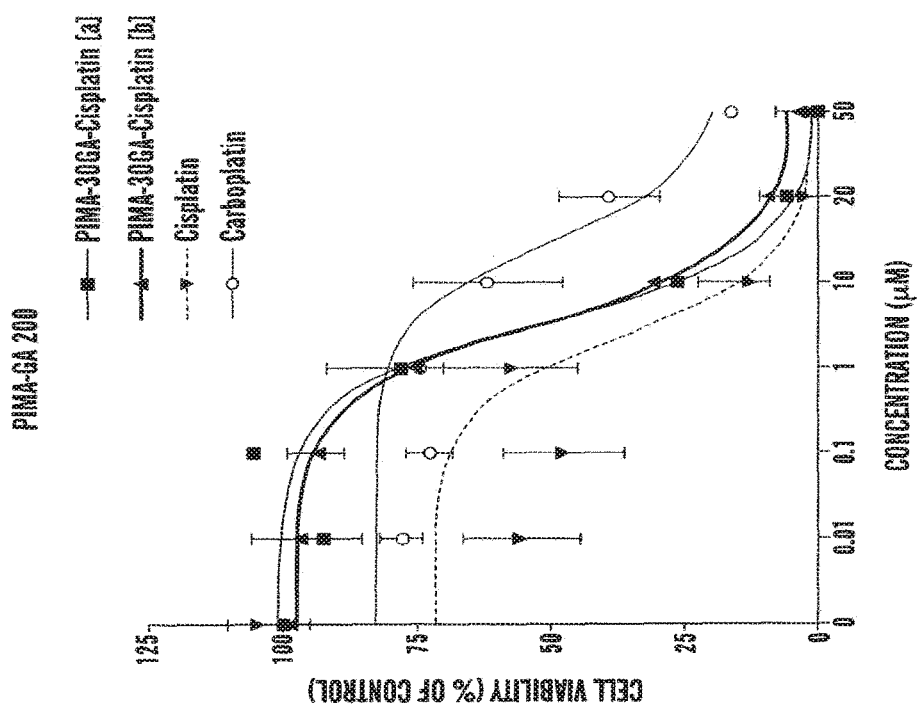
Figure 14J:
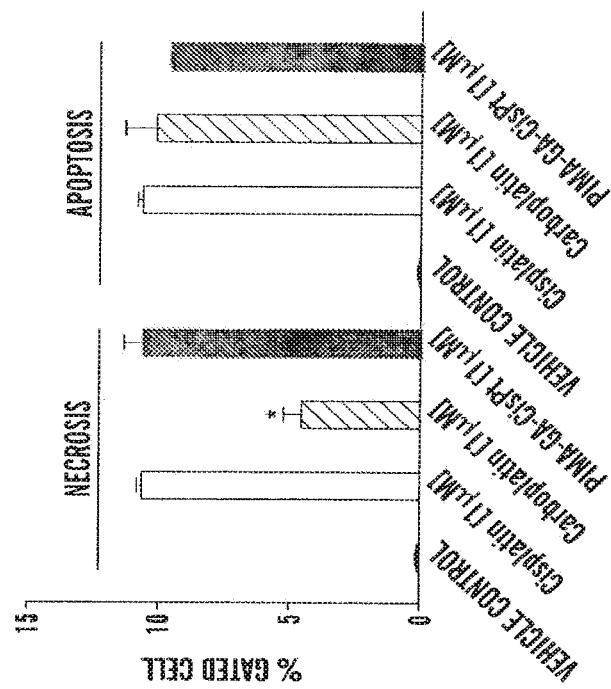
Figure 14I:
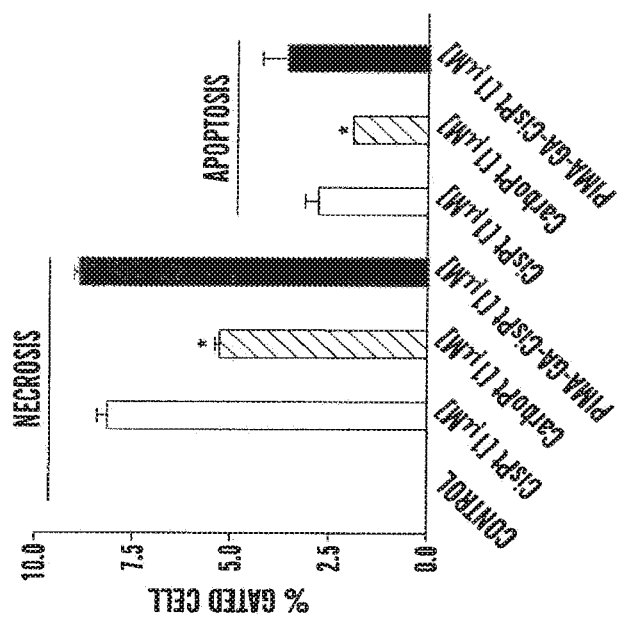

To test the efficacy of the PIMA-GA-cisplatin nanoparticles in vitro, the inventors performed cell viability assays using Lewis lung carcinoma (LLC) and 4T1 breast cancer cell lines. Cell viability was quantified using a MTS assay at 48 hours post-incubation. Interestingly, the LLC cells (FIG. 13A) were more susceptible to cisplatin-nanoparticles than the 4T1 breast cancer cells (FIG. 13B). Excitingly, PIMA-GA-cisplatin (O->Pt) nanoparticles (8) demonstrated significant LLC cell kill with IC50 values (4.25±0.161M) similar (P>0.05) to cisplatin (IC50=3.87±0.37 μM), and superior to carboplatin (IC50=14.75±0.38 μM), which supports the hypothesis that the rate of aquation is critical for efficacy (FIG. 13A-F). A similar efficacy was observed when the inventors replaced glucosamine with ethylene diamine, which creates a similar Pt complexation environment as glucosamine (FIG. 13A). This was additionally supported by the observation that PIMA-GA-cisplatin (N->Pt) nanoparticles (IC50=6.36±0.19 μM) were significantly less active than cisplatin, suggesting that the platinum environment is critical in defining the rate of aquation. To further validate the role of complexation environment, the inventors generated PIMA-GA(20), where only 20 of the 40 monomers comprising a PIMA polymer were derivatized with glucosamine, thereby introducing dicarboxylato bonds and reducing the monocarboxylato plus coordinate bonds that complex Pt to PIMA-GA. As shown in FIG. 13F, the concentration-efficacy curve shifts to the right with PIMA-GA(20)-cisplatin (EC50=5.85±0.13 μM) as compared with PIMA-GA-cisplatin (O->Pt) nanoparticles, where all the 40 monomers are derivatized with glucosamine. Empty PIMA-GA polymer had no effect on the cell viability. Table 1 summarizes the EC50 values.

As shown in FIG. 13A, while the polymer alone induced cell death at the highest concentrations, complexation of cisplatin significantly shifted the concentration-effect curve to the left, indicating that the PIMA-cisplatin nanoparticle induces cell kill. However, even at a concentration of 50 uM, the PIMA cisplatin failed to induce complete cell kill. In contrast, cisplatin exerts complete cell kill at a concentration greater than 20 uM. This reduction in the efficacy of palatinate when complexed with PIMA can be explained by the dicaroboxylateo linkage between the platinum and the maleci acid monomers, which tightly binds the Pt similar to the linkage that exists in carboplatin, which similarly is less efficacious than cisplatin.

Labeling the cells for expression of phosphatidylserine on the cell surface, revealed that the cisplatin treatments could induce apoptotic cell death, with LLCs being more susceptible than 4T1 cells (FIG. 14A-14J).

TABLE 1

| EC50 values for various complexes | |
|---|---|
| | EC50 (μM) |
| PIMA30: PIMA-GA-Cisplatin [acidic] | 5.29 ± 0.11 |
| PIMA30: PIMA-GA-Cisplatin [basic] | 6.84 ± 0.14 |
| Cisplatin | 3.87 ± 0.37 |
| Carboplatin | 14.75 ± 0.38 |
| PIMA40-200: PIMA-GA-Cisplatin [acidic] | 4.25 ± 0.16 |
| PIMA40-200: PIMA-GA-Cisplatin [basic] | 6.36 ± 0.19 |
| PIMA-GA20-Cisplatin [acidic] | 5.85 ± 0.13 |

Example 7

The Release of Active Cisplatin from Nanoparticle is pH-dependent

Figure 16:
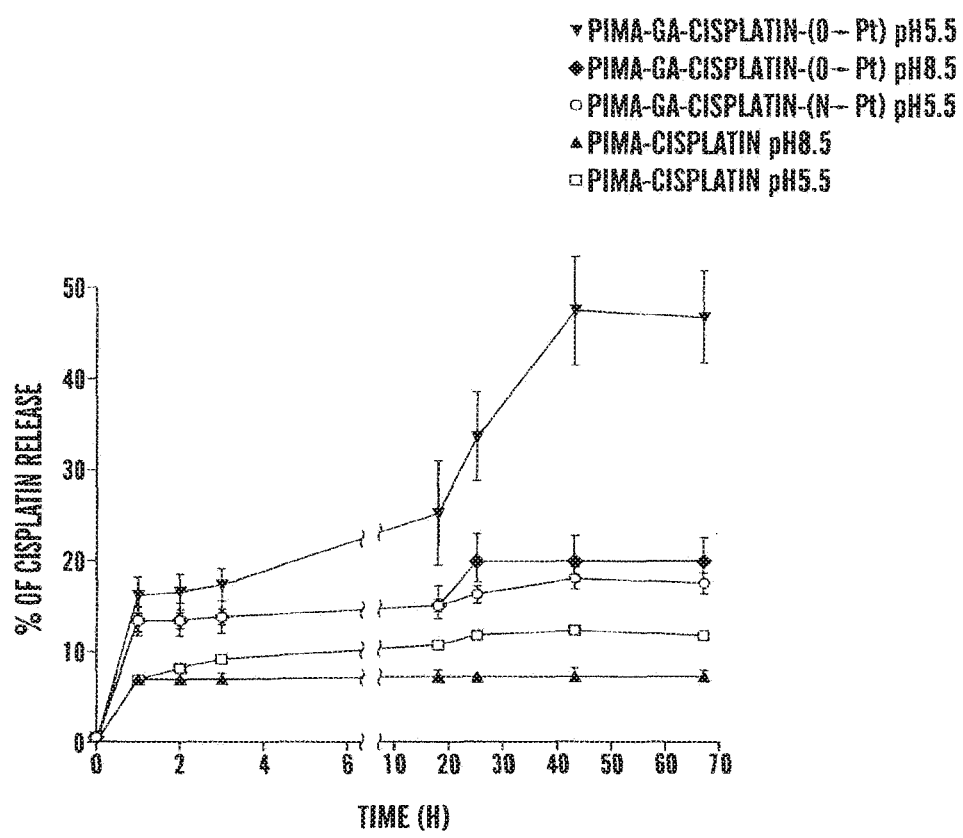
FIG. 16 is a line graph showing the effect of pH and Pt complexation environment on release kinetics. The nanoparticles were incubated at pH 5.5 or pH8.5 in a dialysis bag, and release over time was quantified. The nanoparticles [PIMAGA-Cisplatin (O->Pt)] used were generated by complexing the polymer and cisplatin in an acidic pH [6.4] unless in the case of PIMA-GA-Cisplatin (Pt->N), where the complexation was carried out in a basic pH to generate the stable isomer [PIMA-GA-Cisplatin (N->Pt)]. The data shown are mean±SE from n=3.
Figure 17B:
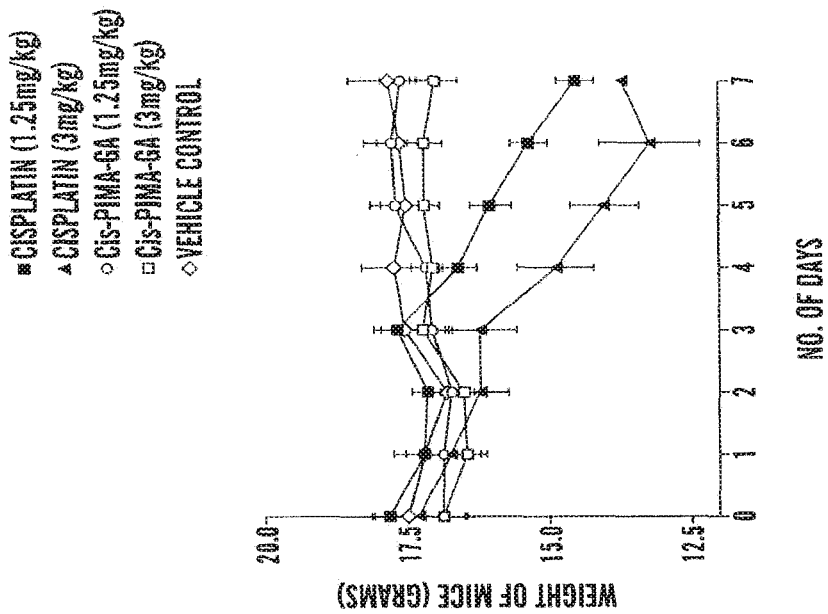
FIGS. 17A-17B are line graphs and FIGS. 17C-17D are bar graphs showing PIMA-GA-cisplatin nanoparticle exerts similar anti-tumor effect with reduced systemic toxicity compared to free cisplatin in a 4T1 breast cancer model. Line graphs show the effect of treatments on tumor volume (FIG. 17A) and body weight (FIG. 17B) over the treatment period. The animals were dosed thrice (shown by arrows on x-axis). Data shown are mean±SE, n=4-8. Bar graphs show the effect of treatment on the organ weight of spleen (FIG. 17C) and kidneys (FIG. 17D) as a marker for nephrotoxicity and hematological toxicity (n=4-6)*P<0.05 vs vehicle-treated group [ANOVA followed by Newman Keuls Post Hoc test]. Carboplatin [3 mg/kg] was used as a control.
Figure 17A:
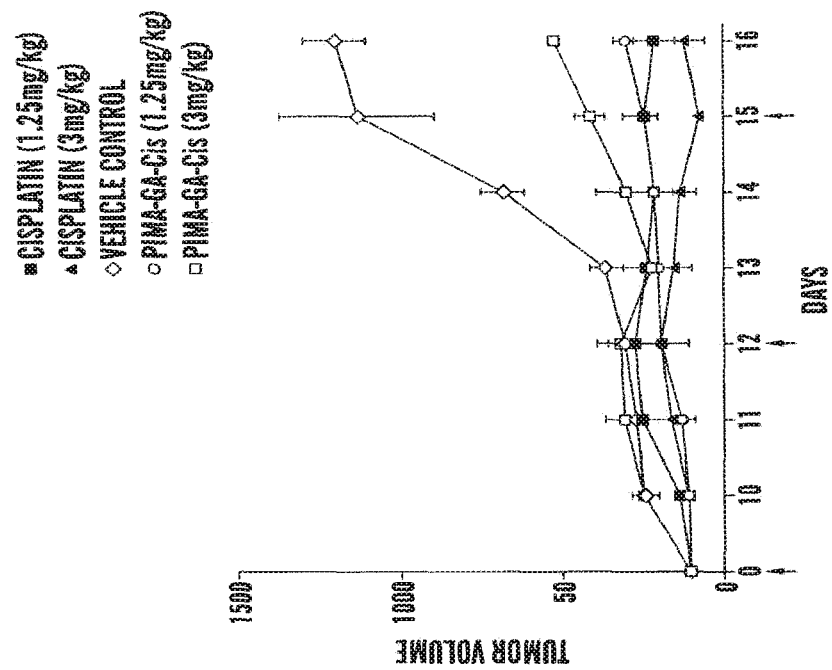
Figures 17C, 17D:
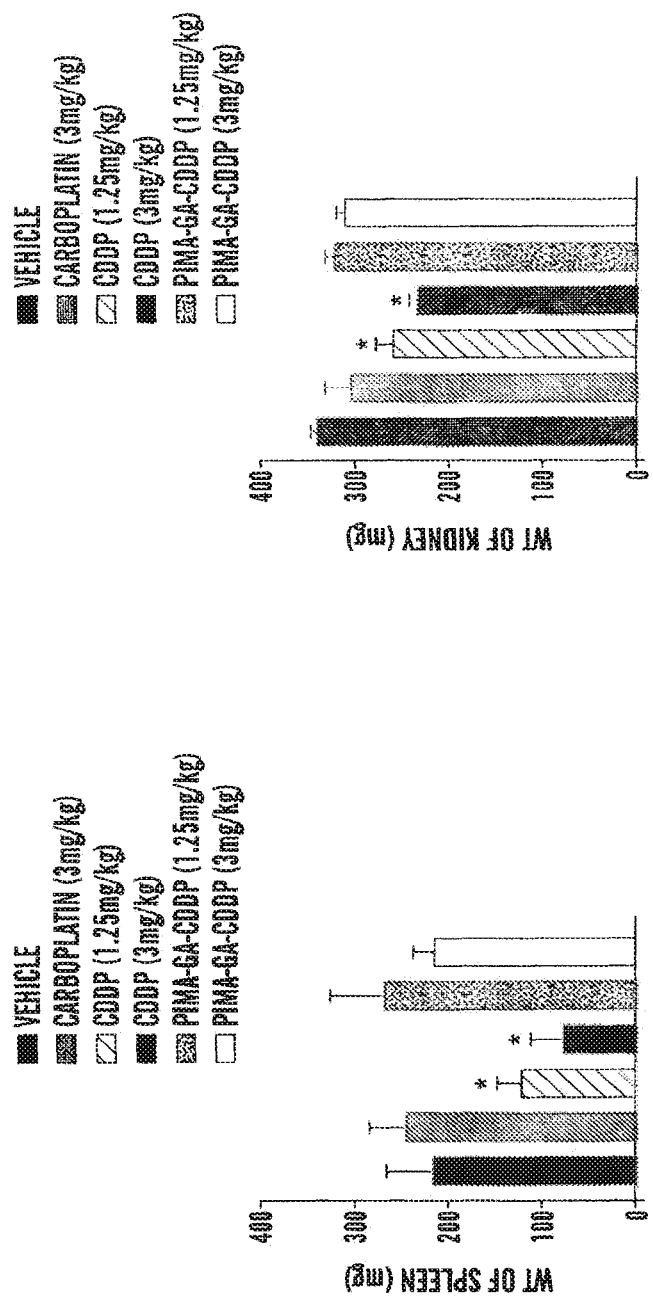

Given that the nanoparticles localized to the lysosomal compartment, the inventors tested the release of Pt from the nanoparticles at pH 5.5, mimicking the acidic pH of the endolysosomal compartment of the tumor (Lin, et al., Eur. J. Cancer, 2004 40(2):291-297). The inventors also selected pH8.5 as a reference pH in the alkaline range. As shown in FIG. 16, at pH5.5 PIMA-GA-cisplatin (O->Pt) nanoparticles resulted in a sustained but significant release of cisplatin monitored over a 70 hour period. In contrast the release at pH8.5 was significantly lower, indicating a pH-dependent release of Pt. Interestingly, PIMA-GA-cisplatin (N->Pt) released significantly lower amounts of Pt even at pH5.5, consistent with the fact that the N->Pt coordinate bond is stronger than the O->Pt linkage. As expected, the inventors observed that PIMA-cisplatin nanoparticles exhibited significantly lower rates of Pt release as compared with both PIMA-GA-cisplatin (N->Pt) and PIMA-GA-cisplatin (O->Pt) as the Pt is held by more stable dicarboxylato bonds instead of a monocarboxylato and a coordinate bond.

Example 8

Nanoparticle Induces Tumor Growth Delay and Regression with Reduced Nephrotoxicity As PIMA-GA-cisplatin (O->Pt) nanoparticles exhibited the desired release rates for platinum and also exhibited in vitro efficacy comparable to cisplatin, the inventors validated the therapeutic efficacy of the nanoparticles in vivo. They randomly sorted mice bearing established Lewis lung carcinoma or 4T1 breast cancer into five groups respectively and treated each group with three doses of (i) PBS (control); (ii) Cisplatin (1.25 mg/kg); (iii) Cisplatin (3 mg/kg); (iv) PIMA-GA-Cisplatin (O->Pt) nanoparticles (1.25 mg/kg); (v) PIMA-GA-Cisplatin (O->Pt) nanoparticles (3 mg/kg). The mice injected with PBS formed large tumors by day 16 (day after the last injection), and consequently, were euthanized. The animals in the other groups were also sacrificed at the same time point to evaluate the effect of the treatments on tumor pathology. As shown in FIG. 5A-F, cisplatin induced dose-dependent tumor inhibition, and at a dose equivalent to 1.25 mg/kg of cisplatin, administration of the nanoparticle formulation resulted in greater inhibition of lung carcinoma progression as compared with the free drug. However, at a dose equivalent to 3 mg/kg, free cisplatin resulted in a significant reduction in body weight indicating systemic toxicity. In contrast, animals treated with nanoparticles equivalent to 3 mg/kg of cisplatin exhibited weight gain, although tumor inhibition was similar in both treatment groups (data not shown). Furthermore, necropsy revealed that treatment with free cisplatin resulted in a significant reduction in the weights of kidney and spleen (FIGS. 5D and 5E), indicating nephrotoxicity and hematotoxicity consistent with previous reports. Excitingly, cisplatin nanoparticles had no effect on the weights of the kidneys, and reduced spleen size only at the highest dose (FIGS. 5D and 5E). This was further validated by pathological analysis of kidney H&E stained cross-sections, which revealed significant tubular necrosis in the animals treated with free cisplatin as compared with cisplatin nanoparticle. To elucidate the mechanism underlying tumor inhibition, the inventors labeled the tumor cross sections for TUNEL, which revealed a significant induction of apoptosis following treatment with both free cisplatin and PIMA-GAcisplatin(O->Pt) nanoparticles (data not shown). Interestingly, labeling the kidney sections for TUNEL demonstrated significant apoptosis in the animals treated with free cisplatin as opposed to minimal nephrotoxicity in the nanoparticle-treated group (data not shown). Indeed, biodistribution studies using inductively coupled plasma-spectrometry (ICP) revealed that the concentration of Pt in the kidney following administration of the cisplatin nanoparticle is 50% of that attained following administration of free drug (FIG. 5F), which can explain the reduction in nephrotoxicity.

Figure 5B:
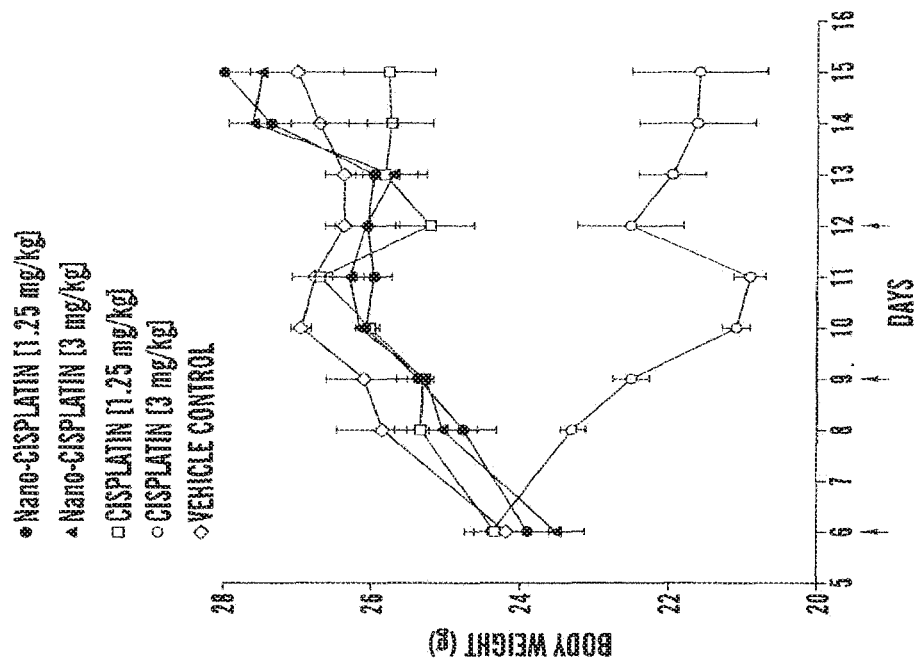
FIGS. 5A-5B are line graphs and FIGS. 5C-5F are bar graphs showing efficacy and toxicity profile of free and nanoparticle cisplatin in Lewis Lung carcinoma model. Tumors were induced by injecting LLC cells in c57/BL6 mouse. The effect of treatments on tumor volume (FIG. 5A) and body weight (FIG. 5B) over the treatment period is shown.
Figure 5A:
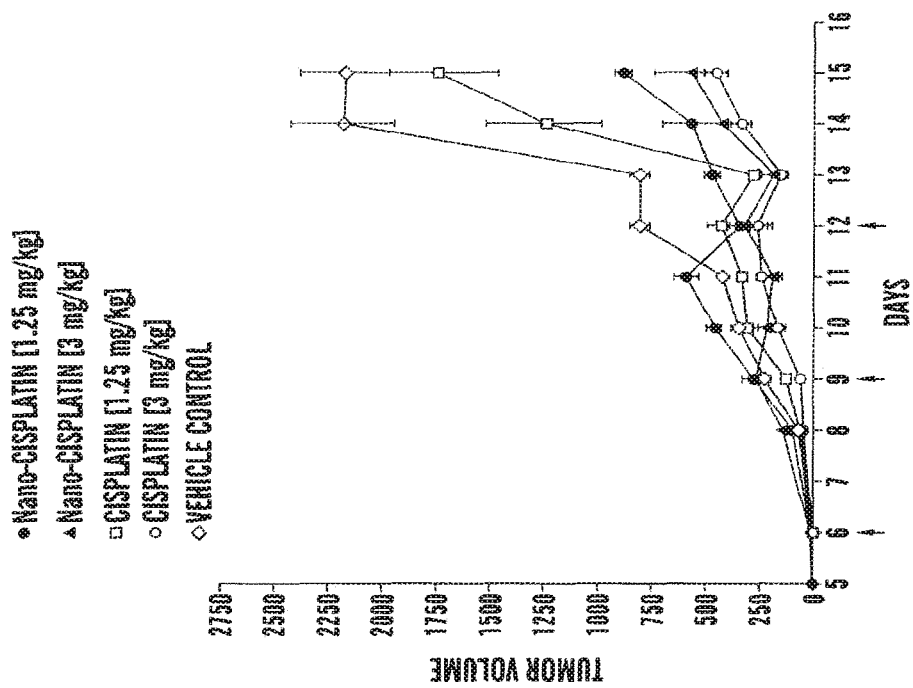
Figure 5C:
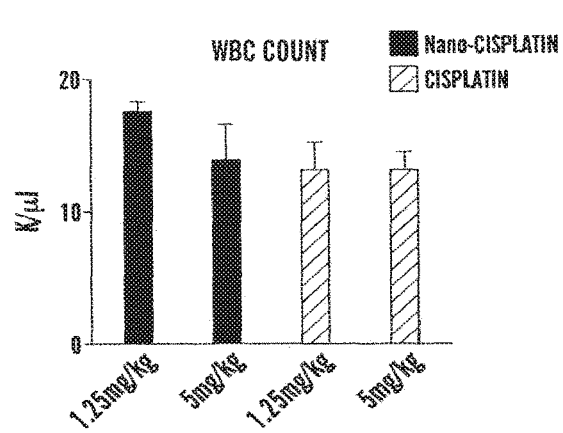
Figure 5F:
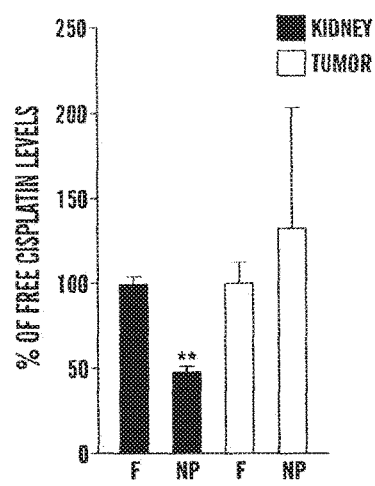
Figure 5D:
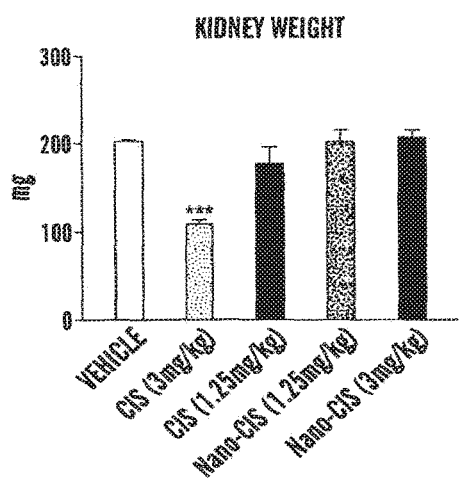
Figure 5E:
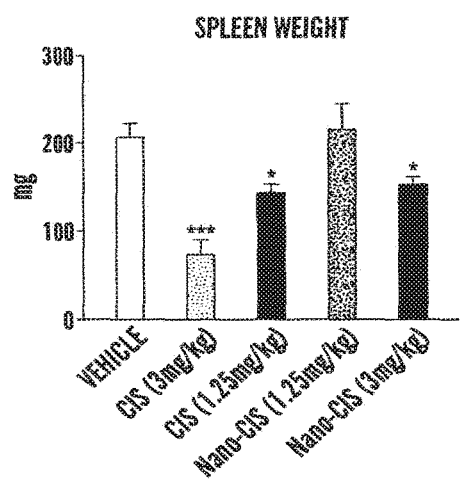
Figure 6:
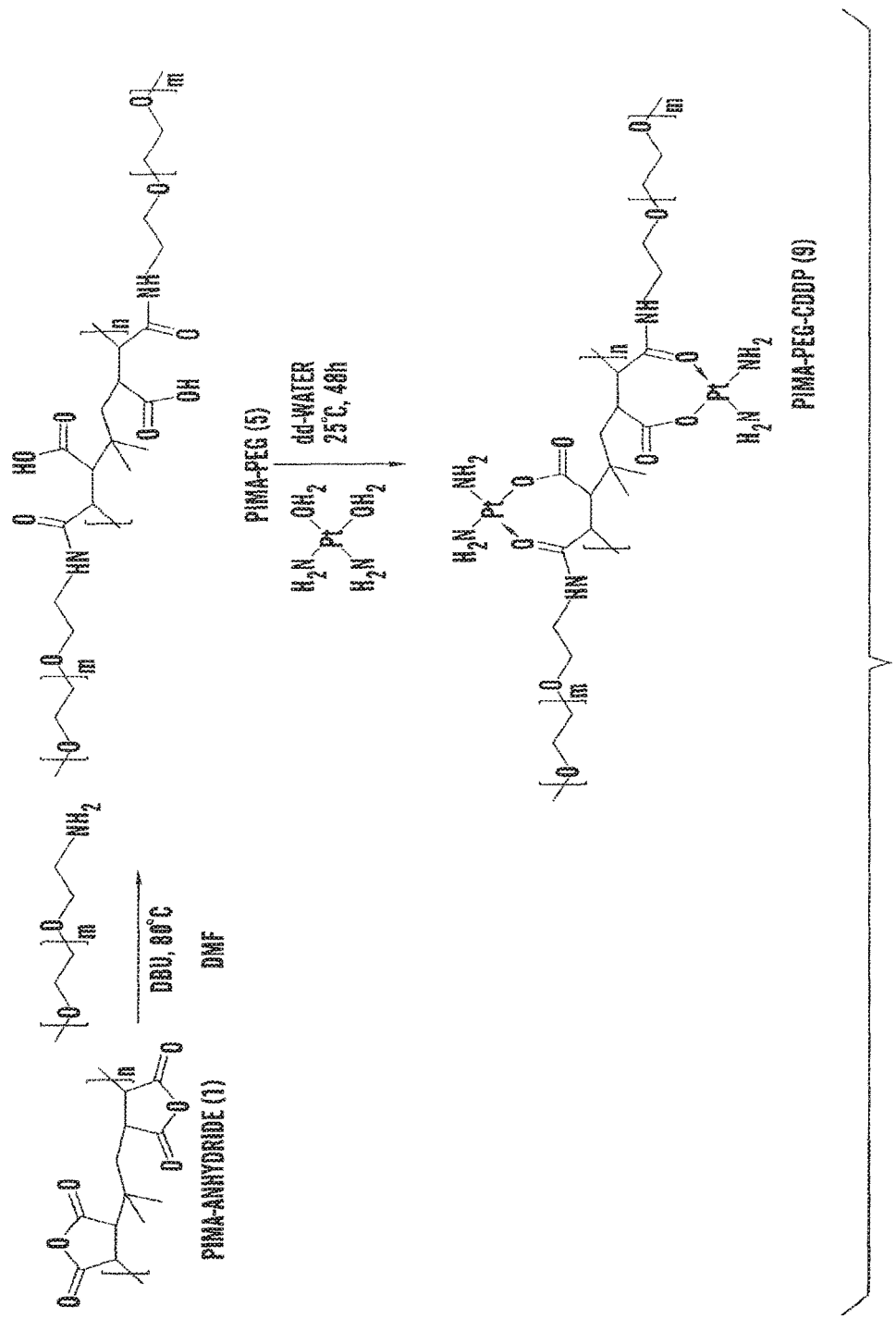
FIG. 6 is a scheme showing synthesis of PMA-GA-Cisplatin (8).
Figure 7:
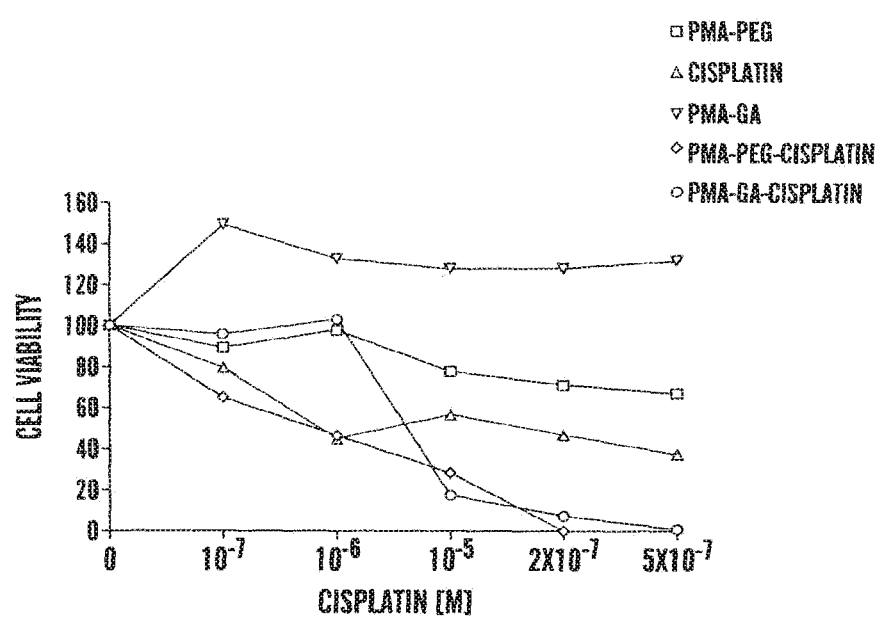
FIG. 7 shows the effect of PMA-PEG-Cisplatin on Lewis Lung Carcinoma. Cell were incubated for 48 hours with the drugs or vehicles and then tested for viability using an MTS assay.
Figures 8A, 8B:
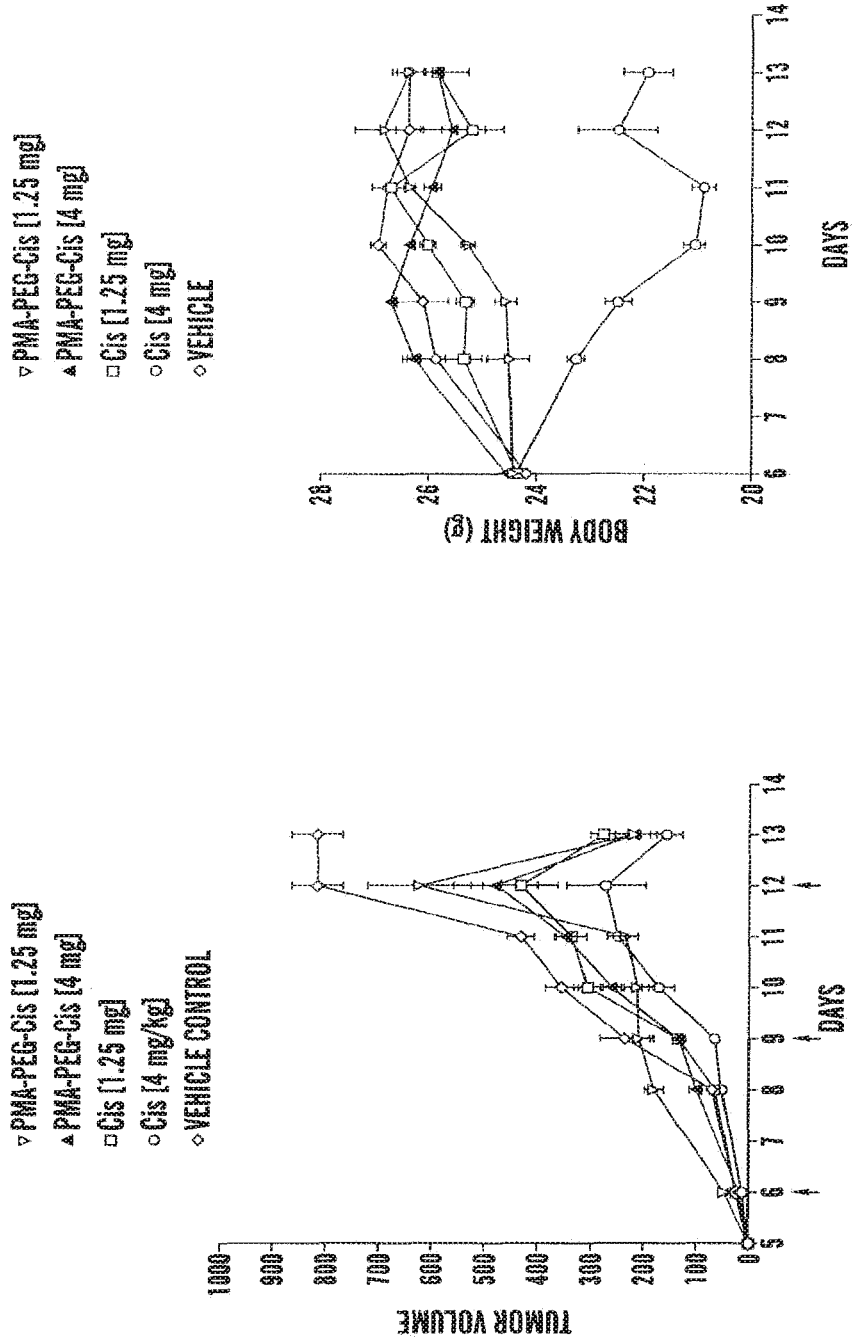
FIG. 8A-8B show the effect of different treatments on tumor growth and body weight in vivo respectively. Tumors were induced by injecting LLC cells in c57/BL6 mouse.

Treatment with cisplatin (1.25 mg/kg) exhibited only a minor tumor growth inhibition as compared with control; in contrast, treatment with nanoparticle-cisplatin at the same dose exerted a dramatic increase in the antitumor efficacy (FIG. 5A). This is consistent with the fact that nanoparticles enable a significantly higher concentration of the active agent to be attained within the tumor as compared to free drug[20]. At the higher dose, both the free drug and the nanoparticle achieved similar antitumor efficacy (FIG. 5A), which is potentially the theoretical limit of the drug. However, the free drug at this dose resulted in a greater than 20% loss of body weight (FIG. 5B), which is an indicator of non-specific toxicity. Indeed, it induced significant nephrotoxicity as seen by the loss of weight of the kidney (FIG. 5D). Furthermore, although the blood counts were not different between the various treatment groups (FIG. 5C), there was significant loss of weight of the spleen at the highest dose of the free cisplatin (FIG. 5E). In contrast, nanoparticle-cisplatin exhibited no such toxicity even at the highest dose, open up the possibility of dosing at higher levels or for longer time periods, both of which can dramatically impact antitumor outcomes. Furthermore, the ease of manufacturing, the low costs of materials and the increase in therapeutic efficacy and reduction of toxicity can become an example of nanotechnology impacting global health. Without wishing to be bound by theory, the increased therapeutic index can arise from a preferential accumulation of the nanoparticles in the tumors arising from the well-studied EPR effect, and circumventing the kidney as it exceeds the size limit for clearance, which in a previous study was shown to be less than 5 nm (Choi H S, Liu W, Misra P, Tanaka E, Zimmer J P, Itty Ipe B, Bawendi M G, Frangioni J V. Renal clearance of quantum dots. Nat Biotechnol. 2007; 25:1165-70).

Both free cisplatin and PIMA-GA-cisplatin(O->Pt) nanoparticles resulted in similar levels of tumor growth inhibition in the 4T1 breast cancer model (FIG. 17A-17D). Interestingly, both 1.25 mg/kg and 3 mg/kg free cisplatin induced a significant loss of body weight as compared with the cisplatin-nanoparticle treated groups. Consistent with the observations in the lung cancer model, while free cisplatin induced significant apoptosis in the kidney, the nanoparticle-cisplatin treated groups exhibited minimal apoptosis in the kidney but significant levels of apoptosis in the tumor.

Figure 18B:
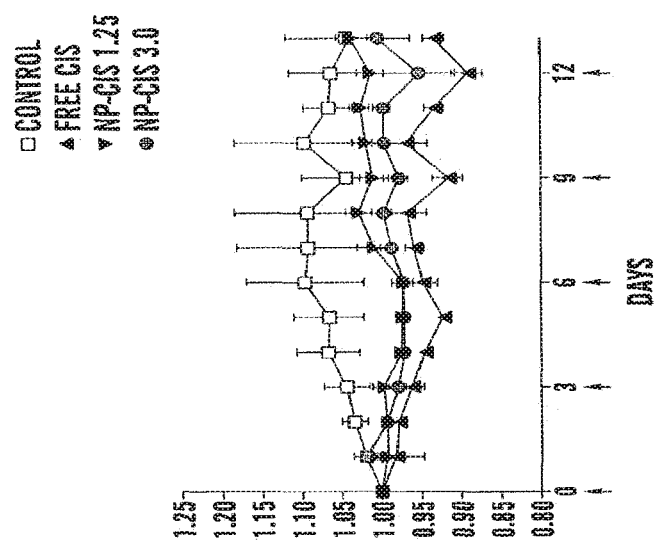
FIG. 18A is a bar graph and FIG. 18B is a line graph showing PIMA-GA-cisplatin nanoparticle inhibits tumor growth in a K-ras$^{LSL/+}$/Pten$^{fl/fl}$ h ovarian cancer model.
Figure 18A:
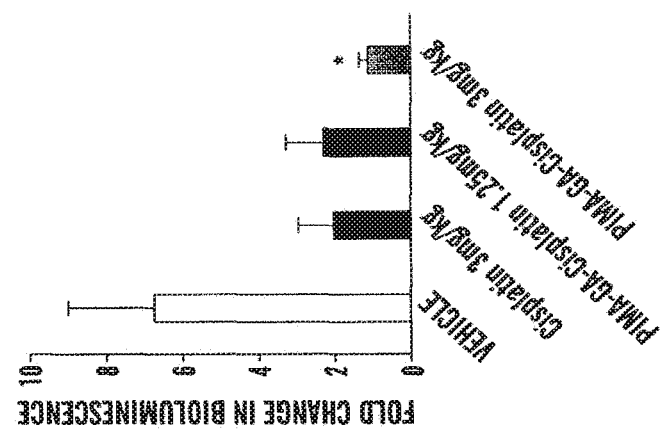

In addition to lung and breast cancer models, the inventors further evaluated the PIMA-GA-cisplatin(O->Pt) nanoparticle in an ovarian cancer model. Epithelial ovarian cancer is the deadliest malignancies of the female reproductive cycle. The discovery of frequent somatic PTEN mutations and loss of heterozygosity at the 10q23 PTEN locus in endometrioid ovarian cancer implicates a key role for PTEN in the etiology of this epithelial ovarian cancer subtype (Obata, K. et al. Frequent PTEN/MMAC1 mutations in endometrioid but not serous or mucinous epithelial ovarian tumors. *Cancer Res.* 58, 2095-2097 (1998) and Sato, et al., Cancer Res. 2000, 60: 7052-7056 and Sato, et al., Cancer Res. 2000, 60: 7052-7056). Similarly, K-RAS oncogene is also mutated in endometrioid ovarian cancer, albeit at a lesser frequency (Cuatrecasas, et al., Cancer (1998) 82:1088-1095). In a recent study, the combination of these two mutations in the ovarian surface epithelium was found to induce invasive and widely metastatic endometrioid ovarian adenocarcinomas with complete penetrance, making it a good model for mimicking human tumor progression. In this transgenic model vehicle-treated animals exhibited rapid tumor progression as quantified by luciferase expression. Treatment with the cisplatin nanoparticles resulted in a dose-dependent inhibition of tumor progression, with the lower dose equivalent to 1.25 mg/kg exerting a similar inhibition as a 3 mg/kg dose of free cisplatin (FIG. 18A). Treatment with the higher dose of cisplatin-nanoparticle (equivalent to 3 mg/kg of cisplatin) resulted in greater tumor inhibition without any significant loss of body weight as observed with an equidose of free cisplatin, which is approved for clinical use in ovarian cancer (FIG. 18B). Furthermore, TUNEL staining revealed significant apoptosis in the kidney at 3 mg/kg of free cisplatin while the cisplatinnanoparticles at equivalent Pt concentration did not induce apoptosis of the nephrons.

Example 9

Biodistribution of Cisplatin-nanoparticles Following Multiple Dosing

Figure 19A:
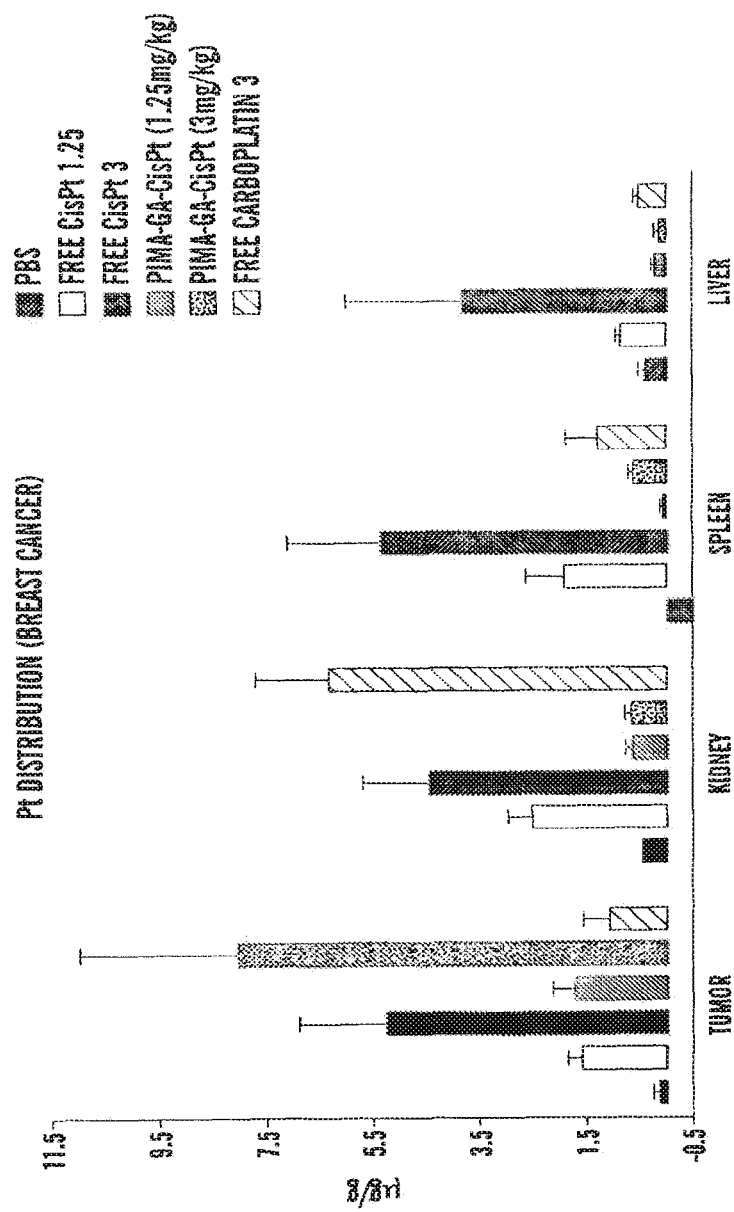
FIGS. 19A and 19B are bar graphs showing the distribution of Pt following administration of cisplatin, cisplatin-nanoparticle ([PIMA-GA-Cisplatin (O->Pt)] or carboplatin in breast cancer and ovarian cancer respectively. Treatment was administered as described in FIGS. 17A-D and 18A-B. The level of Pt in different tissues harvested following necropsy was quantified using inductively coupled plasma-spectrometry (ICP).
Figure 19B:
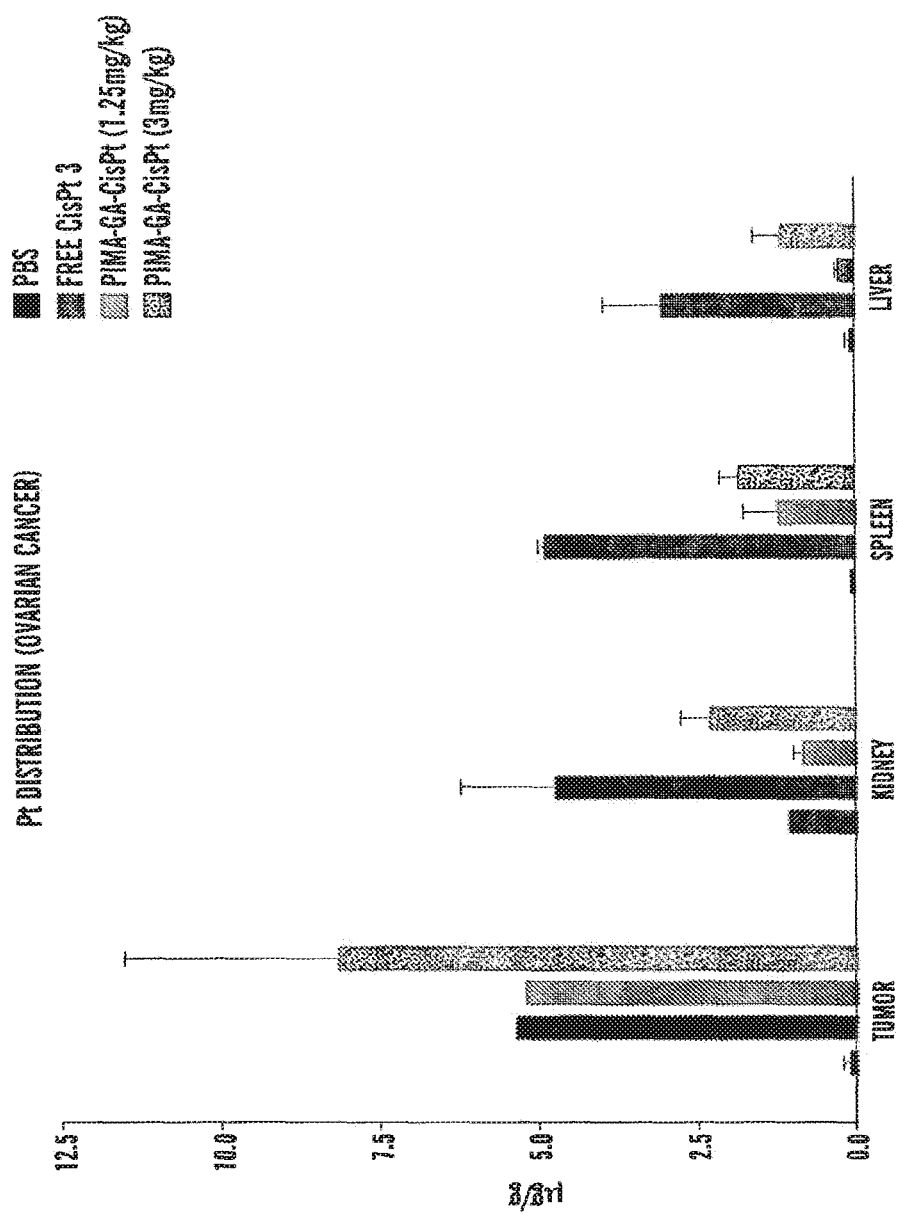
Figures 21A, 21B:
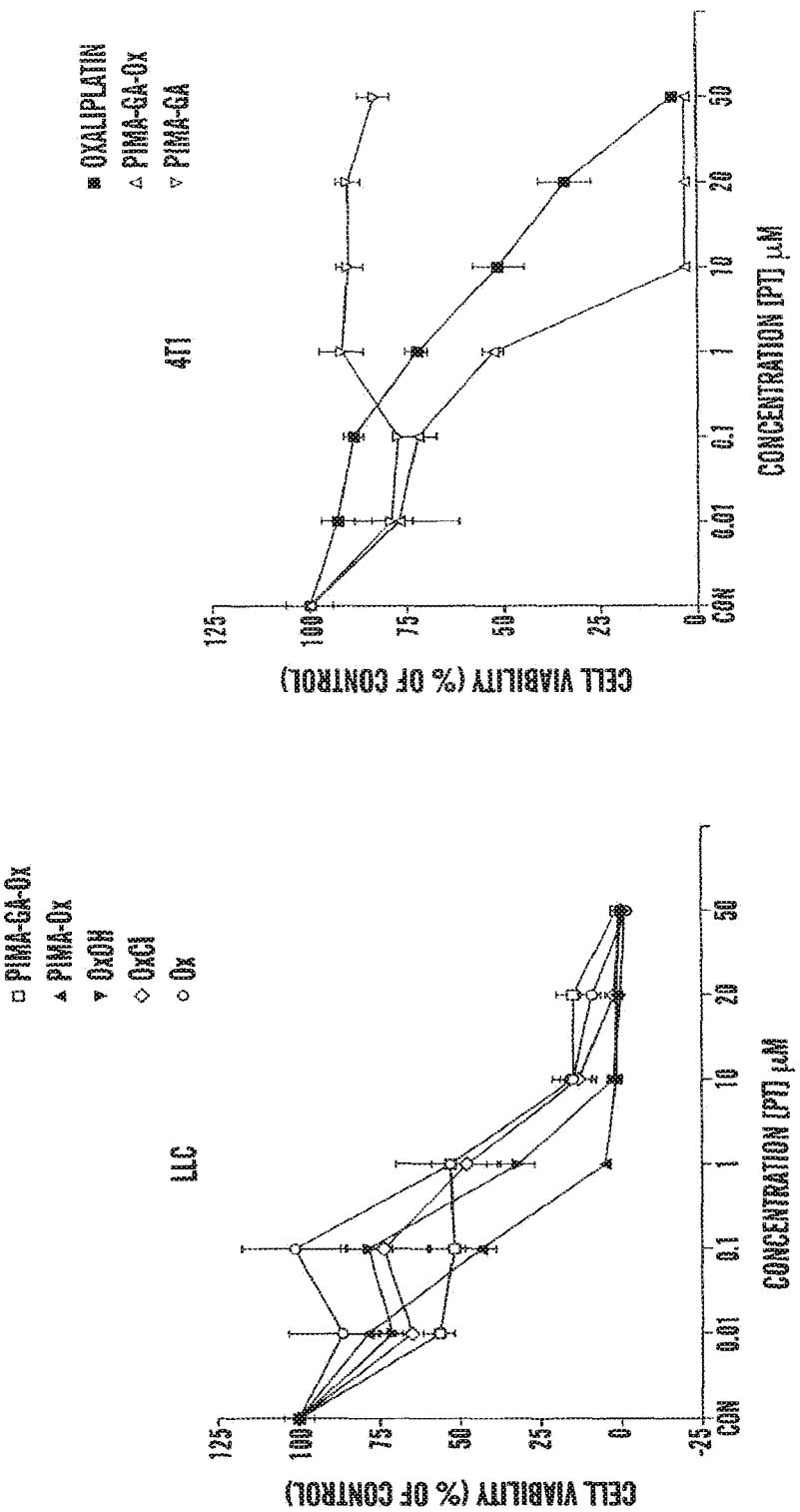
FIGS. 21A and 21B are line graphs showing the concentration-effect of different treatments on cellular viability as measured using MTS assay. Breast cancer cell line, Lewis lung cancer (FIG. 21A) and 4T1 (FIG. 21B) cell lines were used for this study. X-axis shows the equivalent concentrations of platinum. Where blank polymeric controls were used, dose of polymer used was equivalent to that used to deliver that specific dose of oxaliplatin in the complexed form. PIMA-GA-Ox refers to the isomer [PIMA-GA-Oxaliplatin (O->Pt)] formed under acidic complexation environment. The PIMA-GA-oxaliplatin curve shifted to the left, indicating that the nanoparticles are more effective than free oxaliplatin in anti-tumor efficacy.
Figures 22A, 22B:
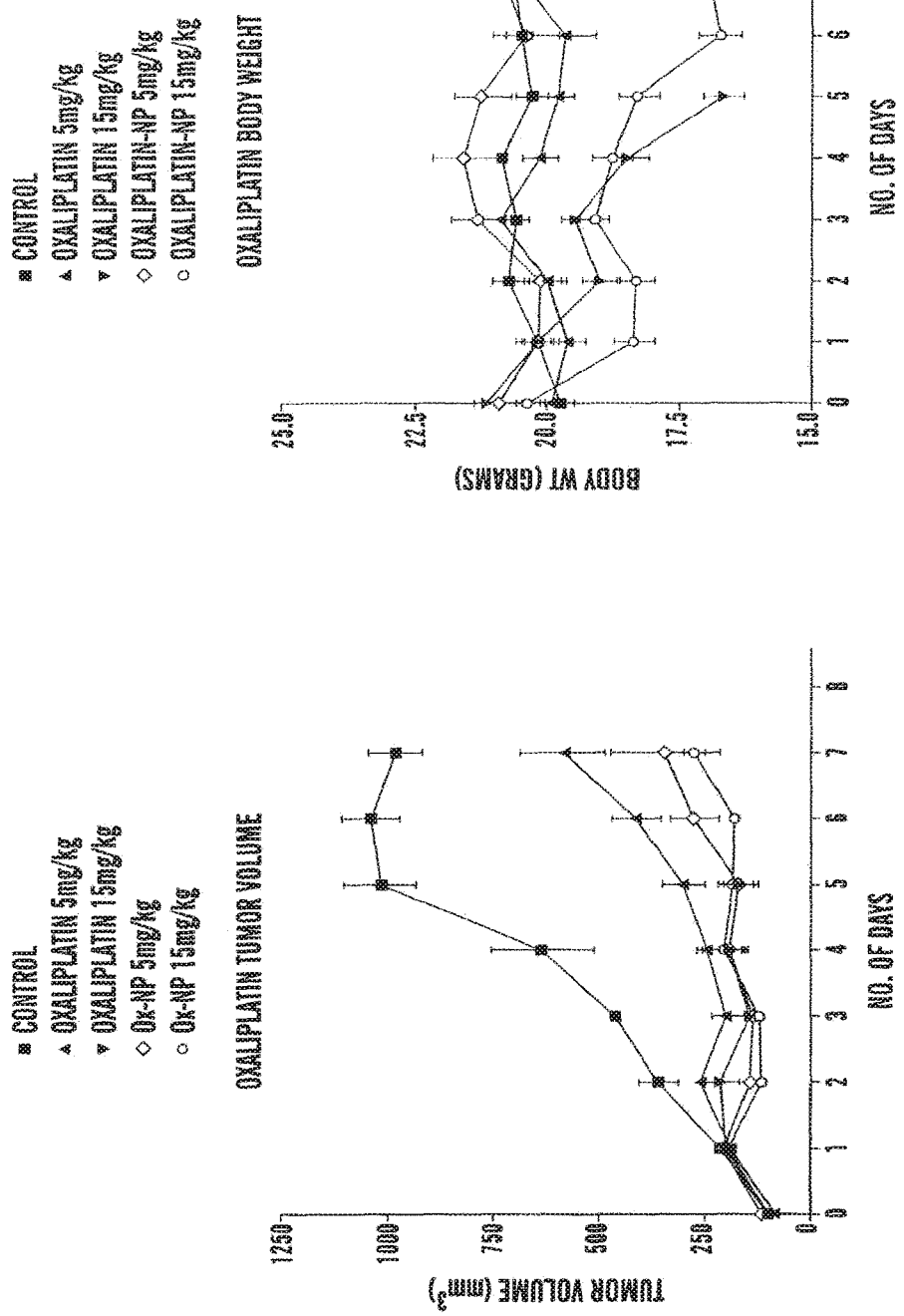
FIGS. 22A-22B are line graphs and FIGS. 22C-22E are bargraphs, showing PIMA-GA-oxaliplatin nanoparticle exerts similar anti-tumor effect with reduced systemic toxicity compared to free oxaliplatin in a 4T1 breast cancer model. Line graphs show the effect of treatments on tumor volume (FIG. 22A) and body weight (FIG. 22B) over the treatment period. The animals were dosed thrice. Data shown are mean±SE, n=4-8. Bar graphs show the effect of treatment on the weight of tumor (FIG. 22C), kidney (FIG. 22D), and spleen (FIG. 22E) as a marker for nephrotoxicity and hematological toxicity (n=4-6).
Figures 22C, 22D, 22E:
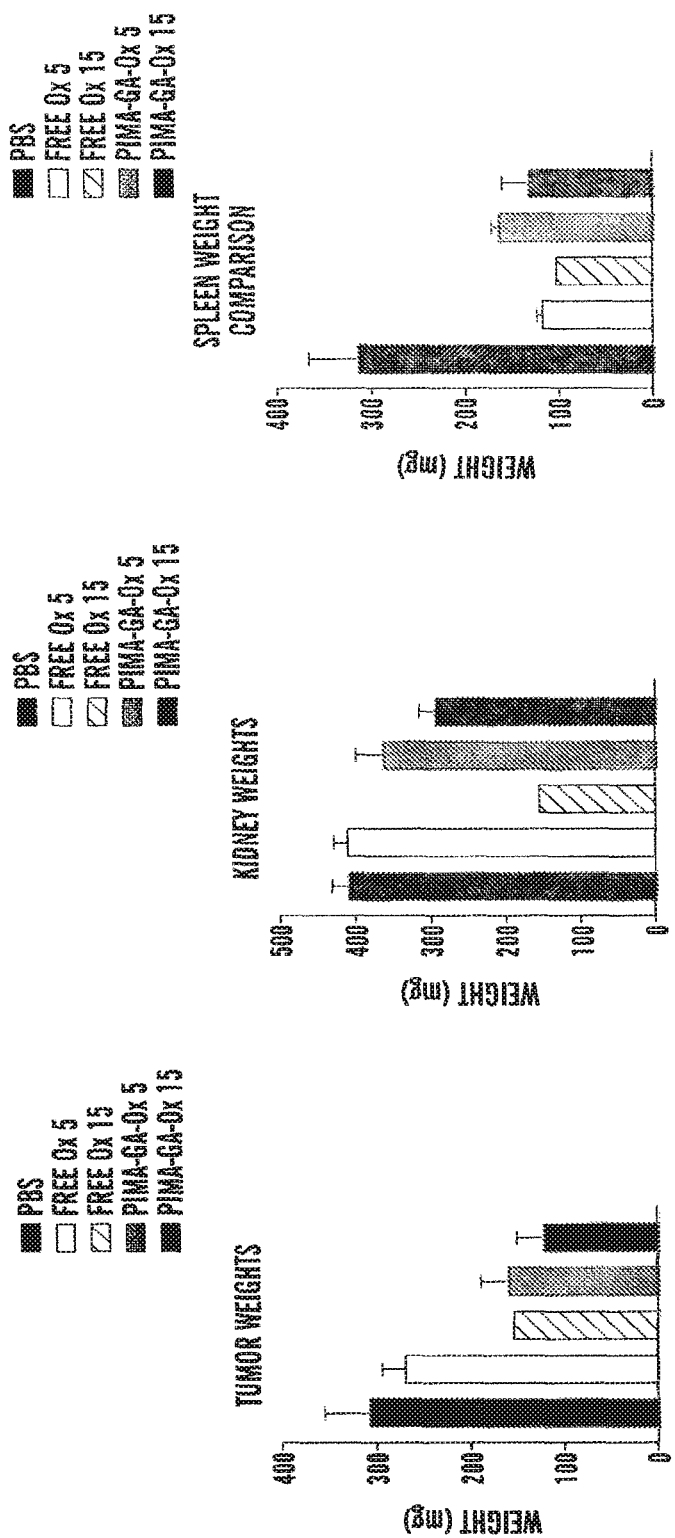
Figure 24:
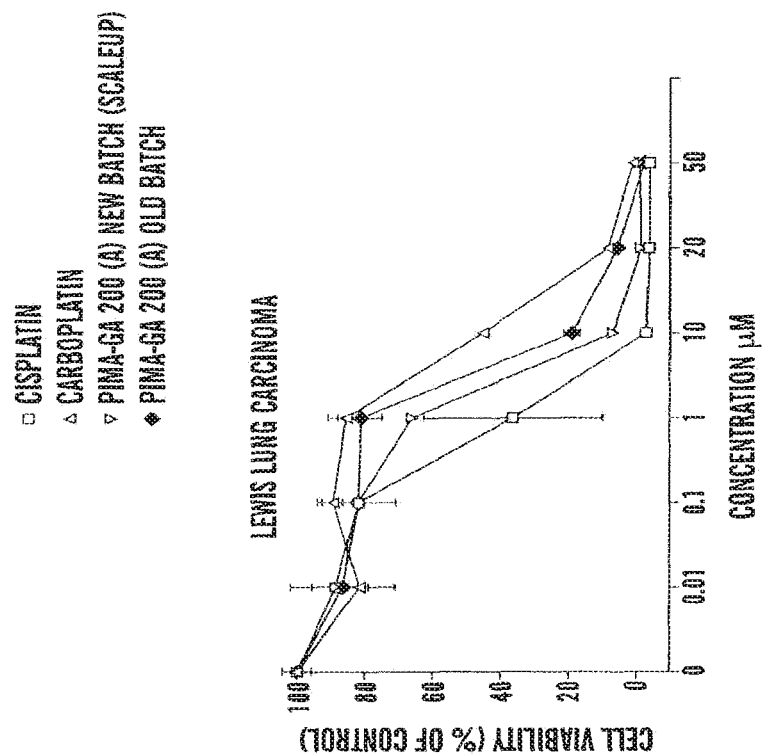
FIG. 24 is a line graph showing the effect of cisplatin, carboplatin and PIMA-GA-200(A) on cell viability.

To study the biodistribution of the cisplatin nanoparticles, the inventors harvested the tumors at the end of the multiple-dosing experiments, where each animal received three doses of free drug or the cisplatin nanoparticle. As shown in FIGS. 19A-19B, there was a preferential accumulation Pt in both breast and ovarian tumors when administered as a nanoparticle as opposed to when delivered as free cisplatin.

Example 10

Toxicity Assessment of Treatment with PIMA-GA-oxaliplatin

Figure 23:
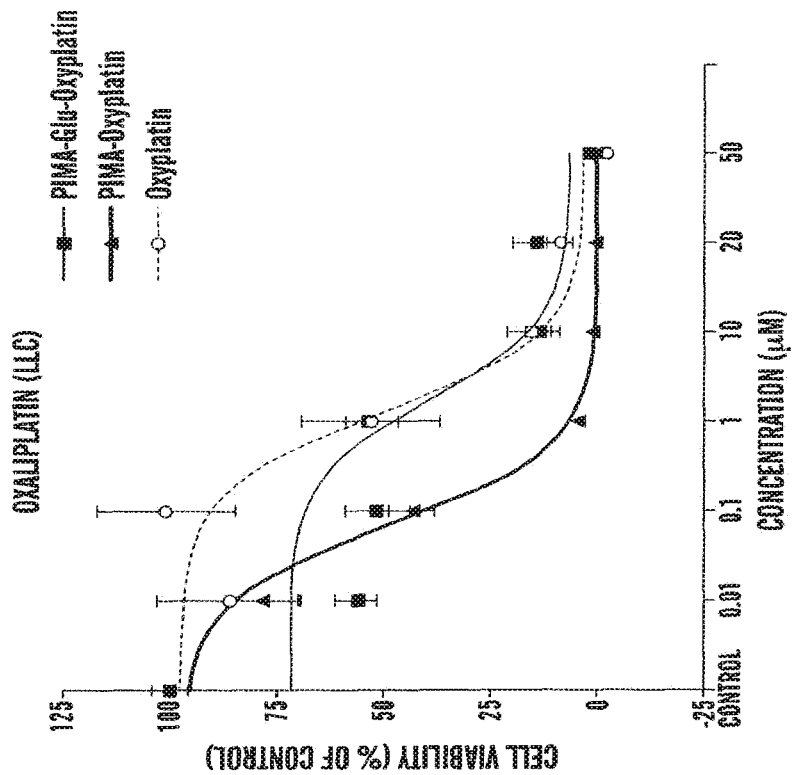
FIG. 23 is a line graph showing concentration-effect of different oxaliplatin complexes on cellular viability as measured using MTS assay.
Figure 25A:
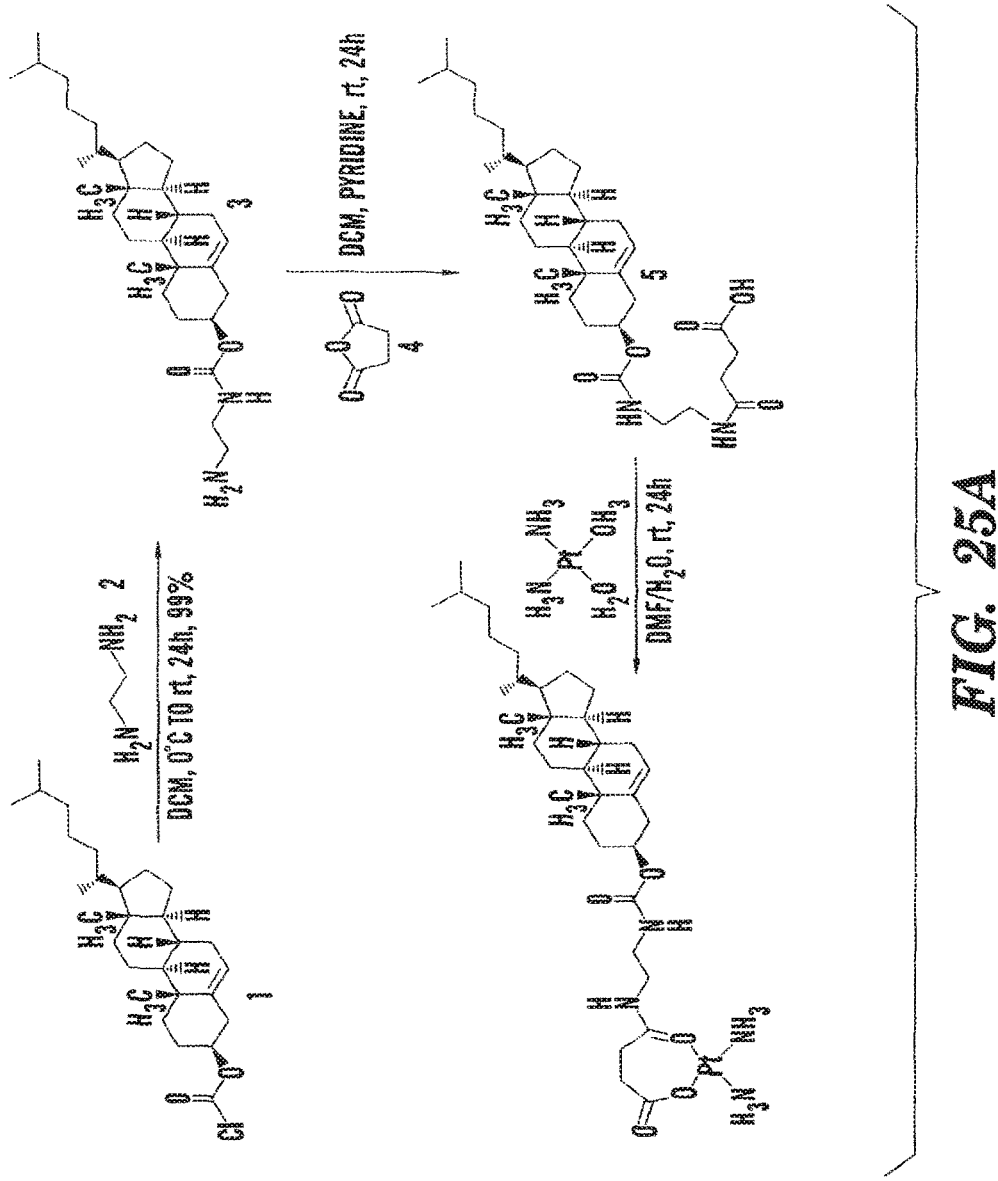
FIG. 25A is a scheme showing the synthesis of cholesterol-succinic acid conjugate and the complexation of Pt to the conjugate.
Figure 25B:
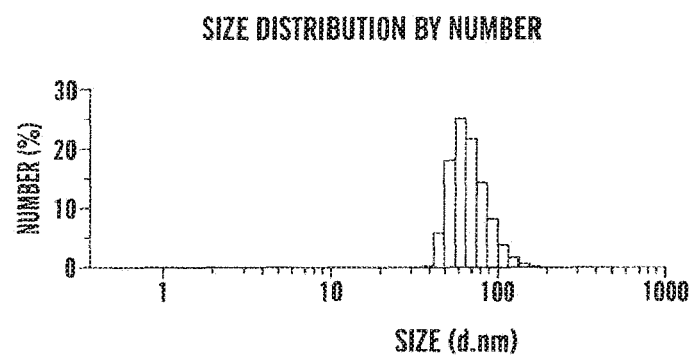
FIG. 25B shows a dynamic laser light scatter of liponanoparticles. The size of the liponanoparticles is less than 150 nm.
Figure 26:
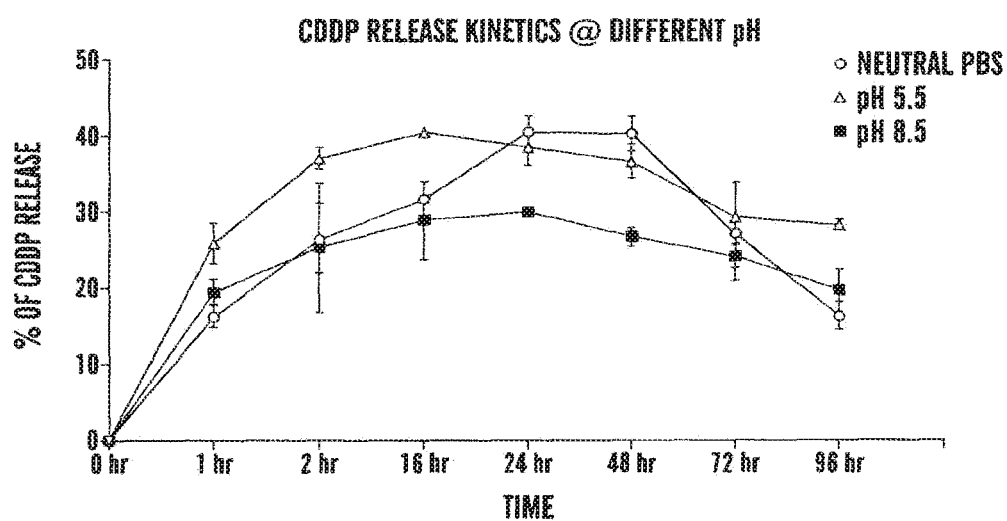
FIG. 26 is a line graph showing the release kinetics of Pt from the liponanoparticle with time and the influence of pH. The rate of release is faster in an acidic pH, which facilitates selective release of active platinate in the tumor, consistent with the acidic intratumoral pH.
Figure 27B:
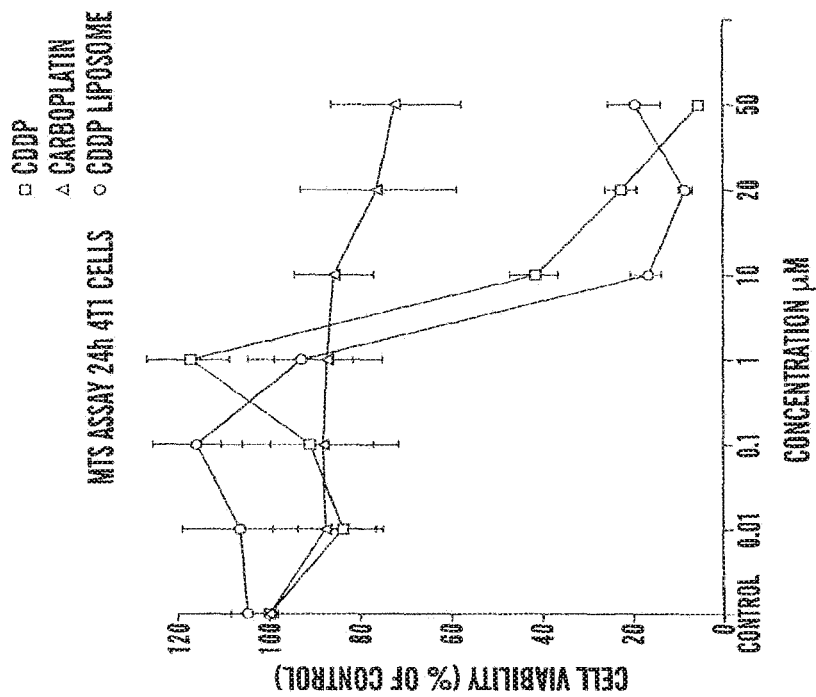
FIGS. 27A-27C are line graphs showing the effect of cisplatin-liponanoparticle on viability of 4T1 breast cancer cells. Cell viability was measured using MTS assay. The treatment with liponanoparticles results in rapid cell kill within 12 hours as compared with either cisplatin or carboplatin (FIG. 27A). At all three time points cisplatin-liponanoparticle was found to be more effective than cisplatin. Carboplatin is the least effective of all platinates tested (FIGS. 27A-27C).
Figure 27A:
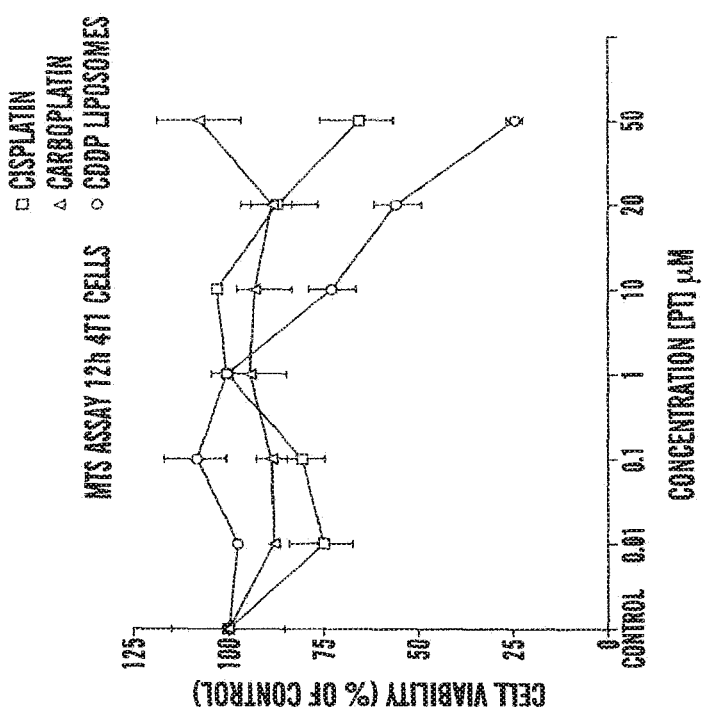
Figure 27C:
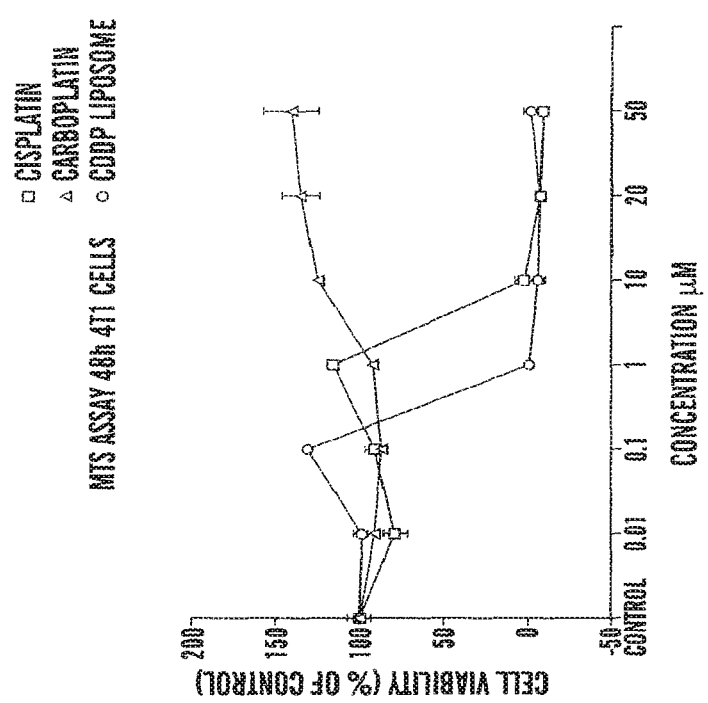
Figure 28B:
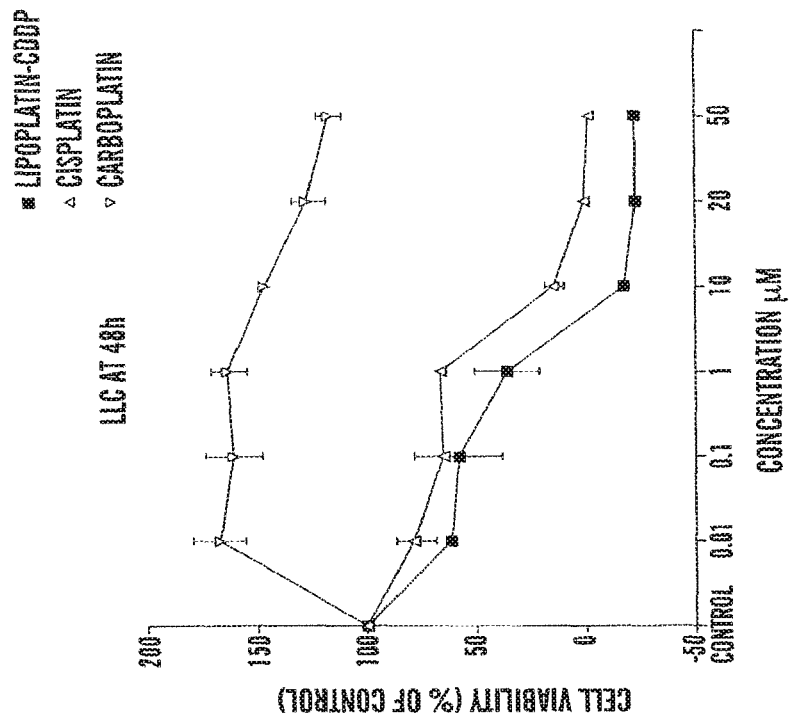
FIGS. 28A and 28B are line graphs showing the effect of cisplatin-liponanoparticle on viability of a cisplatin-resistant hepatocellular cancer cell line (CP20) and on a Lewis lung cancer cell line (LLC) respectively. Cisplatin acts on CP20 only at the highest concentration, while the cells are susceptible to the cisplatin-liponanoparticle (FIG. 28A). Carboplatin has no effect at this concentration range (FIGS. 28A and 28B). Cisplatinliponanoparticle exerted superior anticancer effect than free cisplatin on LLCs (FIG. 28B).
Figure 28A:
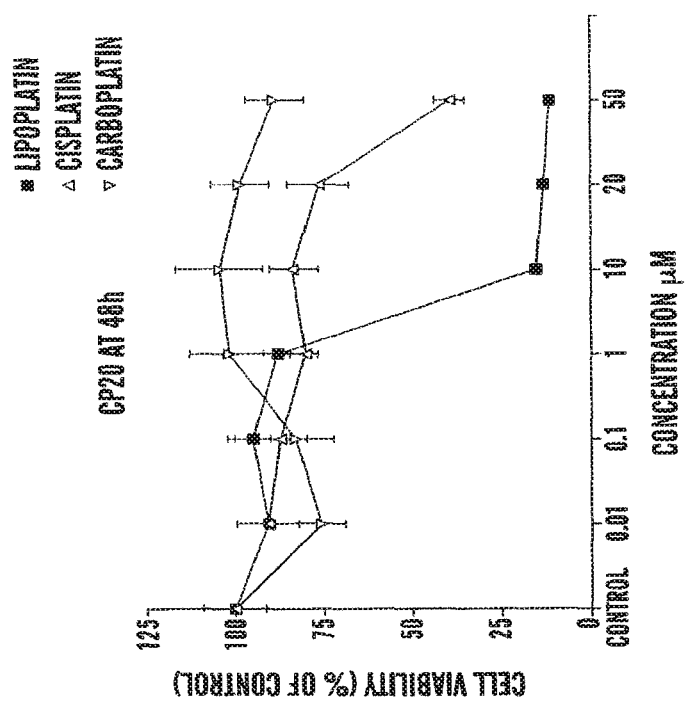
Figure 29B:
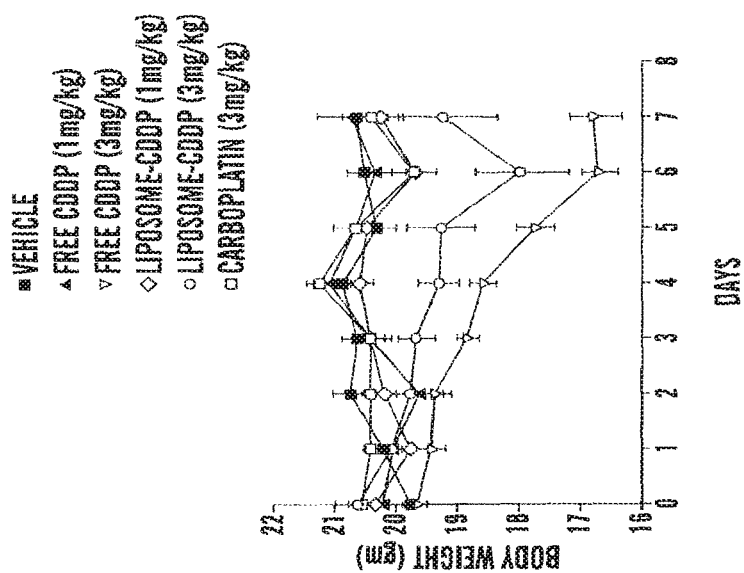
FIGS. 29A-29B are line graphs and FIGS. 29C-29E are bar graphs showing the efficacy of cisplatin-liponanoparticle in a 4T1 syngeneic tumor model in vivo. The graphs show the effect of different treatments on tumor growth (FIGS. 29A and 29C) and body weight (as a marker for systemic toxicity, FIG. 29B). Bar graphs show kidney (FIG. 29D) and spleen (FIG. 29E) weights as markers for nephrotoxicity and hematological toxicity. As seen in the FIGS. 29A-29E, cisplatin-liponanoparticle induced greater antitumor activity with reduced systemic, nephrotoxicity.
Figure 29A:
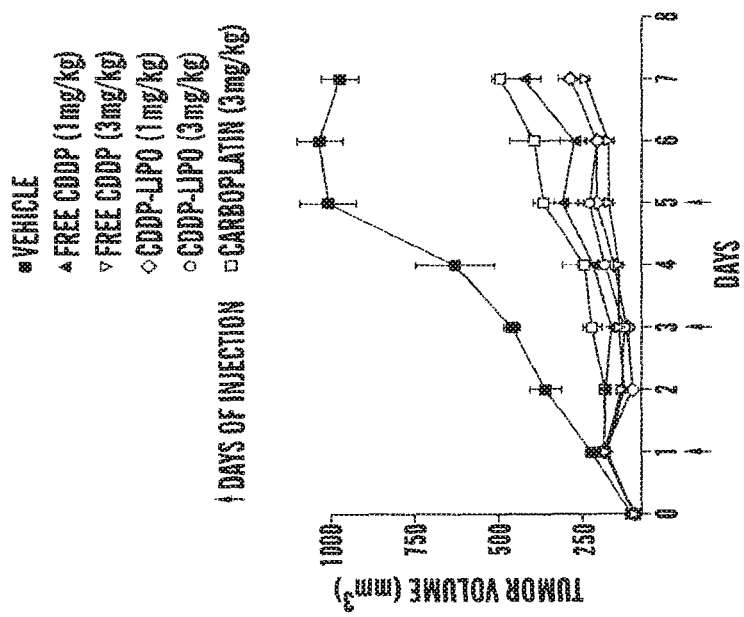
Figures 29C, 29D, 29E:
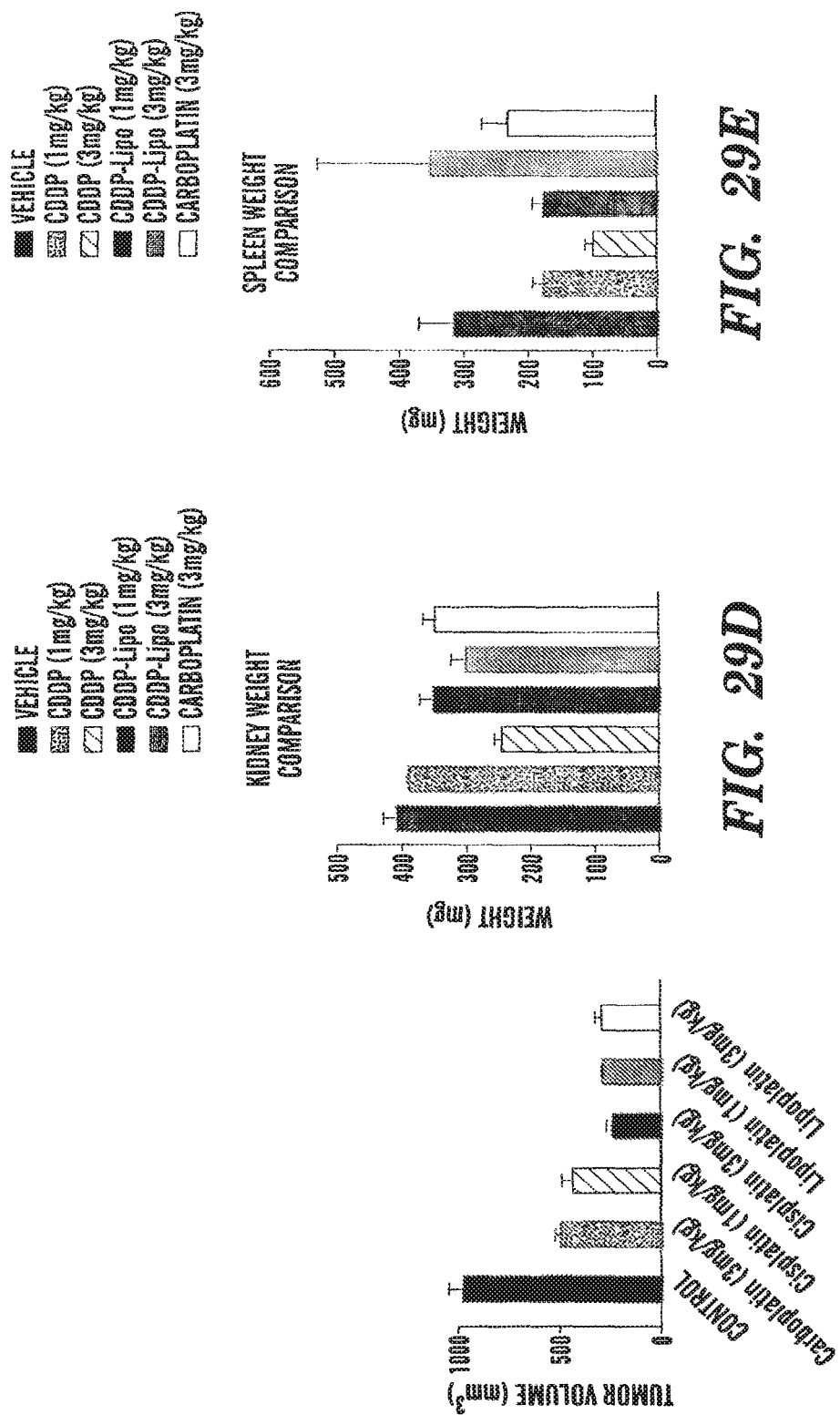

As seen in FIG. 23, at a dose of 15 mg/kg of free oxaliplatin, all the animals died due to systemic toxicity. In contrast no toxicity was evident even at this dose in the case of oxaliplatin nanoparticle.

Example 11

Synthetic Scheme of Lipid-cisplatin Conjugate

In addition to the PMA-GA-cisplatin conjugate, the inventors have also engineered an analog, where maleic acid is conjugated to PEG end of a pegylated lipid (PEG2000-DSPE). The inventors complexed Pt to the maleic acid, resulting in the formation of a platinated lipid derivative where the Pt is at the hydrophilic end and the lipid forms the hydrophobic end. These form micelles in water, and the loading efficiency is 45 µg/mg of lipid derivative. This can be increased by using a lower molecular weight PEG or lipid. See FIG. 10.

Example 12

Cisplatin-liponanoparticles

Materials and Method

All reactions were performed under inert conditions unless otherwise indicated. All commercially obtained compounds were used without further purification. DCM, dry DCM, Methanol, Cholesteryl Chloroformate, Cholesterol, Ethylenediamine, Succinic Anhydride, Silver Nitrate, Sodium Sulphate, Pyridine, Cisplatin, L-a-Phosphatidylcholine, Sephadex G-25 and 1,2-Phenylenediamine were bought from Sigma-Aldrich. 1,2-Distearoyl-sn-Glycero-3-Phosphoethanolamine-N-[Amino(Polythylene Glycol) 2000] and the mini handheld Extruder kit (including 0.2 µm Whatman Nucleopore Track-Etch Membrane, Whatman filter supports and 1.0 mL Hamiltonian syringes) were bought from Avanti Polar Lipids Inc. Anhydrous solvent DMF was supplied by Acros Organics. Phosphotungstic Acid was from Ted Pella, Inc. Analytical thin-layer chromatography (TLC) was performed using precoated silica gel Aluminium sheets 60 F254 bought from EMD Laboratories. Spots on the TLC plates were visualized using alkanine permanganate or 6% Ninhydrin solution in Acetone. 1H NMR (300 MHz) spectra were obtained on a Varian Mercury 300 spectrophotometer. The chemical shifts are expressed in parts per million (ppm) using suitable deuterated NMR solvents with reference to TMS at 0 ppm. MTS reagent was supplied by Promega. The cell viability assay and release kinetic data were plotted using GraphPad Prism software. Each sample was done in triplicate.

Synthesis of (11):

1044 µL (15 eq) of ethylene diamine (12) was dissolved in 5.0 mL anhydrous DCM followed by cooling down to 0-5° C. with ice. 500.0 mg (1.0 eq) of Cholesteryl Chloroformate was dissolved in 5.0 mL anhydrous DCM and was added to the reaction mixture drop-wise over a period 15 minutes with vigorous stirring and was continued overnight until it comes to rt. The reaction was worked up using water (50 mL×3) and DCM (50 mL), followed by saturated Brine water wash. The organic layer was dried over anhydrous Sodium Sulphate, and evaporated with the help of a rotary evaporator. Light yellow colored clear oily product (13) was separated with 99.1% yield. 1H-NMR (300 MHz) d (ppm)=5.37 (s, 1H), 5.06 (S, 1H), 4.49 (bs, 1H), 3.22-3.20 (m, 2H), 2.82-2.81 (m, 2H), 2.34-2.26 (m, 2H), 2.02-1.83 (m, 6H), 1.54-0.84 (m, 37H)

Synthesis of 15:

350 mg (0.74 mmol, 1 eq) of starting material (13) was dissolved in 5.0 mL anhydrous DCM. To it 370.0 mg (3.7 mmols, 5 eq) of Succinic Anhydride (14) and catalytic amount of Pyridine was added. The stirring was continued for Id followed by work up in 0.1(N) HCl and DCM for several times. The organic layer was dried over Sodium Sulphate and evaporated to get white amorphous solid compound (15). Yield: 95% 1H-NMR (300 MHz) d (ppm)=7.72-7.70 (m, 1H), 7.54-7.53 (m, 1H), 5.37 (s, 1H), 5.07 (S, 1H), 4.49 (bs, 1H), 4.22-4.19 (m, 2H), 3.36-3.30 (m, 4H), 2.68-2.33 (m, 4H), 2.02-1.83 (m, 6H), 1.54-0.84 (m, 37H).

Synthesis of 16:

50 mg (0.166 mmol, 1 eq) of Cisplatin (16) was partially dissolved in 10.0 mL of H2O. To it 28.0 mg (0.166 mmol, 1 eq) Silver Nitrate was added and the resulting reaction mixture was stirred at rt for Id. It looked milky white and Silver Chloride was removed by centrifuging at 25000×g for 1 h. Synthesis of 7: 200 mg (0.35 mmol, 1.0 eq) of 5 was dissolved in 5.0 mL DMF. To it 20.0 mL of product 6 (conc 5.0 mg/mL, 1.0 eq) was added and stirred for Id. The reaction mixture was dried with the help of a lyophilizer. The dried product (17) was used for lipo-nanoparticle synthesis without any further purification.

General Procedure of Synthesizing Lipo-Nano Articles:

10.0 mg of L-a-Phosphatidylcholine, 5.0 mg of Cholesterol (or Pt(II)-cholesterol conjugate) and 1.0 mg of 1,2-Distearoyl-sn-Glycero-3-Phosphoethanolamine-N-[Amino (Polythylene Glycol)2000] were dissolved in 10.0 mL DCM. It was evaporated into a thin and uniform film with the help of a rotary evaporator. After thorough drying with pump it was hydrated with 1.0 mL H2O for 2 h at 60° C. The hydrated lipo-nanoparticles looked light yellow to white with little viscous texture. It was passed though Sephadex G-25 column and extruded at 65° C.

General Method of Pt(II) Quantification in Lipo-nanoparticles

A measured amount of the extruded lipo-nanoparticle was heated at 100° C. in 1.2 mg/mL concentration of 1,2-Phenylenediamine in DMF for 2 h. Pt(II) amount was calculated by UV Spectrophotometry (Shimadzu 2450).

Release Kinetics

Concentrated drug loaded lipo-nanoparticles were suspended with buffer (or cell lysate) and sealed in a dialysis membrane (MW cutoff 1000, Spectrum Lab). The dialysis bags were incubated in 1.0 mL PBS buffer at room temperature with gentle shaking. A 10 µL portion of the aliquot was collected from the incubation medium at predetermined time intervals, and the released drug was quantified by UV Spectrophotometer (Shimadzu 2450). The results are plotted as percentage release.

Sample Preparation for TEM

High resolution TEM images were obtained on a Jeol 2011 high contrast digital TEM. For sample preparation, lacy carbon 300 mesh copper grids (Electron microscopy Science) were dipped in the aqueous solution of the lipo-nanoparticle. It was allowed to air dry followed by staining it with 2% aqueous solution of Phosphotungstic acid. The size distribution of lipo-nanoparticles was studied by dynamic light scattering (DLS), which was performed at 26° C. on a Malvern Zetasizer DLS-system equipped with a He—Ne laser.

Cell Viability Assay

In a 96 well plate, $2\times10^3$ cells were plated. After 4 h, cells were treated with different concentrations of free drug or lipo-nanoparticles. Cells without any treatment were kept as control. After 48 h, cell viability was assessed using standard MTS assay according to manufacturer's instructions.

In Vivo Efficacy and Toxicity Studies

BALB/c mice were inoculated s.c. with $1\times10^5$ of 4T1 breast tumor cells in 100 µL PBS on right flank of mice. Treatment with different anticancer agents either free or entrapped in nanoparticles was started on day when tumor volume reached 200 mm³. Typically the animals received free drug alone or in nanoparticles through i.v route every alternate day for total of three dosages. Once the tumor volume reached 2000 mm3 in control group, mice were sacrificed. Tumor, kidney, spleen, lung, liver were harvested and processed for paraffin embedding and sectioning.

All patents and publications cited herein are hereby incorporated by reference.

What is claimed:

1. A dicarbonyl-lipid compound having the structure

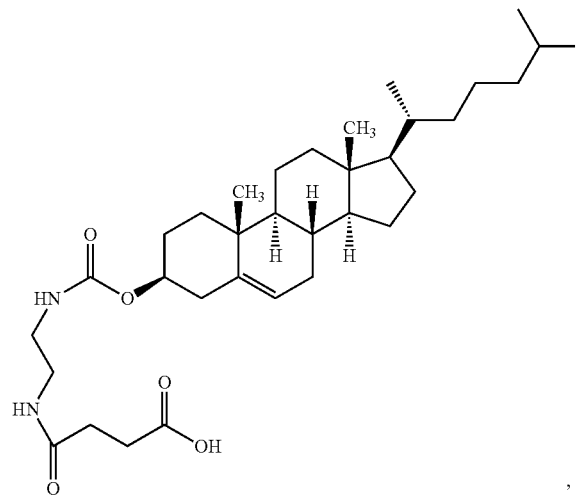

and wherein a platinum compound is dissociably linked to the dicarbonyl-lipid compound by a monocarboxylato bond and a Pt-O coordinate bond.

2. The dicarbonyl-lipid compound of claim 1, wherein the platinum compound is a Pt(II) compound or a Pt(IV) compound.

3. The dicarbonyl-lipid compound of claim 1, wherein the platinum compound is a Pt(II) compound selected from the group consisting of cisplatin, oxaliplatin, carboplatin, paraplatin, sartraplatin, and combinations thereof.

4. A vesicle, micelle, liposome or nanoparticle compound comprising a dicarbonyl-lipid compound of claim 1 and a platinum compound, wherein the platinum compound is dissociably linked to the compound of claim 1.

5. The nanoparticle of claim 4, wherein the platinum compound is selected from Pt(II) compounds, Pt(IV) compounds, and any combinations thereof.

6. The nanoparticle of claim 5, wherein said platinum compound is a Pt(II) compound selected from the group consisting of cisplatin, oxaliplatin, carboplatin, paraplatin, sartraplatin, and combinations thereof.

* * * * *